(12) United States Patent
Cardozo et al.

(10) Patent No.: US 7,429,482 B2
(45) Date of Patent: Sep. 30, 2008

(54) SCREENING TOOLS FOR DISCOVERY OF NOVEL ANABOLIC AGENTS

(75) Inventors: Christopher Cardozo, New York City, NY (US); William A. Bauman, New Rochelle, NY (US); Weidong Zhao, Riverdale, NY (US); Yong Wu, Edison, NJ (US)

(73) Assignee: United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 11/331,854

(22) Filed: Jan. 12, 2006

(65) Prior Publication Data

US 2006/0166324 A1 Jul. 27, 2006

Related U.S. Application Data

(60) Provisional application No. 60/644,345, filed on Jan. 13, 2005.

(51) Int. Cl.
*C12N 15/00* (2006.01)
*C12N 15/63* (2006.01)
*C07H 21/04* (2006.01)
*C12Q 1/68* (2006.01)

(52) U.S. Cl. ..................... 435/320.1; 435/455; 536/24.1
(58) Field of Classification Search ........................ None
See application file for complete search history.

(56) References Cited

U.S. PATENT DOCUMENTS

| | | | | |
|---|---|---|---|---|
| 6,087,164 | A * | 7/2000 | Hochberg et al. | ........ 435/320.1 |
| 6,645,974 | B2 | 11/2003 | Hutchinson et al. | |
| 2002/0123456 | A1 | 9/2002 | Glass | |
| 2003/0077288 | A1 | 4/2003 | Goldberg et al. | |
| 2003/0129686 | A1 | 7/2003 | Glass et al. | |
| 2005/0265978 | A1 | 12/2005 | Chancellor et al. | |
| 2006/0069049 | A1* | 3/2006 | Goldberg et al. | .............. 514/44 |

OTHER PUBLICATIONS

Edstrom et al (Atrogin-1/MAFbx and MuRF1 Are Downregulated in Aging-Related Loss of Skeletal Muscle, Journal of Gerontology, 2006. 61A:663-674).*
Frank et al (Clinical Biomarkers in Drug Discovery and Development, Nature Reviews, 2003. 2:566-580).*
Wagner (Overview of biomarkers and surrogate endpoints in drug development, Disease Markers, 2002: 18:41-46).*
Feng (Research Issues and Strategies for genomic and proteomic biomarker discovery and validation: a statisitical perspective, Future Medicine, 2004. 5(6):709-719).*
Aarnisalo et al., "Transcription Activating and Repressing Functions of the Androgen Receptor Are Differentially Influenced by Mutations in the Deoxyribonucleic Acid-Binding Domain," *Endocrinology*, 140(7):3097-3105, 1999.

Abu-Shakra et al., "Nerve stimulation and denervation induce differential patterns of immediate early gene mRNA expression in skeletal muscle," *Mol. Brain Res.*, 18(3):216-220, 1993.
Adler et al., "Multiple Components of a Complex Androgen-Dependent Enhancer," *Mol. Endocrinol.*, 5(11):1587-1596, 1991.
Altschul et al., "Gapped Blast and PSI-Blast: a new generation of protein database search programs," *Nucleic Acids Res.*, 25:3389-3402, 1977.
Angus et al., "Role of Intronic E- and N-box Motifs in the Transcriptional Induction of the Acetylcholinesterase Gene during Myogenic Differentiation," *J. Biol. Chem.*, 276(20):17603-17609, 2001.
Araki et al., "A Cluster of Four Sp1 Binding Sites Required for Efficient Expression of the Human Insulin Receptor Gene," *J. Biol. Chem.*, 266(6):3944-3948, 1991.
Bains et al., "Cardiac Actin Is the Major Actin Gene Product in Skeletal Muscle Cell Differentiation In Vitro," *Mol. Cell. Biol.*, 4(8):1449-1453, 1984.
Barbulescu et al., "New Androgen Response Elements in the Murine Pem Promoter Mediate Selective Transactivation," *Mol. Endocrinol.*, 15(10):1803-1816, 2001.
Batt et al., "Differential gene expression profiling of short and long term denervated muscle," *FASEB J.*, express article 10.1096/fj.04-3640fje. pp. 1-34, Epub Nov. 15, 2005.
Blagden et al., "Accelerated Response of the *myogenin* Gene to Denervation in Mutant Mice Lacking Phosphorylation of Myogenin at Threonine 87," *Mol. Cell. Biol.*, 24(5):1983-1989, 2004.
Bodine et al., "Identification of Ubiquitin Ligases Required for Skeletal Muscle Atrophy," *Science*, 294(5547):1704-1708, 2001.
Catala et al., "A Skeletal Muscle-Specific Enhancer Regulated by Factors Binding to E and CArG Boxes is Present in the Promoter of the Mouse Myosin Light-Chain 1A Gene," *Mol. Cell. Biol.*, 15(8):4585-4596, 1995.
Cheng et al., "Oct-1 Is Involved in the Transcriptional Repression of the Gonadotropin-Releasing Hormone Receptor Gene," *Endocrinology*, 143(12):4693-4701, 2002.
Clay et al., "Transcriptional Repression of the Glycoprotein Hormone α Subunit Gene by Androgen May Involve Direct Binding of Androgen Receptor to the Proximal Promoter," *J. Biol. Chem.*, 268(18):13556-13564, 1993.
Crabtree, Gerald R., "Generic Signals and Specific Outcomes: Signaling through $Ca^{2+}$, Calcineurin, and NF-AT," *Cell*, 96:611-614, 1999.
Dehoux et al., "Induction of MafBx and Murf ubiquitin ligase mRNAs in rat skeletal muscle after LPS injection," *FEBS Letters*, 544:214-217, 2003.
Dehoux et al., "Role of the Insulin-Like Growth Factor I Decline in the Induction of Atrogin-1/MAFbx during Fasting and Diabetes," *Endocrinology*, 145(11):4806-4812, 2004.
Delany et al., "Transcriptional Repression of Insulin-Like Growth Factor I by Glucocorticoids in Rat Bone Cells," *Endocrinology*, 136(11):4776-4781, 1995.

(Continued)

*Primary Examiner*—Quang Nguyen
(74) *Attorney, Agent, or Firm*—Klarquist Sparkman, LLP

(57) ABSTRACT

The disclosure provides nucleic acids including the polynucleotide sequence of the human MAFbx core promoter involved in muscle specific expression. Also provided are reporters operably linked to a polynucleotide sequence including MAFbx transcription regulatory sequences, and constructs including polynucleotides that encode reporters and other polynucleotide sequences operably linked to the MAFbx core transcription regulatory sequence. Systems for identifying agents that inhibit muscle loss and/or increase muscle mass or tone are also provided.

11 Claims, 28 Drawing Sheets

OTHER PUBLICATIONS

Delany et al., "Glucocorticoid Suppression of IGF I Transcription in Osteoblasts," *Mol. Endocrinol.*, 15(10):1781-1789, 2001.

Ferrando et al., "Testosterone administration to older men improves muscle function: molecular and physiological mechanisms," *Am. J. Physiol. Endocrinol. Metab.*, 282:E601-E607, 2002.

Furuno et al., "Role of Different Proteolytic Systems in the Degradation of Muscle Proteins during Denervation Atrophy," *J. Biol. Chem.*, 265(15):8550-8557, 1990.

Gayan-Ramirez et al., "Nandrolone decanoate does not enhance training effects but increases IGF-I mRNA in rat diaphragm," *J. Appl. Physiol.*, 88:26-34, 2000.

Gilley et al., "FOXO transcription factors directly activate *bim* gene expression and promote apoptosis in sympathetic neurons," *J. Cell Biol.*, 162(4):613-622, 2003.

Glass, David J., Molecular mechanisms modulating muscle mass, *Trends in Molecular Medicine*, 9(8):344-350, 2003.

Gomes et al., "Atrogin-1, a muscle-specific F-box protein highly expressed during muscle atrophy," *PNAS*, 98(25):14440-14445, 2001.

Gregory et al., "Effects of testosterone replacement therapy on skeletal muscle after spinal cord injury," *Spinal Cord*, 41(1):23-28, 2003.

Haddad et al., "Atrophy responses to muscle inactivity. II. Molecular markers of protein deficits," *J. Appl. Physiol.*, 95:791-802, 2003.

Hyatt et al., "Nerve activity-independent regulation of skeletal muscle atrophy: role of MyoD and myogenin in satellite cells and myonuclei," *Am J Physiol Cell Physiol*, 285(5):C1161-C1173, 2003.

Janssen et al., "The Healthcare Costs of Sarcopenia in the United States," *JAGS*, 52(1):80-85, 2004.

Kim et al, "Structure and Function of a Human Insulin-like Growth Factor-I Gene Promoter," *Mol. Endocrinol.*, 5(12):1964-1972, 1991.

Kostrominova et al., "Comparison of gene expression of 2-mo denervated, 2-mo stimulated-denervated, and control rat skeletal muscles," *Physiol. Genomics*, 22(2):227-243, 2005.

Krempler and Brenig, "Zinc finger proteins: watchdogs in muscle development," *Mol. Gen. Genet.*, 261(2):209-215, 1999.

Latres et al., "Insulin-like Growth Factor-1 (IGF-1) Inversely Regulates Atrophy-induced Genes via the Phosphatidylinositol 3-Kinase/Akt/Mammalian Target of Rapamycin (P13K/Akt/mTOR) Pathway," *J. of Biol. Chem.*, 280(4):2737-2744, 2005.

Lecker et al., "Multiple types of skeletal muscle atrophy involve a common program of changes in gene expression," *FASEB J.*, 18:39-51, 2004.

Lee et al., "Regulation of Muscle Protein Degradation: Coordinated Control of Apoptotic and Ubiquitin-Proteasome Systems by Phosphatidylinositol 3 Kinase," *J. Am. Soc. Nephrol.*, 15:1537-1545, 2004.

Lewis et al., "Role of IGF-I and IGF-binding proteins within diaphragm muscle in modulating the effects of nandrolone," *Am. J. Physiol. Endocrinol. Metab.*, 282:E483-E490, 2002.

Li et al., "AKT-Independent Protection of Prostate Cancer Cells from Apoptosis Mediated through Complex Formation between the Androgen Receptor and FKHR," *Mol. Cell. Biol.*, 23(1):104-118, 2003.

Machida and Booth, "Changes in signalling molecule levels in 10-day hindlimb immobilized rat muscles," *Acta. Physiol. Scand.*, 183(2):171-179, 2005.

Magnusson et al., "Denervation-induced alterations in gene expression in mouse skeletal muscle," *Eur. J. Neurosci.*, 21(2):577-580, 2005.

Mauras et al., "Testosterone Deficiency in Young Men: Marked Alterations in Whole Body Kinetics, Strength, and Adiposity," *J. Clin. Endocrinol. Metab.*, 83(6):1886-1892, 1998.

McCall et al., "Transcriptional regulation of IGF-I expression in skeletal muscle," *Am. J. Physiol. Cell Physiol.*, 285:C831-C839, 2003.

Medina et al., "Activation of the ubiquitin-ATP-dependent proteolytic system in skeletal muscle during fasting and denervation atrophy," *Biomed. Biochem. Acta.*, 50(4-6):347-356, 1991.

Mittanck et al., "Essential promoter elements are located within the 5' untranslated region of human insulin-like growth factor-I exon I," *Molecular and Cellular Endocrinology*, 126:153-163, 1997.

Morgenstern and Land, "Advanced mammalian gene transfer: high titre retroviral vectors with multiple drug selection markers and a complementary helper-free packaging cell line," *Nucleic Acids Res.*, 18(12):3587-3596, 1990.

Palvimo et al., "Dominant Negative Regulation of *Trans*-Activation by the Rat Androgen Receptor: Roles of the N-terminal Domain and Heterodimer Formation," *Mol. Endocrinol.*, 7(11):1399-1407, 1993.

Pickart, CM, "Mechanisms Underlying Ubiquitination," *Annu. Rev. Biochem.*, 70:503-533, 2001.

Rawls and Olson, "MyoD Meets Its Maker," *Cell*, 89:5-8, 1997.

Sakuma et al., "Differential adaptation of growth and differentiation factor 8/myostatin, fibroblast growth factor 6 and leukemia inhibitory factor in overloaded, regenerating and denervated rat muscles," *Biochem. Biophy.s Acta.*, 1497(1):77-88, 2000.

Sandri et al., "Foxo Transcription Factors Induce the Atrophy-Related Ubiquitin Ligase Atrogin-1 and Cause Skeletal Muscle Atrophy," *Cell*, 117:399-412 & 5 pages Supplemental Data, 2004.

Sheffield-Moore and Urban, "An overview of the endocrinology of skeletal muscle," *Trends in Endocrinology and Metabolism*, 15(3):110-115, 2004.

Sheffield-Moore et al., "Short-Term Oxandrolone Administration Stimulates Net Muscle Protein Synthesis in Young Men," *JCE&M*, 84(8):2705-2711, 1999.

Singleton et al., "Dexamethasone Inhibits Insulin-Like Growth Factor Signaling and Potentiates Myoblast Apoptosis," *Endocrinology*, 141(8):2945-2950, 2000.

Smith et al., "A 310-bp minimal promoter mediates smooth muscle cell-specific expression of telokin," *Am. J. Physiol.*, 274:C1188-C1195, 1998.

Spungen et al., "Soft tissue body composition differences in monozygotic twins discordant for spinal cord injury," *J. Appl. Physiol.*, 88(4):1310-1315, 2000.

Stitt et al., "The IGF-1/PI3K/Akt Pathway Prevents Expression of Muscle Atrophy-Induced Ubiquitin Ligases by Inhibiting FOXO Transcription Factors," *Mol. Cell*, 14:395-403, 2004.

Storbeck et al., "Definition of Regulatory Sequence Elements in the Promoter Region and the First Intron of the Myotonic Dystrophy Protein Kinase Gene," *J. Biol. Chem.*, 273(15):9139-9147, 1998.

Taylor et al., "Anabolic-Androgenic Steroid Administration Causes Hypertrophy of Immobilized and Nonimmobilized Skeletal Muscle in a Sedentary Rabbit Model," *Am. J. Sports Med*, 27(6):718-727, 1999.

Tiao et al., "Sepsis Stimulates Nonlysosomal, Energy-dependent Proteolysis and Increases Ubiquitin mRNA Levels in Rat Skeletal Muscle," *J. Clin. Invest.*, 94:2255-2264, 1994.

Urban et al., "Testosterone administration to elderly men increases skeletal muscle strength and protein synthesis," *Am. J. Physiol.*, 269(5 Pt. 1):E820-E826, 1995.

Vignati et al., "A human and mouse pregnane X receptor reporter gene assay in combination with cytoxicity measurements as a tool to evaluate species-specific CYP3A induction," *Toxicology*, 199:23-33, 2004.

Wang et al., "Runx1 prevents wasting, myofibrillar disorganization, and autophagy of skeletal muscle," *Genes and Development*, 19:1715-1722, 2005.

Wheeler et al., "An E-box within the MHC IIB gene is bound by MyoD and is required for gene expression in fast muscle," *Am. J. Physiol.*, 276(5 Pt. 1):C1069-C1078, 1999.

Wimalawansa et al., "Reversal of weightlessness-induced musculoskeletal losses with androgens: quantification by MRI," *J. Appl Physiol.*, 86(6):1841-1846, 1999.

Wray et al., "Sepsis upregulates the gene expression of multiple ubiquitin ligases in skeletal muscle," *Int. J. Biochem. Cell Biol.*, 35(5):698-705, 2003.

Yeh et al., "Reversal of COPD-Associated Weight Loss Using the Anabolic Agent Oxandrolone," *Chest*, 122(2):421-428, 2002.

Zhao et al., "Oxandrolone blocks glucocorticoid signaling in an androgen receptor-dependent manner," *Steroids*, 69:357-366, 2004.

Zhou et al., "A Ligand-dependent Bipartite Nuclear Targeting Signal in the Human Androgen Receptor," *J. Biol. Chem.*, 269(18):13115-13123, 1994.

Zong et al., "Mechanism of STAT3 activation by Insulin-Like Growth Factor I Receptor," *J. Biol. Chem.*, 275(20):15099-15105, 2000.

Accession No. NM058229, PRI Apr. 1, 2007, found at http://ncbi.nlm.nih.gov/entrez, printed Apr. 23, 2007.

Accession No. NM026346, PRI Apr. 1, 2007, found at http://ncbi.nlm.nih.gov/entrez, printed Apr. 23, 2007.

Accession No. AF441120, PRI Dec. 20, 2001, found at http://ncbi.nlm.nih.gov/entrez, printed Apr. 23, 2007.

Accession No. AC090193, PRI Feb. 20, 2002, found at http://ncbi.nlm.nih.gov/entrez, printed Apr. 23, 2007.

Accession No. AF254981, PRI Nov. 22, 2002, found at http://ncbi.nlm.nih.gov/entrez, printed Apr. 23, 2007.

Accession No. AF267170, PRI Nov. 8, 2002, found at http://ncbi.nlm.niyh.gov/entrez, printed Apr. 23, 2007.

* cited by examiner

A
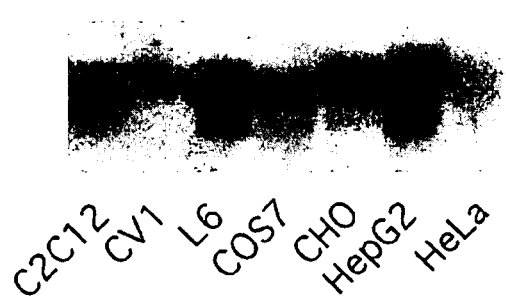
B
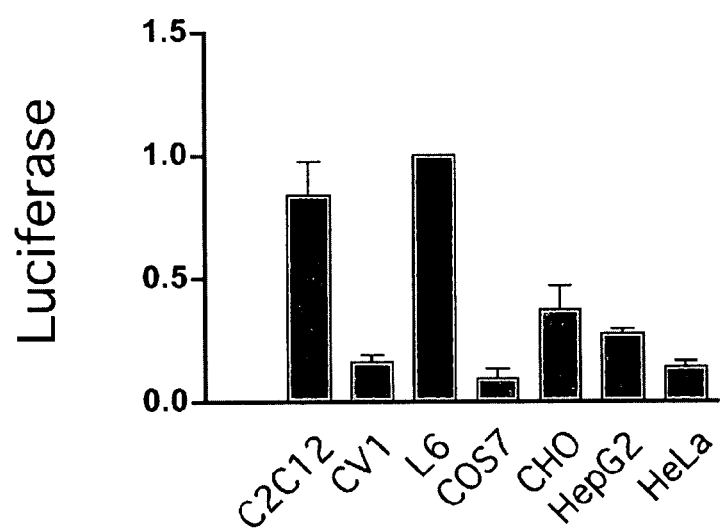
Figure 1

A
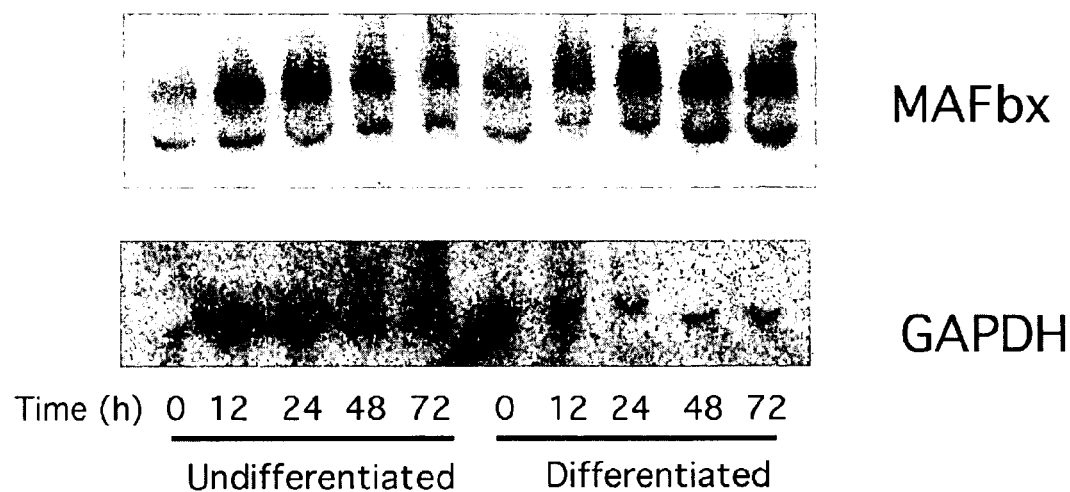
Time (h)  0  12  24  48  72    0  12  24  48  72
          Undifferentiated        Differentiated
B
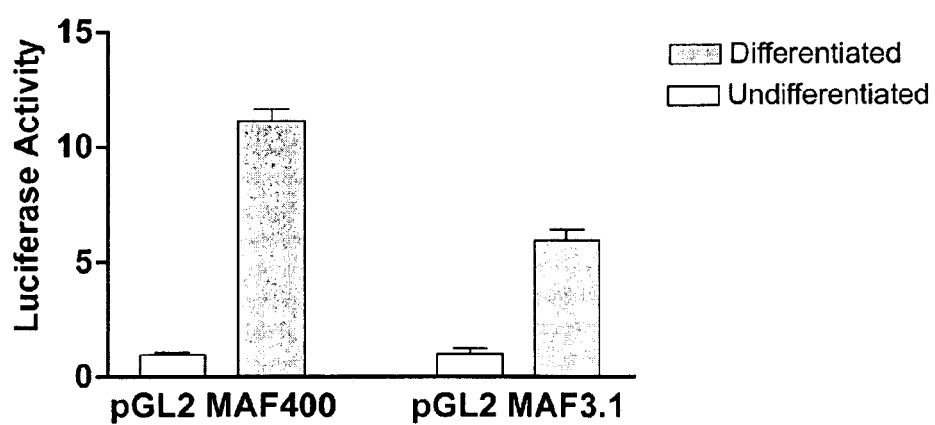
Figure 2.

```
Rat    GGCACCGAGGGTCAGCGGGACATCTGGCCTAGCCAGGCAGCTTCAAGTTT
Mouse  GGCACCGAGGGTCAGCGGGACATCTGGCCTGGCCATGCGGCTTCAAGTTT
Human  AGGTGCCAGGGGCGGCGGGGTACCCGGCCCGGCAGCACCGCTTCAAGTTT
         *   * **** * ***** * * ****  **    * **********

Rat    CCACGGGCGCAAGGTTGTGCAACTGCGAGCAGAGCGAGAGCCGCGGGCGC
Mouse  CCACGGACGCAAGGTTGTGCAACTGCGAGCAGAGCGAGAGCCGCGGGCGC
Human  CCACCGGCGC--GGTTGTGCAACCGGGAGGGGAGCGTGAGCCGCAGGCGC
       **** * ***  ********** * ***     ***** ******* *****

Rat    CTCGGAAAACAAGGCGAGCCCATAAACAAAGCCACGTGGCCTCGGGGCGC
Mouse  CTCGGAAAACAAGGCGAGCCTATAAACAAAGCCACGTGGCCTCGGGGCGC
Human  CTCGGAAAACAAGCCGAGCCCATAAACAAAGCCACGTGGCCTCCGGGCC-
       *************  ****** **********************  ****

Rat    AGGGGGGGC----CGGGCTAAGAGCAGGAGGCTCTTCCGGCAACAAAGAG
Mouse  GGGGGGGGGGGGGCGGGCTAAGAGCAGGCGGCTCTTCCGGCAACAAAGAG
Human  --GGGGGGC----CGGGCTAAGAGCGGGCGGCTCTTCCGGCAACAAAGAG
         ******    ************ ** *******************

Rat    ACGGGGCAGCGGCCCGGGATAAATACTGCG-CTCCGGCAGCCGCGCAGCA
Mouse  ACGGGGCAGCGGCCCGGGATAAATACTGCG-CTCGGGCAGCCGCTCAGCA
Human  CTGCGGCCGGCTGCGGGGATAAATACTGCGGCAGCTACTGCCGCGCAGCA
        * ***  *   *  * ************* *  * ***** *****

Rat    TTCCCGAAGTCAGGACGCGACACGCGACCCTCCTCAGCGCCTGATCCCCT
Mouse  TTCCCAGAGTCAGGA-------GGCGACCTTCCCCAACGCCTGCGCCCCT
Human  CTCCCGGAGCCTGCAA--CGCTTGAGATCCTCTCC-GCGCCCGCCACCCC
        ****  ** *   *    **   *   * **    ** ***    ***

Rat    GCCAGTGCAAGGACCCTCGCGCCCACCCAGGACCCGCAACCCTCCACATC
Mouse  GTGAGTGCAAGGATCCCCGCGCCCACCCAGGATCCGCAGCCCTCCACACT
Human  G------CAGGGTGCCCCGCGCC------GTTCCCGCCGCCCC-------
       *      ** ** ** ******       *    ****   ***

Rat    AGTTCCCCGACTCTTGTTCCAGTTGCCGCCTGCGT---TCCCTAGCGTCT
Mouse  AGTTGACCCACTCTTGTCCCGGTCGCCGCCTGCGTCGTTCCCCAGCATCT
Human  ------GCCGCCCCGTCGCGG--GCC-CCTGCAC----CCCGAGCATCC
             *   *  **  * * **  ***  ***** ***      *** *** **

Rat    TCCCAGAGCGGCGCATCCCCTGGGCAAGCCAGGCCGGTTCCTGGCTGTCG
Mouse  TCCCAACGCGCCGCATACCCTGGGCAAGCCAGGCCGGTTCCTGGCTGTCA
Human  GCCCGGGTGGCACGT-CCCCGAGCCCACCAGGCCGGCCCC-GTCTCCCC
        ***   *  * *   ***  *  *  ** ********   **  * *  *

Rat    ATCCGTCCTATCCGTCGGTCGCGTCCGCTCTCGGTACCATG  (SEQ ID NO:4)
Mouse  ATCCGTCCCGTCCGTCGGTCGCGTCCGCGCTCTGTACCATG  (SEQ ID NO:5)
Human  ATCCGTCTAGTCCGCTCGCGGTG------------CCATG  (SEQ ID NO:6)
       *******  ****  *  * *  *           *****
```

Figure 5

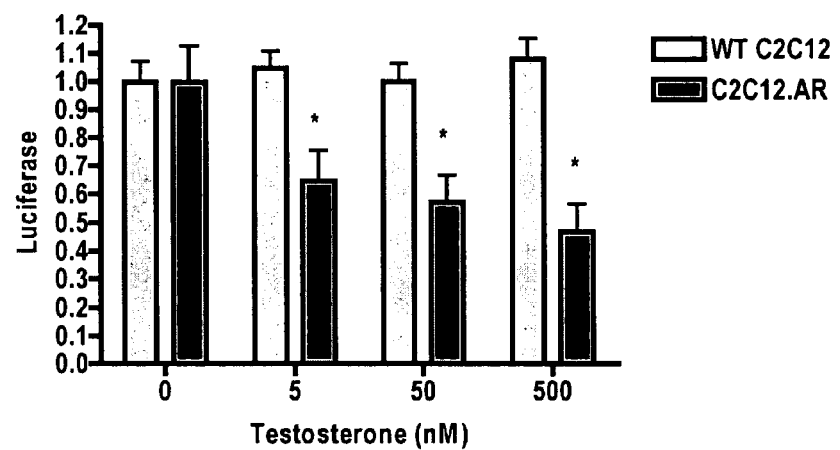
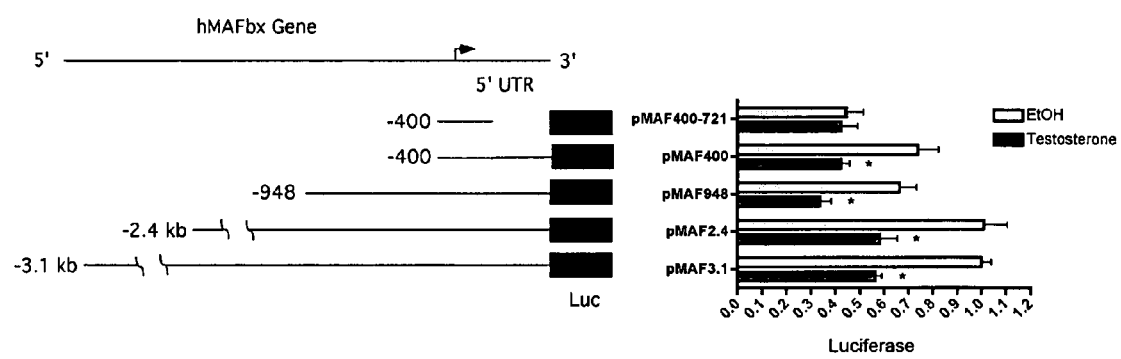
Figure 7

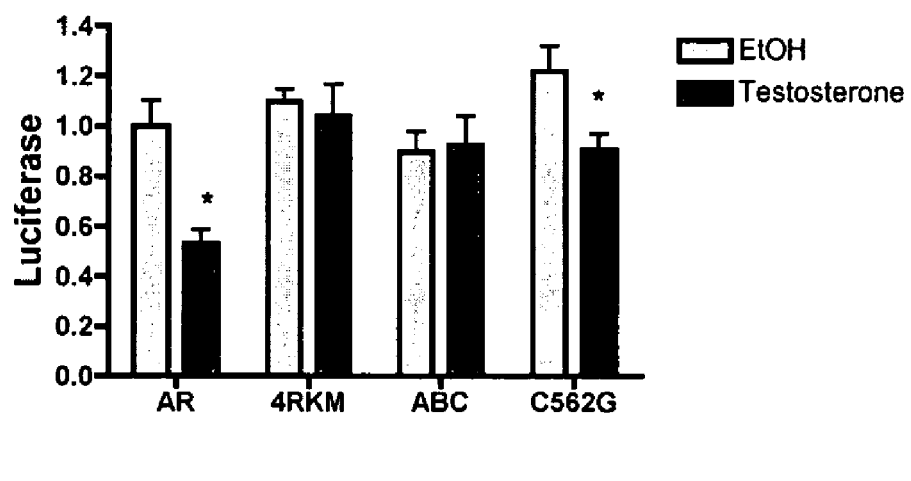
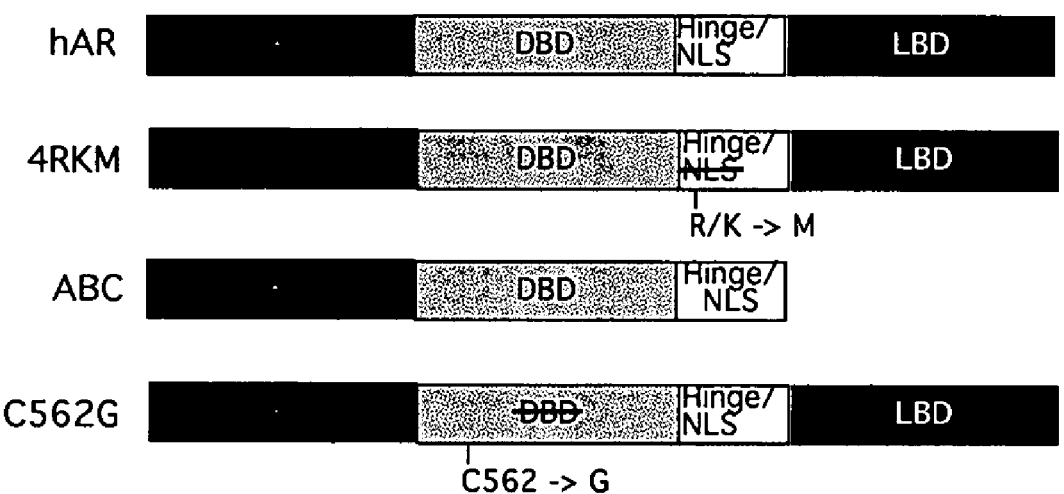
Figure 8

A
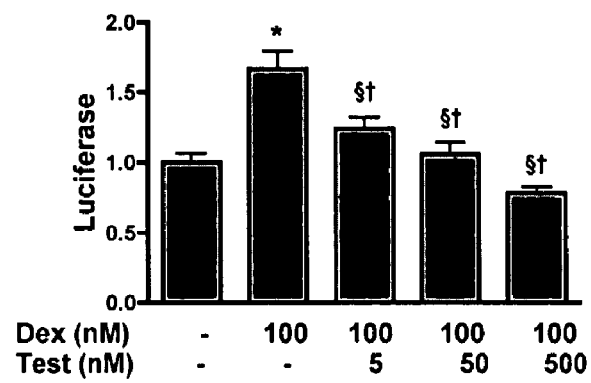
B
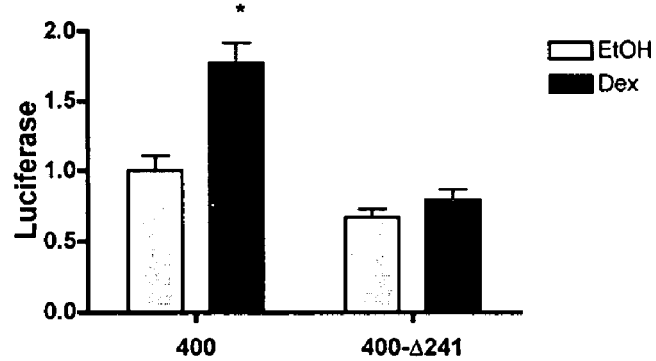
Figure 10

A
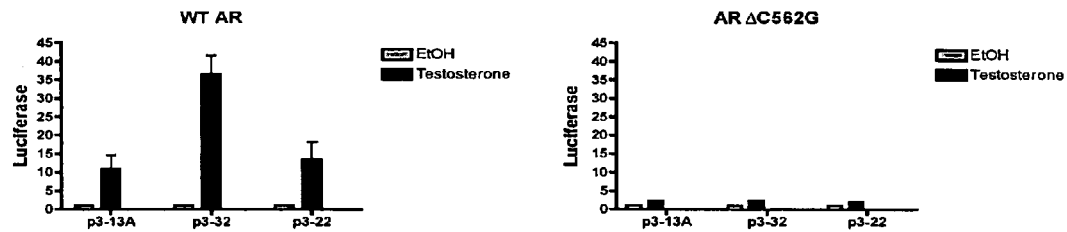
B
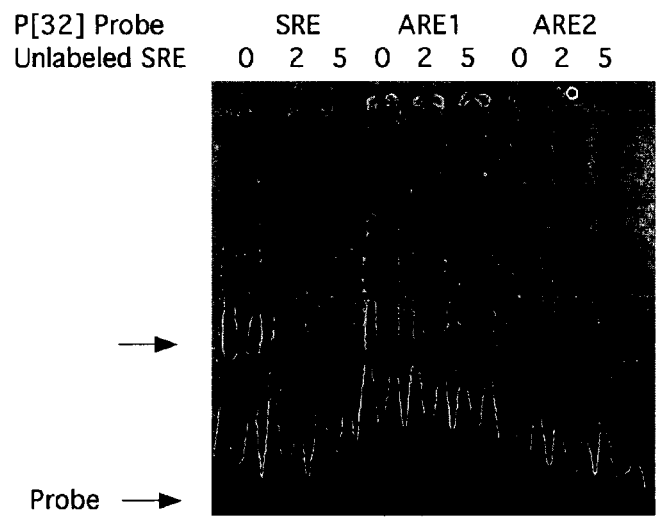
Figure 16

A
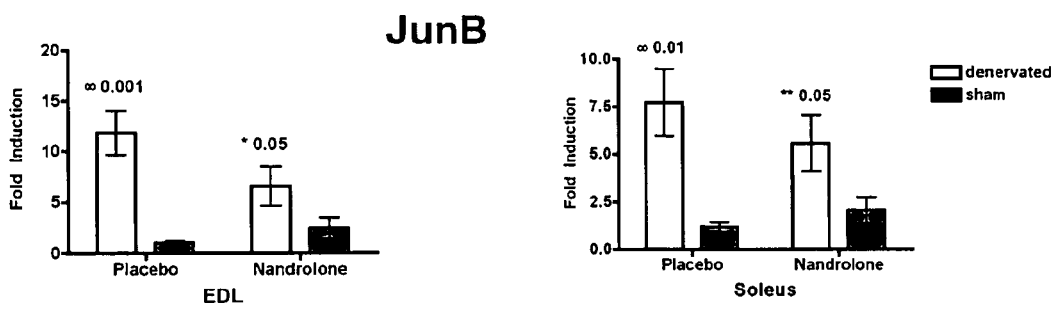
B
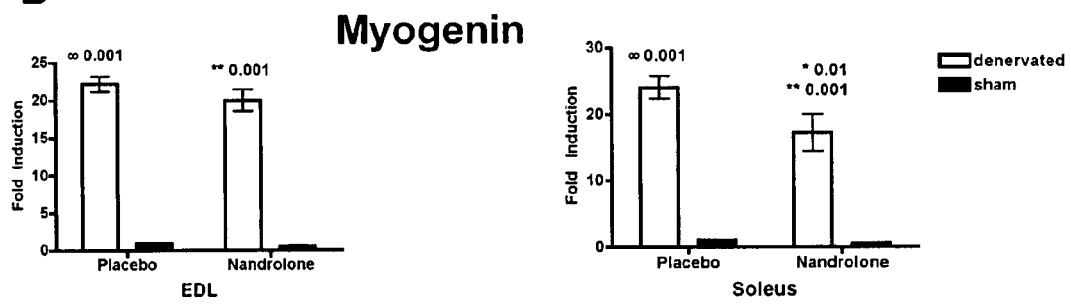
C
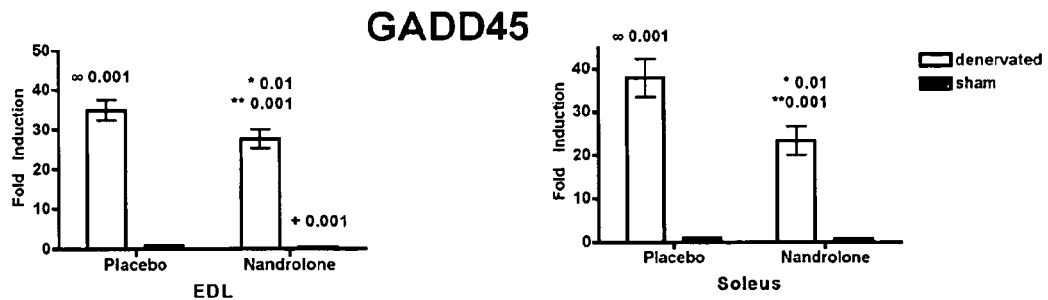
Figure 23

SEQUENCE LISTING

<160> NUMBER OF SEQ ID NOS: 44

<210> SEQ ID NO 1
<211> LENGTH: 172
<212> TYPE: DNA
<213> ORGANISM: Homo sapiens

<400> SEQUENCE: 1

| | | | | | |
|---|---|---|---|---|---|
| ccggcccggc | agcaccgctt | caagtttcca | ccggcgcggt | tgtgcaaccg | ggaggggagc | 60 |
| gtgagccgca | ggcgcctcgg | aaaacaagcc | gagcccataa | acaaagccac | gtggcctccg | 120 |
| ggccgggggg | ccgggctaag | agcgggcggc | tcttccggca | caaagagct | gc | 172 |

<210> SEQ ID NO 2
<211> LENGTH: 411
<212> TYPE: DNA
<213> ORGANISM: Homo sapiens

<400> SEQUENCE: 2

| | | | | | |
|---|---|---|---|---|---|
| ggtacccggc | ccggcagcac | cgcttcaagt | ttccaccggc | gcggttgtgc | aaccgggagg | 60 |
| ggagcgtgag | ccgcaggcgc | ctcggaaaac | aagccgagcc | cataaacaaa | gccacgtggc | 120 |
| ctccgggccg | gggggccggg | ctaagagcgg | cggctcttc | ggcaacaaa | gagctgcggc | 180 |
| cggctgcggg | gataaatact | gcggcagcta | ctgccgcgca | gcactcccgg | agcctgcaac | 240 |
| gcttgagatc | ctctccgcgc | cgccacccc | gcagggtgcc | ccgcgccgtt | ccgccgcccc | 300 |
| cgccgccccc | gtcgcgggcc | cctgcacccc | gagcatccgc | ccgggtggc | acgtccccga | 360 |
| gcccaccagg | ccggccccgt | ctccccatcc | gtctagtccg | ctcgcggtgc | c | 411 |

<210> SEQ ID NO 3
<211> LENGTH: 900
<212> TYPE: DNA
<213> ORGANISM: Homo sapiens

<400> SEQUENCE: 3

| | | | | | |
|---|---|---|---|---|---|
| tcccaacctg | cgggagccag | atacctccca | gggcttcctc | tccttcccct | cctttgctgc | 60 |
| cccaggggca | ggtctgaagg | aggactggtt | agtgacagct | aaggggcccg | gagggctggg | 120 |
| aggctgtccc | tcctcccgc | tccaaccccg | gcgcgctagg | gcggggttgg | ggcagtgagc | 180 |
| gaggtcagga | ggctgcgccc | cctactcccc | gcccggcggg | cgcggtgccg | gcccagctc | 240 |
| tgcggacggc | ccgggaggct | gatctggctg | cggaggtcga | tcctgatagc | tcgggggcag | 300 |
| gagggggct | ggccctgctc | ctcacgccca | cccgcaggg | acccagacgc | ccctccggcc | 360 |
| ccctccctgc | accccgtcag | cccgggagct | gcaggagacc | ggggcgcatc | tttccaagcg | 420 |
| ccgggcctcg | ctctgggaca | acggtgtcct | ggggcgggg | agggcgcgcg | gaggtgccag | 480 |
| gggcggcggg | gtaccggcc | cggcagcacc | gcttcaagtt | tccaccggcg | cggttgtgca | 540 |
| accgggaggg | gagcgtgagc | cgcaggcgcc | tcggaaaaca | agccgagccc | ataaacaaag | 600 |
| ccacgtggcc | tccgggccgg | ggggccgggc | taagagcggg | cggctcttcc | ggcaacaaag | 660 |
| agctgcggcc | ggctgcgggg | ataaatactg | cggcagctac | tgccgcgcag | cactcccgga | 720 |
| gcctgcaacg | cttgagatcc | tctccgcgcc | gccaccccg | cagggtgccc | cgcgccgttc | 780 |
| ccgccgcccc | gccgccccg | tcgcgggccc | ctgcaccccg | agcatccgcc | ccgggtggca | 840 |
| cgtccccgag | cccaccaggc | cggccccgtc | tccccatccg | tctagtccgc | tcgcggtgcc | 900 |

<210> SEQ ID NO 4
<211> LENGTH: 483
<212> TYPE: DNA
<213> ORGANISM: Rattus rattus

<400> SEQUENCE: 4

| | | | | | |
|---|---|---|---|---|---|
| ggcaccgagg | gtcagcggga | catctggcct | agccaggcag | cttcaagttt | ccacgggcgc | 60 |
| aaggttgtgc | aactgcgagc | agagcgagag | ccgcgggcgc | ctcggaaaac | aaggcgagcc | 120 |
| cataaacaaa | gccacgtggc | ctcggggcgc | agggggggcc | gggctaagag | caggaggctc | 180 |
| ttccggcaac | aaagagacgg | ggcagcggcc | cgggataaat | actgcgctcc | ggcagccgcg | 240 |
| cagcattccc | gaagtcagga | cgcgacacgc | gaccctcctc | agcgcctgat | ccctgccag | 300 |
| tgcaaggacc | ctcgcgccca | cccaggaccc | gcaaccctcc | acatcagttc | cccgactctt | 360 |
| gttccagttg | ccgcctgcgt | tccctagcgt | cttcccagag | cggcgcatcc | cctgggcaag | 420 |
| ccaggccggt | tcctggctgt | cgatccgtcc | tatccgtcgg | tcgcgtccgc | tctcggtacc | 480 |
| atg | | | | | | 483 |

<210> SEQ ID NO 5
<211> LENGTH: 483
<212> TYPE: DNA
<213> ORGANISM: Mus Musculus

<400> SEQUENCE: 5

| | | | | | |
|---|---|---|---|---|---|
| ggcaccgagg | gtcagcggga | catctggcct | ggccatgcgg | cttcaagttt | ccacggacgc | 60 |
| aaggttgtgc | aactgcgagc | agagcgagag | ccgcgggcgc | ctcggaaaac | aaggcgagcc | 120 |
| tataaacaaa | gccacgtggc | ctcggggcgc | ggggggggg | gggcgggcta | agagcaggcg | 180 |
| gctcttccgg | caacaaagag | acggggcagc | ggcccgggat | aaatactgcg | ctcgggcagc | 240 |
| cgctcagcat | tcccagagtc | aggaggcgac | cttccccaac | gcctgcgccc | ctgtgagtgc | 300 |
| aaggatcccc | gcgcccaccc | aggatccgca | gccctccaca | ctagttgacc | cactcttgtc | 360 |
| ccggtcgccg | cctgcgtcgt | tccccagcat | cttcccaacg | cgccgcatac | cctgggcaag | 420 |
| ccaggccggt | tcctggctgt | caatccgtcc | cgtccgtcgg | tcgcgtccgc | gctctgtacc | 480 |
| atg | | | | | | 483 |

<210> SEQ ID NO 6
<211> LENGTH: 432
<212> TYPE: DNA
<213> ORGANISM: Homo sapiens

<400> SEQUENCE: 6

| | | | | | |
|---|---|---|---|---|---|
| aggtgccagg | ggcggcgggg | tacccggccc | ggcagcaccg | cttcaagttt | ccaccggcgc | 60 |
| ggttgtgcaa | ccgggagggg | agcgtgagcc | gcaggcgcct | cggaaaacaa | gccgagccca | 120 |
| taaacaaagc | cacgtggcct | ccgggccggg | gggccgggct | aagagcgggc | ggctcttccg | 180 |
| gcaacaaaga | gctgcggccg | gctgcgggga | taaatactgc | ggcagctact | gccgcgcagc | 240 |
| actcccggag | cctgcaacgc | ttgagatcct | ctccgcgccc | gccaccccgc | agggtgcccc | 300 |
| gcgccgttcc | cgccgccccg | ccgccccegt | cgcgggcccc | tgcaccccga | gcatccgccc | 360 |
| cgggtggcac | gtcccgagc | ccaccaggcc | ggccccgtct | cccatccgt | ctagtccgct | 420 |
| cgcggtgcca | tg | | | | | 432 |

<210> SEQ ID NO 7
<211> LENGTH: 28
<212> TYPE: DNA

```
<213> ORGANISM: Artificial Sequence
<220> FEATURE:
<223> OTHER INFORMATION: 3.1 forward amplification primer

<400> SEQUENCE: 7
ccgacaacat agcaagaccc catctctc                                              28

<210> SEQ ID NO 8
<211> LENGTH: 28
<212> TYPE: DNA
<213> ORGANISM: Artificial Sequence
<220> FEATURE:
<223> OTHER INFORMATION: 3.1 reverse amplification primer

<400> SEQUENCE: 8
gagaggatct caagcgttgc aggctccg                                              28

<210> SEQ ID NO 9
<211> LENGTH: 28
<212> TYPE: DNA
<213> ORGANISM: Artificial Sequence
<220> FEATURE:
<223> OTHER INFORMATION: 2.4  forward amplification primer

<400> SEQUENCE: 9
taacacatct gtgaggtcaa cgggagtg                                              28

<210> SEQ ID NO 10
<211> LENGTH: 23
<212> TYPE: DNA
<213> ORGANISM: Artificial Sequence
<220> FEATURE:
<223> OTHER INFORMATION: 948  forward amplification primer

<400> SEQUENCE: 10
tcttagaggg ttcgggtagg ata                                                   23

<210> SEQ ID NO 11
<211> LENGTH: 20
<212> TYPE: DNA
<213> ORGANISM: Artificial Sequence
<220> FEATURE:
<223> OTHER INFORMATION: 948 reverse amplification primer

<400> SEQUENCE: 11
gactagacgg atggggagac                                                       20

<210> SEQ ID NO 12
<211> LENGTH: 26
<212> TYPE: DNA
<213> ORGANISM: Artificial Sequence
<220> FEATURE:
<223> OTHER INFORMATION: MAFbx forward amplification primer

<400> SEQUENCE: 12
caccatgcca ttcctcgggc aggact                                                26

<210> SEQ ID NO 13
<211> LENGTH: 24
<212> TYPE: DNA
<213> ORGANISM: Artificial Sequence
<220> FEATURE:
<223> OTHER INFORMATION: MAFbx reverse amplification primer

<400> SEQUENCE: 13
gaacttgaac aagttgataa agtc                                                  24
```

<210> SEQ ID NO 14
<211> LENGTH: 20
<212> TYPE: DNA
<213> ORGANISM: Artificial Sequence
<220> FEATURE:
<223> OTHER INFORMATION: extension primer

<400> SEQUENCE: 14
gactagacgg atggggagac                                           20

<210> SEQ ID NO 15
<211> LENGTH: 25
<212> TYPE: DNA
<213> ORGANISM: Artificial Sequence
<220> FEATURE:
<223> OTHER INFORMATION: Taqman forward amplification primer

<400> SEQUENCE: 15
cgcagctagg aataatggaa tagga                                     25

<210> SEQ ID NO 16
<211> LENGTH: 21
<212> TYPE: DNA
<213> ORGANISM: Artificial Sequence
<220> FEATURE:
<223> OTHER INFORMATION: Taqman reverse amplification primer

<400> SEQUENCE: 16
ggcctcagtt ccgaaaacca a                                         21

<210> SEQ ID NO 17
<211> LENGTH: 16
<212> TYPE: DNA
<213> ORGANISM: Artificial Sequence
<220> FEATURE:
<223> OTHER INFORMATION: Taqman probe

<400> SEQUENCE: 17
ccgcggttct attttg                                               16

<210> SEQ ID NO 18
<211> LENGTH: 15
<212> TYPE: DNA
<213> ORGANISM: Artificial Sequence
<220> FEATURE:
<223> OTHER INFORMATION: ARE 1.1

<400> SEQUENCE: 18
atatcttatt cctct                                                15

<210> SEQ ID NO 19
<211> LENGTH: 15
<212> TYPE: DNA
<213> ORGANISM: Artificial Sequence
<220> FEATURE:
<223> OTHER INFORMATION: ARE 1.2

<400> SEQUENCE: 19
gtaattatct gttct                                                15

<210> SEQ ID NO 20
<211> LENGTH: 15
<212> TYPE: DNA
<213> ORGANISM: Artificial Sequence
<220> FEATURE:

```
<223> OTHER INFORMATION: JRE

<400> SEQUENCE: 20
attacaccaa gtacc                                                         15

<210> SEQ ID NO 21
<211> LENGTH: 15
<212> TYPE: DNA
<213> ORGANISM: Artificial Sequence
<220> FEATURE:
<223> OTHER INFORMATION: ARE 2.1

<400> SEQUENCE: 21
acatagtaga gctca                                                         15

<210> SEQ ID NO 22
<211> LENGTH: 15
<212> TYPE: DNA
<213> ORGANISM: Artificial Sequence
<220> FEATURE:
<223> OTHER INFORMATION: ARE 2.2

<400> SEQUENCE: 22
gcacatagta gagct                                                         15

<210> SEQ ID NO 23
<211> LENGTH: 27
<212> TYPE: DNA
<213> ORGANISM: Artificial Sequence
<220> FEATURE:
<223> OTHER INFORMATION: ARE2 probe

<400> SEQUENCE: 23
ttgtagttgg gcacatagta gagctca                                            27

<210> SEQ ID NO 24
<211> LENGTH: 27
<212> TYPE: DNA
<213> ORGANISM: Artificial Sequence
<220> FEATURE:
<223> OTHER INFORMATION: ARE1 probe

<400> SEQUENCE: 24
gacttgacca tatcttattc ctctttg                                            27

<210> SEQ ID NO 25
<211> LENGTH: 27
<212> TYPE: DNA
<213> ORGANISM: Artificial Sequence
<220> FEATURE:
<223> OTHER INFORMATION: SRE probe

<400> SEQUENCE: 25
atgcattggg tacatcttgt tcacata                                            27

<210> SEQ ID NO 26
<211> LENGTH: 23
<212> TYPE: DNA
<213> ORGANISM: Artificial Sequence
<220> FEATURE:
<223> OTHER INFORMATION: myostatin forward primer

<400> SEQUENCE: 26
gagagagagg cgaatgtgga aaa                                                23
```

```
<210> SEQ ID NO 27
<211> LENGTH: 25
<212> TYPE: DNA
<213> ORGANISM: Artificial Sequence
<220> FEATURE:
<223> OTHER INFORMATION: myostatin reverse primer

<400> SEQUENCE: 27
gcttctattc tggagtacct tgtgt                                            25

<210> SEQ ID NO 28
<211> LENGTH: 24
<212> TYPE: DNA
<213> ORGANISM: Artificial Sequence
<220> FEATURE:
<223> OTHER INFORMATION: myostatin probe

<400> SEQUENCE: 28
cgaccgagtt cagactatca tctc                                             24

<210> SEQ ID NO 29
<211> LENGTH: 24
<212> TYPE: DNA
<213> ORGANISM: Artificial Sequence
<220> FEATURE:
<223> OTHER INFORMATION: MURF1 forward primer

<400> SEQUENCE: 29
cgaccgagtt cagactatca tctc                                             24

<210> SEQ ID NO 30
<211> LENGTH: 21
<212> TYPE: DNA
<213> ORGANISM: Artificial Sequence
<220> FEATURE:
<223> OTHER INFORMATION: MURF1 reverse primer

<400> SEQUENCE: 30
gtggctcagt tcctccttca c                                                21

<210> SEQ ID NO 31
<211> LENGTH: 20
<212> TYPE: DNA
<213> ORGANISM: Artificial Sequence
<220> FEATURE:
<223> OTHER INFORMATION: MURF1 probe

<400> SEQUENCE: 31
ctgttttcct tggtcactcg                                                  20

<210> SEQ ID NO 32
<211> LENGTH: 25
<212> TYPE: DNA
<213> ORGANISM: Artificial Sequence
<220> FEATURE:
<223> OTHER INFORMATION: 18s forward primer

<400> SEQUENCE: 32
cgcagctagg aataatggaa tagga                                            25

<210> SEQ ID NO 33
<211> LENGTH: 21
<212> TYPE: DNA
<213> ORGANISM: Artificial Sequence
<220> FEATURE:
<223> OTHER INFORMATION: 18s reverse primer
```

```
<400> SEQUENCE: 33
ggcctcagtt ccgaaaacca a                                          21

<210> SEQ ID NO 34
<211> LENGTH: 16
<212> TYPE: DNA
<213> ORGANISM: Artificial Sequence
<220> FEATURE:
<223> OTHER INFORMATION: 18s probe

<400> SEQUENCE: 34
ccgcggttct attttg                                                16

<210> SEQ ID NO 35
<211> LENGTH: 25
<212> TYPE: DNA
<213> ORGANISM: Artificial Sequence
<220> FEATURE:
<223> OTHER INFORMATION: pGL3-230 forward primer

<400> SEQUENCE: 35
ggtaccccaa agcctctcat gacac                                      25

<210> SEQ ID NO 36
<211> LENGTH: 27
<212> TYPE: DNA
<213> ORGANISM: Artificial Sequence
<220> FEATURE:
<223> OTHER INFORMATION: pGL3-239 forward primer

<400> SEQUENCE: 36
gaaagaggaa taagatatgg tcaagtc                                    27

<210> SEQ ID NO 37
<211> LENGTH: 26
<212> TYPE: DNA
<213> ORGANISM: Artificial Sequence
<220> FEATURE:
<223> OTHER INFORMATION: pGL3-22 forward primer

<400> SEQUENCE: 37
cacatgccca tcatatgact gtgaag                                     26

<210> SEQ ID NO 38
<211> LENGTH: 27
<212> TYPE: DNA
<213> ORGANISM: Artificial Sequence
<220> FEATURE:
<223> OTHER INFORMATION: pGL3-22 reverse primer

<400> SEQUENCE: 38
gaaagaggaa taagatatgg tcaagtc                                    27

<210> SEQ ID NO 39
<211> LENGTH: 26
<212> TYPE: DNA
<213> ORGANISM: Artificial Sequence
<220> FEATURE:
<223> OTHER INFORMATION: pGL3-32 forward primer

<400> SEQUENCE: 39
gggcacatag tagagctcac aaaatg                                     26

<210> SEQ ID NO 40
<211> LENGTH: 27
```

-continued

```
<212> TYPE: DNA
<213> ORGANISM: Artificial Sequence
<220> FEATURE:
<223> OTHER INFORMATION: pGL3-32 reverse primer

<400> SEQUENCE: 40
tgagtcttct gtgtggttaa tacattg                                           27

<210> SEQ ID NO 41
<211> LENGTH: 24
<212> TYPE: DNA
<213> ORGANISM: Artificial Sequence
<220> FEATURE:
<223> OTHER INFORMATION: pGL3-13a forward primer

<400> SEQUENCE: 41
catagtgcac cattgacaca acat                                              24

<210> SEQ ID NO 42
<211> LENGTH: 27
<212> TYPE: DNA
<213> ORGANISM: Artificial Sequence
<220> FEATURE:
<223> OTHER INFORMATION: pGL3-13a reverse primer

<400> SEQUENCE: 42
tgagtcttct gtgtggttaa tacattg                                           27

<210> SEQ ID NO 43
<211> LENGTH: 24
<212> TYPE: DNA
<213> ORGANISM: Artificial Sequence
<220> FEATURE:
<223> OTHER INFORMATION: pGL3-25a forward primer

<400> SEQUENCE: 43
catagtgcac cattgacaca acat                                              24

<210> SEQ ID NO 44
<211> LENGTH: 27
<212> TYPE: DNA
<213> ORGANISM: Artificial Sequence
<220> FEATURE:
<223> OTHER INFORMATION: pGL3-25a reverse primer

<400> SEQUENCE: 44
tgagtcttct gtgtggttaa tacattg                                           27
```

SCREENING TOOLS FOR DISCOVERY OF NOVEL ANABOLIC AGENTS

CROSS REFERENCE TO RELATED APPLICATION

This application claims benefit of U.S. provisional application No. 60/644,345, filed Jan. 13, 2005, the specification of which is incorporated herein in its entirety for all purposes.

ACKNOWLEDGMENT OF GOVERNMENT SUPPORT

This invention was funded by a Center of Excellence Award from VA RR&D. The government has certain rights in this invention.

FIELD

This disclosure relates to the field of muscle biology. More specifically, the disclosure relates to recombinant nucleic acids and cells that are useful for identifying novel anabolic agents.

INCORPORATION-BY-REFERENCE OF MATERIAL SUBMITTED ON COMPACT DISC

A Sequence Listing is provided in electronic format only on compact discs, as permitted under 37 CFR 1.52(e) and 1.821(c). The discs (copy 1 and copy 2) contain the file entitled "Sequence Listing.txt" (12.0 KB). The material on these discs is hereby incorporated by reference in its entirety.

BACKGROUND

Muscle loss is an important medical consequence of spinal cord injury, burns, chronic illness, injury, and aging (Spungen et al., *J Appl Physiol* 88: 1310-1315, 2000; Yeh et al., *Chest* 122: 421-428, 2002; Janssen et al., *J Am Geriatr Soc* 52: 80-85, 2004). The weakness caused by muscle loss reduces mobility and independence, and increases risks of falls and fractures. Muscle loss results primarily from accelerated degradation of muscle proteins by caspases and the ubiquitin-proteasome system (Tiao et al., *J. Clin. Invest* 94: 2255-2264, 1994; Furuno et al., *J Biol Chem* 265: 8550-8557, 1990). In this system, proteins are marked by the covalent attachment of the 76 amino acid protein ubiquitin by the formation of an isopeptide bond between the carboxyl terminus of ubiquitin and the $\epsilon$-amino group of a lysine in the substrate protein (Pickart, *Annu Rev Biochem* 70: 503-533, 2001). Additional ubiquitin molecules are attached to the previously bound ubiquitin, forming a poly-ubiquitin chain that is recognized by the 26S proteasome. This giant protease complex then degrades the substrate.

Conjugation of ubiquitin to appropriate substrate proteins is catalyzed by E3s (ubiquitin ligases) (Pickart, *Annu Rev Biochem* 70: 503-533, 2001). The most common form of this ligase is a multimeric complex that includes an E2 (ubiquitin conjugase), one or more proteins providing substrate recognition, and structural proteins. DNA microarray analysis and differential display studies have shown that a gene called Muscle Atrophy F-Box (MAFbx) is greatly upregulated in muscle loss states (Gomes et al., *Proc Natl Acad Sci USA* 98: 14440-14445, 2001; Bodine et al., *Science* 294: 1704-1708, 2001; Lecker et al., *Faseb J* 18: 39-51, 2004). F-Box proteins such as MAFbx are components of SCF (Skp-cullin-F-box) family ubiquitin ligases and may serve important roles in recognizing the substrates for ubiquitination by such complexes. The MAFbx gene is expressed selectively in skeletal muscle and heart suggesting very specific functions in the biology of these tissues (Bodine et al., *Science* 294: 1704-1708, 2001). Moreover, disruption of the MAFbx gene in mice greatly reduces rates of muscle loss (Bodine et al., *Science* 294: 1704-1708, 2001). The MAFbx gene is upregulated in all muscle loss states studied to date, including paralysis, starvation, diabetes, renal failure, sepsis, and glucocorticoid excess (Gomes et al., *Proc Natl Acad Sci USA* 98: 14440-14445, 2001; Bodine et al., *Science* 294: 1704-1708, 2001; Lecker et al., *Faseb J* 18: 39-51, 2004; Wray et al., *Int J Biochem Cell Biol* 35: 698-705, 2003). Consequently, understanding the regulation of MAFbx expression has been of great interest.

Little is known about how expression of this gene is controlled. Muscle specific expression of many other genes is accomplished through muscle differentiation factors such as myogenin and MyoD acting at regulatory elements in promoter regions of such genes (Rawls and Olson, *Cell* 89: 5-8, 1997). These are transcription factors expressed early in the program of muscle differentiation that continue to be expressed in fully differentiated muscle. Such elements have been found in upstream regulatory regions, in non-coding sequences within the first exon, and in introns (Catala et al., *Mol Cell Biol* 15: 4585-4596, 1995; Storbeck et al., *J Biol Chem* 273: 9139-9147, 1998; Wheeler et al., *Am J Physiol* 276: C1069-C1078, 1999; Smith et al., *Am J Physiol* 274: C1188-C1195, discussion C1187, 1998; Cheng et al., *Endocrinology* 143: 4693-4701, 2002; Gilley et al., *J Cell Biol* 162: 613-622, 2003). Core promoters or their immediate upstream regions also confer tissue selectivity (Smith et al., *Am J Physiol* 274: C1188-C1195, discussion C1187, 1998). Some insight into how MAFbx expression is upregulated in muscle loss states comes from findings that the forkhead family transcription factor Foxo3A is activated in muscle loss states such as starvation and glucocorticoid toxicity, and that in the mouse MAFbx gene this transcription factor upregulates MAFbx expression by interactions with forkhead transcription factor elements within the upstream promoter and untranslated region of the first exon (Stitt et al., *Mol Cell* 14: 395-403, 2004; Lee et al., *J Am Soc Nephrol* 15: 1537-1545, 2004).

The following disclosure elucidates structural and functional attributes of the human MAFbx transcription regulatory sequence, and provides useful compositions and methods based thereon.

SUMMARY

The disclosure provides recombinant nucleic acids that include transcription regulatory sequences derived from the human MAFbx gene. In certain embodiments, the nucleic acids include a reporter operably linked to a human MAFbx transcription regulatory sequence. Cells into which such nucleic acids have been introduced are also a feature of this disclosure. Kits and/or cells including such nucleic acids are also disclosed, as are recombinant nucleic acids that include an expressible polynucleotide sequence (such as an ORF that encodes a polypeptide, an siRNA or a ribozyme) operably linked to a human MAFbx transcription regulatory sequence.

Methods for identifying agents that inhibit (reduce or attenuate) muscle loss are a feature of this disclosure. For example, a population of cells that includes a nucleic acid that encodes a reporter operably linked to a human MAFbx transcription regulatory sequence is contacted with a test agent. A decrease in the reporter following contact of the cells with a test agent indicates that the agent inhibits muscle loss.

Optionally, the methods also involve identifying an agent that increases muscle mass and/or muscle tone by detecting an increase in a reporter operably linked to an IGF-1 transcription regulatory sequence. Such methods are also suitable for identifying an agent that both inhibits muscle loss and increases muscle mass, or agents that selectively inhibit muscle loss or increase muscle mass.

BRIEF DESCRIPTION OF THE FIGURES

FIG. 1A is an image of a Northern blot and FIG. 1B is a bar graph illustrating that expression of MAFbx depends on cell lineage. (A) Total RNA was used to assess MAFbx expression by Northern blotting. (B) Cells were seeded into wells of 24-well plates ($5 \times 10^4$). After incubation overnight, cells were transfected with pMAF948 and pCMV-Renilla. After 3 h, 0.8 ml of growth medium containing 10% CDS was added. Twenty four hours later, luciferase activity was measured. Values were normalized relative to those for L6 cells. Data are mean values±SEM for at least 3 experiments.

FIG. 2A is an image of a Northern blot and FIG. 2B is a bar graph illustrating induction of MAFbx expression during differentiation of C2C12 cells. (A) Cells were seeded into 100 mm plates, grown until 80% confluent, then maintained in growth medium (DMEM supplemented with 10% FBS) or differentiation medium (DMEM supplemented with 2% horse serum) for the indicated periods at which time MAFbx mRNA levels were quantified by Northern blotting. (B) Cells at 80-95% confluence were transfected overnight with pMAF948 and CMV-Renilla then maintained for 24 hours in media (undifferentiated cells, DMEM+10% FBS, differentiated cells, DMEM+2% HS), at which time luciferase activity was quantified. Differentiation was induced by incubation for 48 hours in DMEM supplemented with 2% horse serum. Data are means±SEM for 6 replicates from a representative experiment.

FIG. 5 is a sequence alignment of the first 1 kb upstream of the ATG for mouse, rat and human MAFbx genes. Forkhead binding sites are marked with a double underline. A conserved E-Box is shown as a bold underline. The transcriptional start site is bolded with a single underline. Sequence alignments were performed using the ClustalW function of Biology Workbench 3.2 (on the world wide web at seqtool.sdsc.edu/CGI/GW.cgi).

FIGS. 7A and B are bar graphs illustrating reduction of MAFbx promoter activity by testosterone. (A) Cells were co-transfected with pMAF3.1 and pRL-CMV then incubated overnight with testosterone at the indicated concentrations, or vehicle (EtOH). Data are normalized relative to values for cells incubated with EtOH and are mean values±SEM for 3 different experiments each in at least triplicate. *$p<0.05$ vs EtOH (t-test). (B) Sequences in the 5' UTR are necessary for effect of testosterone to suppress MAFbx expression. The left panel schematically illustrates the reporter genes used. Luc, luciferase; UTR, untranslated region. The right panel is a bar graph illustrating reporter activity in C2C12.AR cells transfected with the indicated reporter genes and pRL-CMV then incubated overnight with either EtOH or testosterone (500 nM). Data are normalized relative to values for cells transfected with pMAF3.1 and incubated with EtOH and are mean values±SEM for 3 different experiments each performed in at least triplicate. * $p<0.05$ vs EtOH for the same reporter gene (t-test).

FIG. 8 is a bar graph and accompanying schematic illustration of constructs demonstrating that suppression of MAFbx promoter activity by testosterone does not require DNA binding. Upper Panel: C2C12 wild-type cells were co-transfected with pMAF3.1, pRL-CMV, and a vector expressing either wild-type hAR, or an AR mutant, as indicated in the figure, then incubated overnight with vehicle (EtOH) or testosterone (500 nM). Data are mean values±SEM for three experiments each performed in at least triplicate. * $p<0.05$ vs EtOH, t-test. Lower Panel: Overview of mutants used; TAD, transactivating domain, DBD, DNA binding domain, NLS, nuclear localization signal, LBD, ligand binding domain.

FIGS. 10A and B are bar graphs illustrating activation of the MAFbx promoter by dexamethasone is blocked by testosterone. (A) C2C12.AR cells were transfected with pMAF3.1 and pRL-CMV then incubated overnight with hormone or vehicle (EtOH). Data are luciferase activities normalized relative to vehicle only and are mean values for 3 experiments each performed in at least triplicate. * p<0.05 vs. EtOH, t-test. (B) Wild-type C2C12 cells were transfected MAFbx reporter genes and pRL-CMV, then incubated overnight with hormones as indicated in the figure. Data are mean values±SEM for luciferase expression from a representative experiment with six replicates. * p<0.05 vs EtOH, § p<0.05 vs Dex 100 nM, \ p>0.05 vs EtOH (ANOVA).

Figure 11:
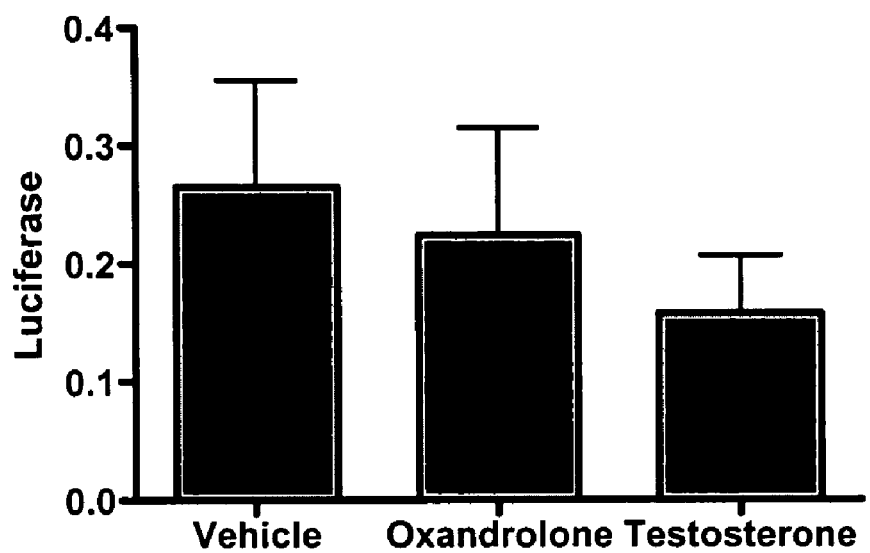

FIG. 11 is a bar graph illustrating differential regulation of the MAFbx promoter by testosterone and oxandrolone.

Figure 12:
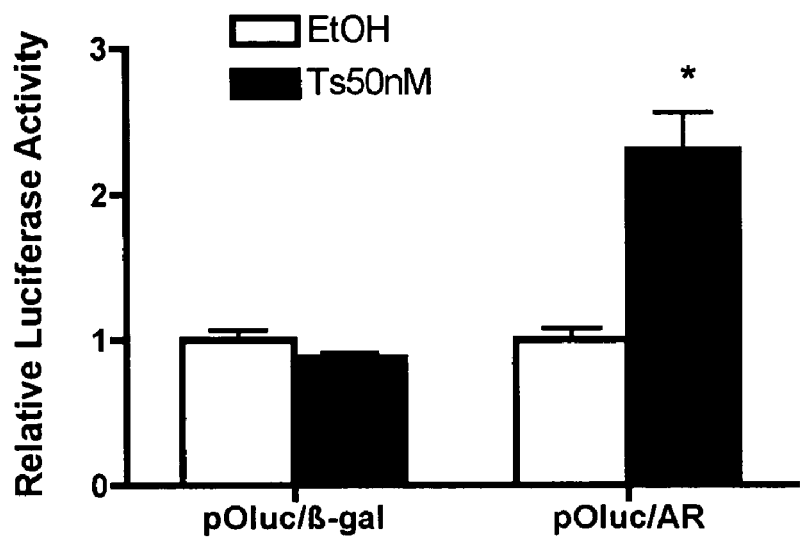

FIG. 12 is a bar graph illustrating testosterone responsiveness of the human IGF-1 promoter. HepG2 cells were co-transfected with pOLuc-1630, pCMV-Renilla, and vectors expressing either β-galactosidase or AR. Cells were incubated overnight with testosterone (TS) or vehicle, then assayed for luciferase. Data are mean values±SEM for YZ experiments.

Figure 13:
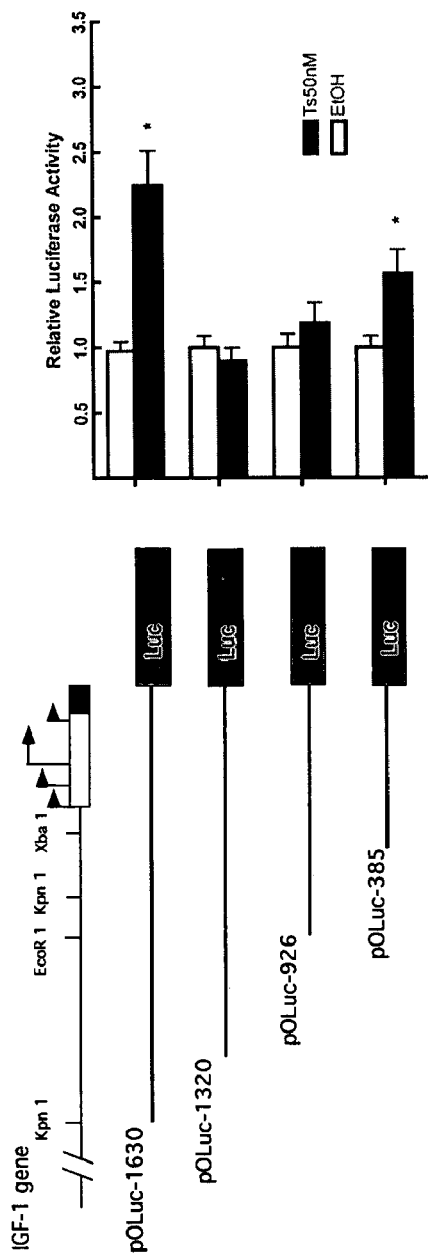

FIG. 13 is a bar graph demonstrating ablation of androgen responsiveness by 5' truncation of the promoter region accompanied by a schematic illustration showing the promoter constructs. Left: map of IGF-1 gene and constructs used. Arrows indicate the approximate location of the four transcriptional start sites within exon 1. Right: HepG2 cells were co-transfected with pOLuc-1630, derivatives having 5' truncations of the 1630 bp IGF-1 promoter insert, together with pCMV-Renilla and a vector expressing. AR. After incubation overnight with testosterone (TS) or vehicle, luciferase activities were determined. Data are mean values±SEM for at least 3 experiments, each having 3 replicates.

Figure 14:
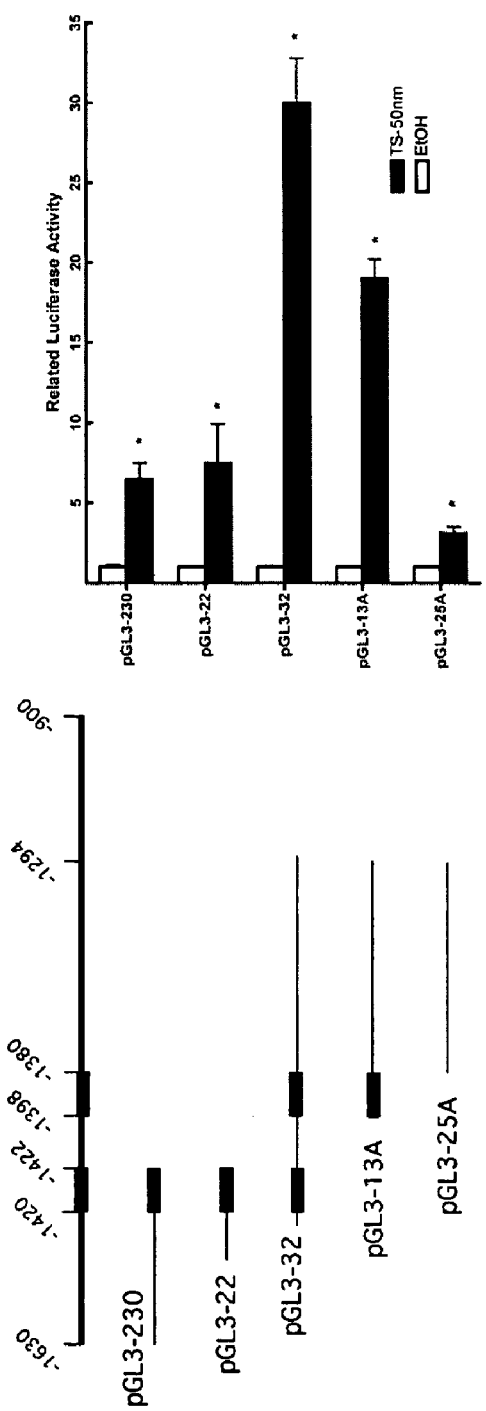

FIG. 14 is a bar graph illustrating androgen-responsiveness of promoter regions containing putative IGF-1 AREs accompanied by a schematic illustration of the promoter constructs. Left panel: map of reporter constructs tested. Rectangles indicate the approximate position of putative androgen response elements in the human IGF-1 promoter. Right panel: HepG2 cells were co-transfected with the indicated reporter constructs together with pCMV-*Renilla* and a vector expressing AR, then incubated overnight with testosterone (TS) or vehicle. Luciferase activities were determined. Data are means±SEM for at least 3 different experiments.

Figure 15:
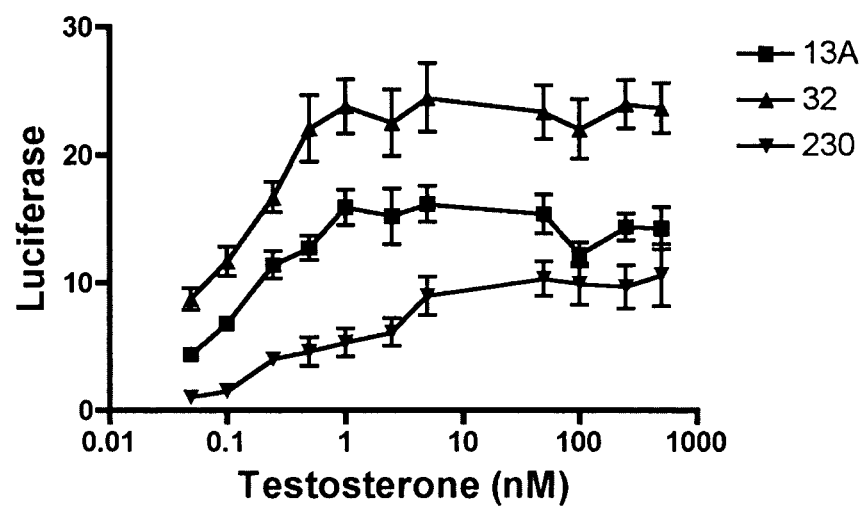

FIG. 15 is a line graph demonstrating synergism between IGF-1 AREs. Cells were co-transfected with the indicated reporter genes, pRL-CMV, and a vector expressing AR, then incubated with testosterone at the indicated concentrations, or with EtOH. Data are mean values±SEM for 3 different experiments each with at least two replicates.

FIG. 16A is a set of bar graphs and FIG. 16B is an image of non-denaturing gel demonstrating that mutation of the AR DBD disrupts transactivation via IGF-1 AREs. (A) Cells were co-transfected with a vector expressing mutant AR unable to bind DNA (pC562G) or wild-type AR together with the indicated reporter gene, and pRL-CMV, then incubated overnight with testosterone (50 nM) or EtOH. Data are mean values±SEM for three separate experiments each performed in at least duplicate. (B) The AR binds to ARE1 and ARE2. An AR-DBD-GTS fusion protein was incubated with P[32]-labeled oligonucleotides probes having sequences of either ARE1 or ARE2 in the absence or presence of unlabeled probe with a sequence of the consensus steroid hormone receptor element (SRE) then resolved by non-denaturing electrophoresis.

Figure 17:
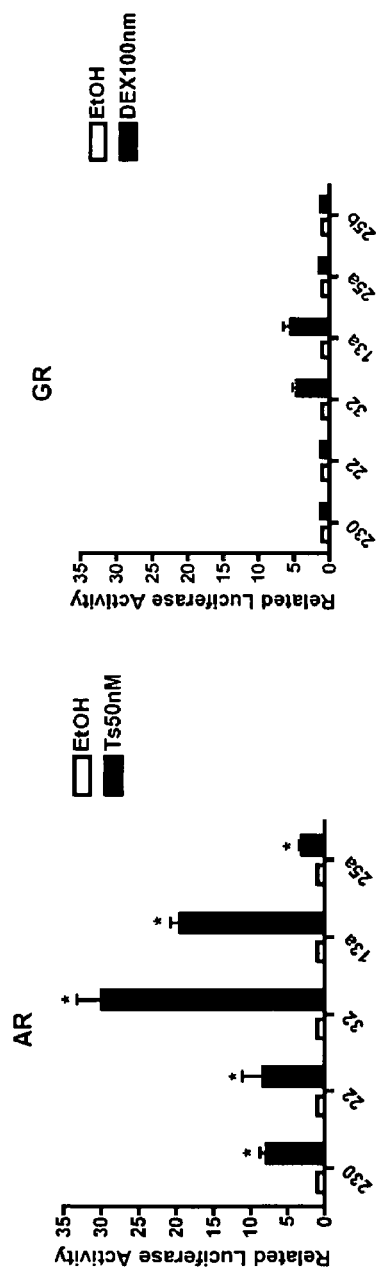

FIG. 17 is a pair of bar graphs comparing transactivation at ARE1 and ARE2 by AR and GR. Cells were co-transfected with the indicated reporter genes, pCMV-Renilla, and a vector expressing either AR or GR, then incubated overnight with hormone as indicated in the figure. Data are mean values±SEM for three separate experiments, each performed in at least duplicate.

Figure 18:
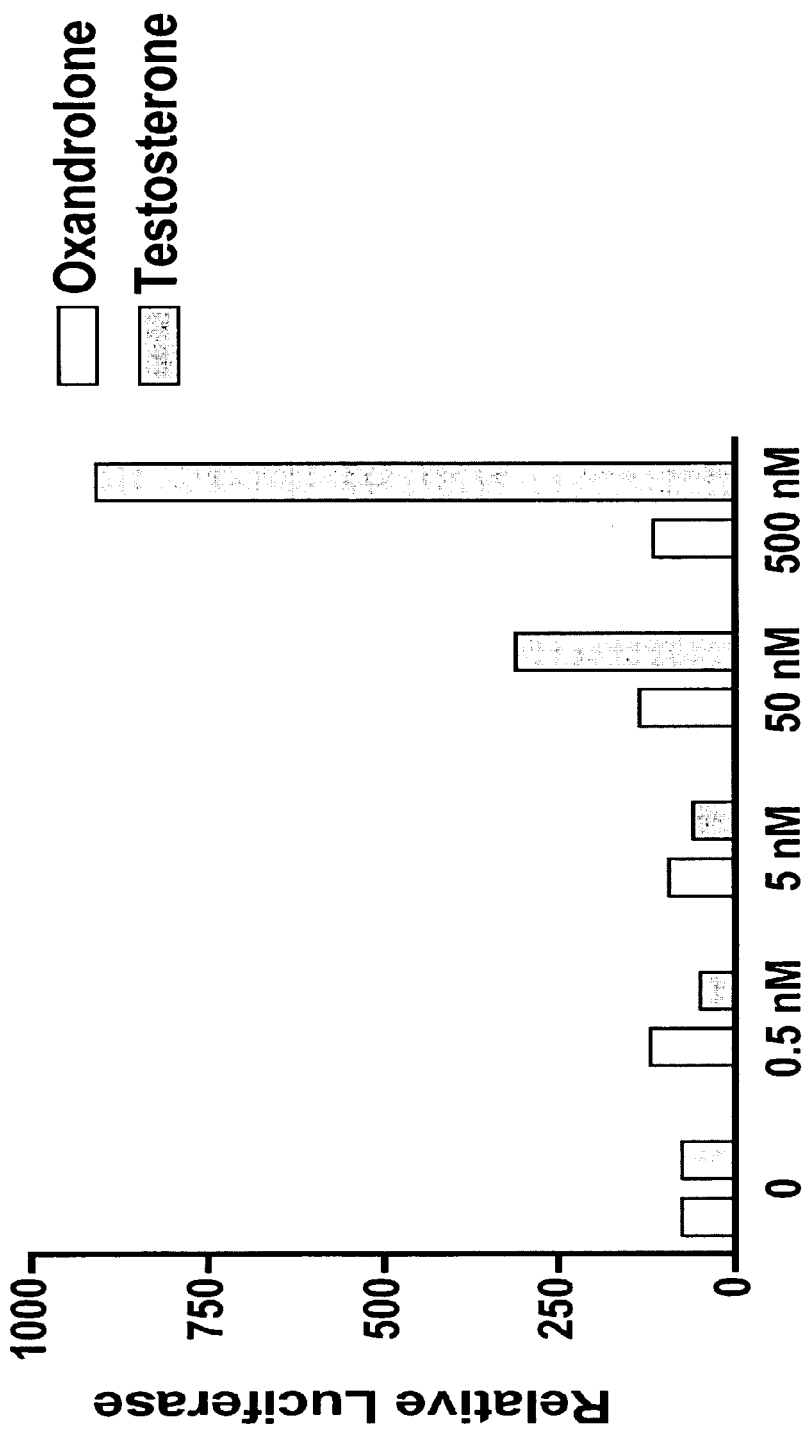

FIG. 18 is a bar graph illustrating that the upstream promoter of the human IGF-1 gene is activated by testosterone in Hep G2 cells, but not by oxandrolone. Data are means of duplicate determinations from a representative experiment.

Figure 19:
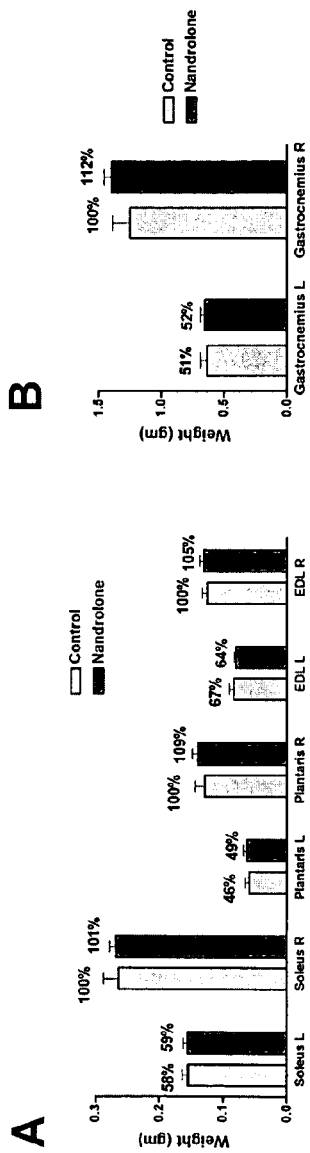

FIGS. 19A and B are bar graphs illustrating the effects of nandrolone on muscle loss after 14 days denervation. Values above each bar represent the weights of the muscles from the denervated leg expressed as a percentage relative to weights for the same muscle from the sham-denervated leg of animals treated with placebo (Control). Data are for 6 control and 5 nandrolone animals.

Figure 20:
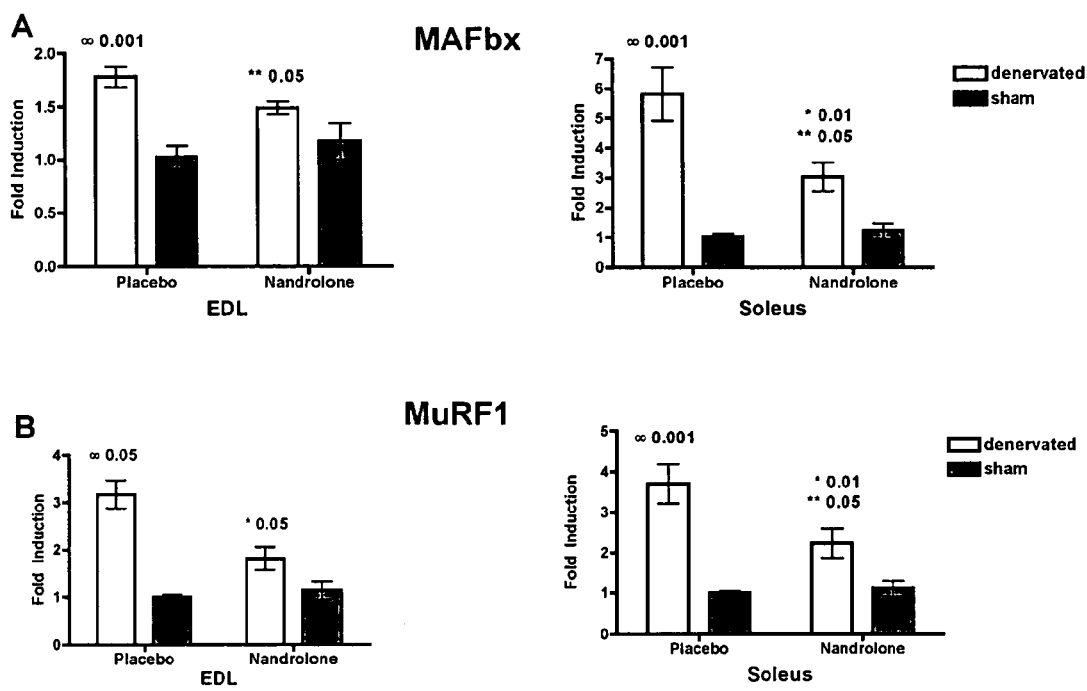

FIGS. 20A and B are bar graphs illustrating that Nandrolone reduced expression of ubiquitin ligases in denervated muscle. (A) mRNA levels in denervated muscle for MAFbx and (B) MuRF1 are expressed relative to levels in normal muscle from the sham-transected leg of animals administered placebo. Data are means for 6 animals±SEM. Data are for 6 control and 5 nandrolone animals. * versus denervated muscle from animals administered vehicle; ** and ∞, versus sham placebo.

Figure 21:
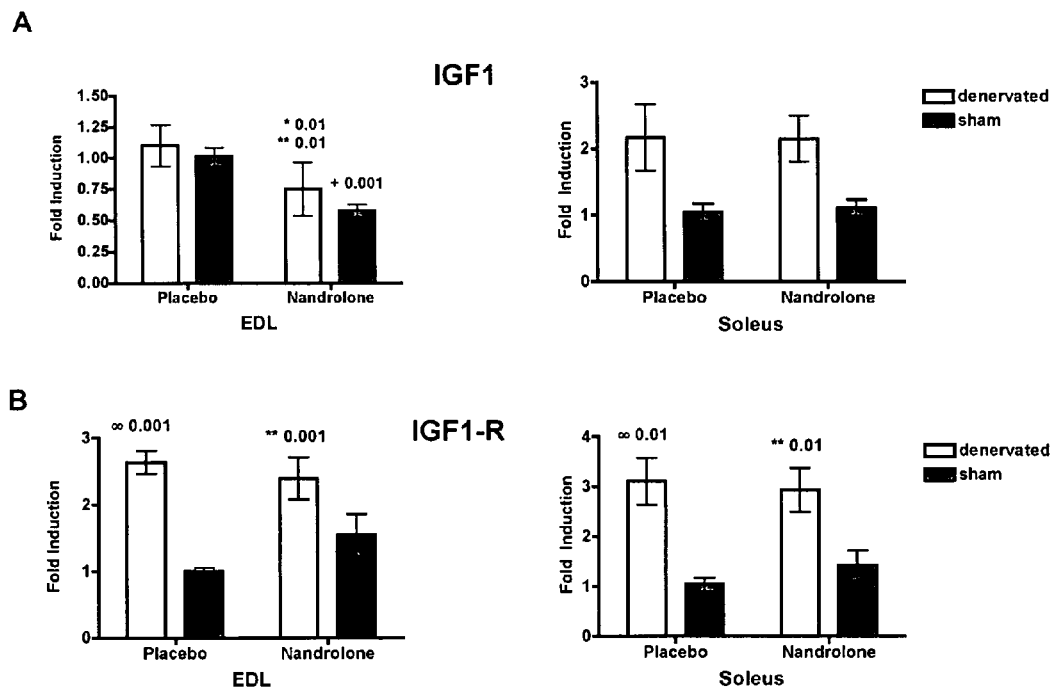

FIGS. 21A and B are bar graphs illustrating the effects of nandrolone on expression of IGF-1 and its receptor in denervated muscle. Levels in denervated muscle of mRNA for (A) IGF-1 and (B) IGF-1R are expressed relative to levels in normal muscle from the sham-transected leg of animals administered placebo. Data are for 6 control and 5 nandrolone animals. * versus denervated muscle from animals administered vehicle; **, ∞ versus sham placebo.

Figure 22:
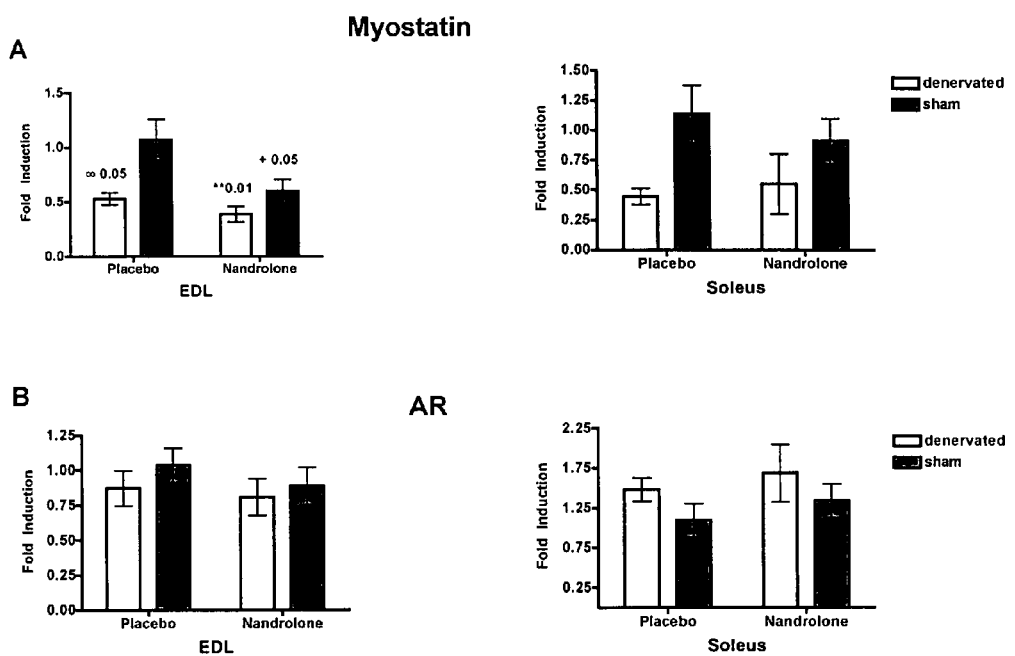

FIGS. 22A and B are bar graphs illustrating the effects of nandrolone on expression of myostatin and AR in denervated muscle. mRNA levels in denervated muscle for (A) myostatin and (B) androgen receptor are expressed relative to levels in normal muscle from the sham-transected leg of animals administered placebo. Data are for 6 control and 5 nandrolone animals. **, ∞, + versus sham placebo.

FIGS. 23A-C are bar graphs illustrating the effects of nandrolone on mRNA levels for junB, myogenin and GADD45 in denervated muscle. mRNA levels in denervated muscle for (A) junB, (B) myogenin, and (C) GADD45 are expressed relative to levels in normal muscle from the sham-transected leg of animals administered placebo. Data are for 6 control and 5 nandrolone animals. * versus denervated muscle from animals administered vehicle; **, ∞ versus sham placebo.

Figure 24:
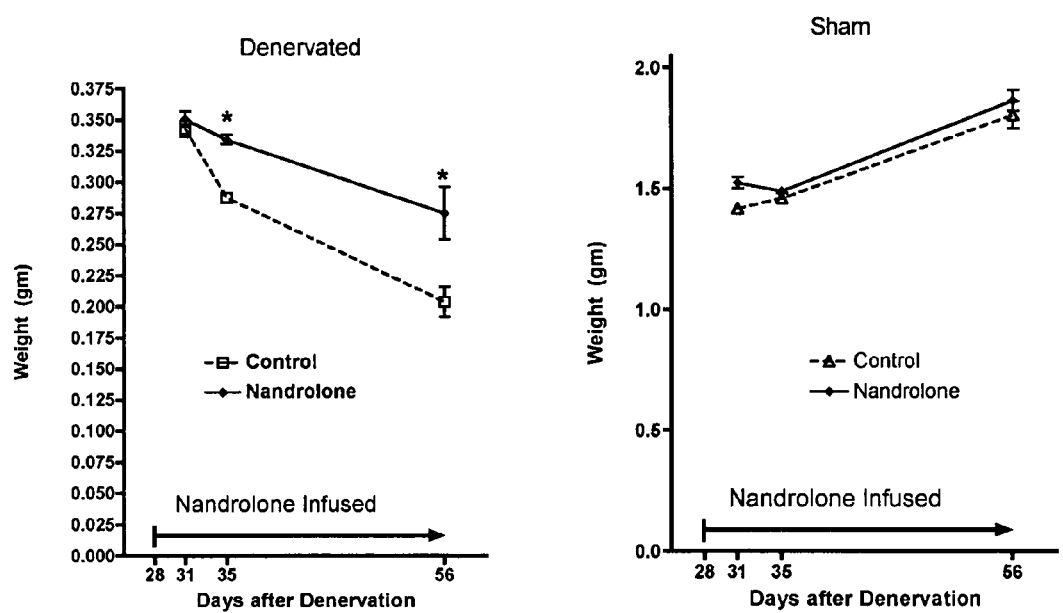

FIG. 24 is a pair of line graphs showing the effects of nandrolone on muscle weight after denervation (left panel) or sham denervation (right panel). Animals underwent denervation and sham denervation on day 0, followed by infusion of nandrolone plus testosterone, or vehicle, beginning on day 28. Animals were sacrificed 3, 7 or 28 days after starting infusion of drug or vehicle, corresponding to 31, 35 or 56 days after denervation, respectively. Mean values±SEM are shown for gastrocnemius weights. N≧8; *p≦0.05, t-test.

Figure 25:
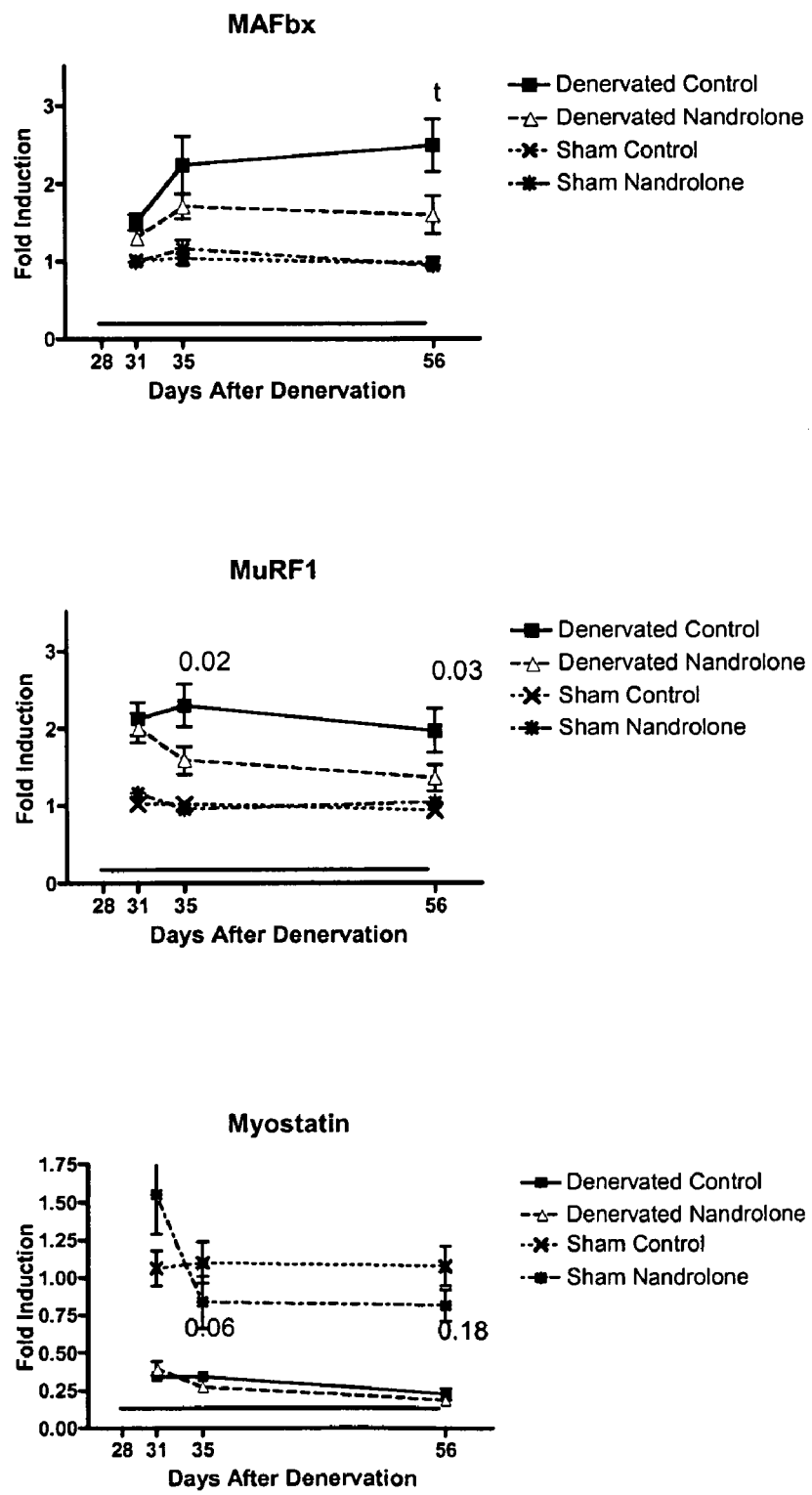

FIG. 25 is a set of line graphs illustrating the effects of nandrolone on expression of factors driving muscle atrophy. Levels of mRNA as determined by qPCR are shown as means±SEM for at least 5 animals. For MAFbx, t, p<0.05 vs denervated vehicle, t-test. Values above points indicate p values versus denervated vehicle at the same time point (ANOVA).

Figure 26:
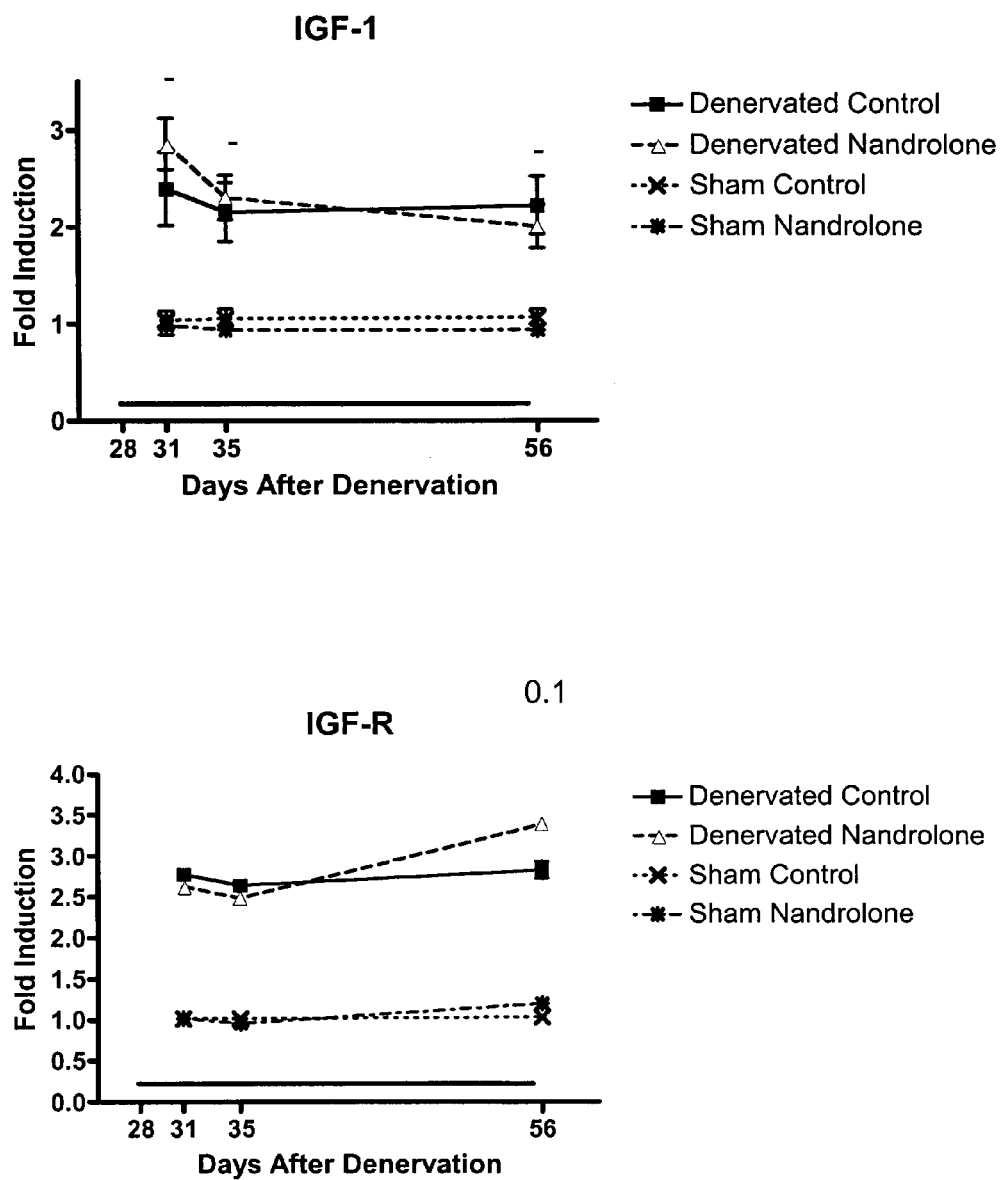

FIG. 26 is a pair of line graphs illustrating the effects of nandrolone on expression of IGF-1 and its receptor. Levels of mRNA as determined by qPCR are shown as means±SEM for at least 5 animals. Minus sign, not different from denervated vehicle. Values above points indicate p values versus denervated vehicle at the same time point (ANOVA).

Figure 27:
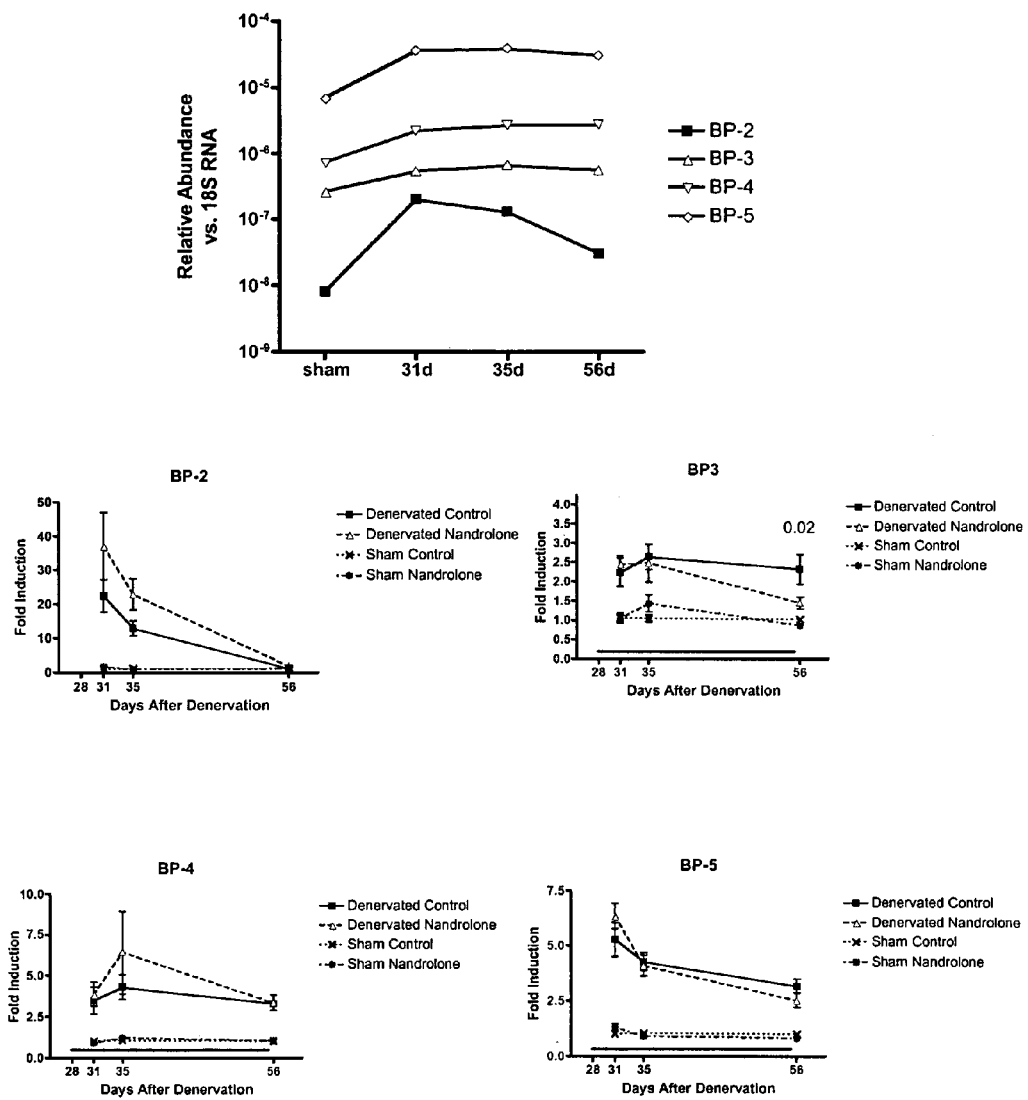

FIG. 27 is a set of line graphs showing the effects of nandrolone on expression of IGFBPs. Top panel: relative abundance as compared to 18S RNA of mRNA for different IGFBPs in innervated gastrocnemius muscle from animals given vehicle. Remaining panels: Effects on nandrolone on expression of IGFBPs in gastrocnemius muscle. Levels of mRNA as determined by qPCR are shown as means±SEM for at least 5 animals. Minus sign, not different from denervated vehicle. Values above points indicate p values versus denervated vehicle at the same time point (ANOVA).

Figure 28:
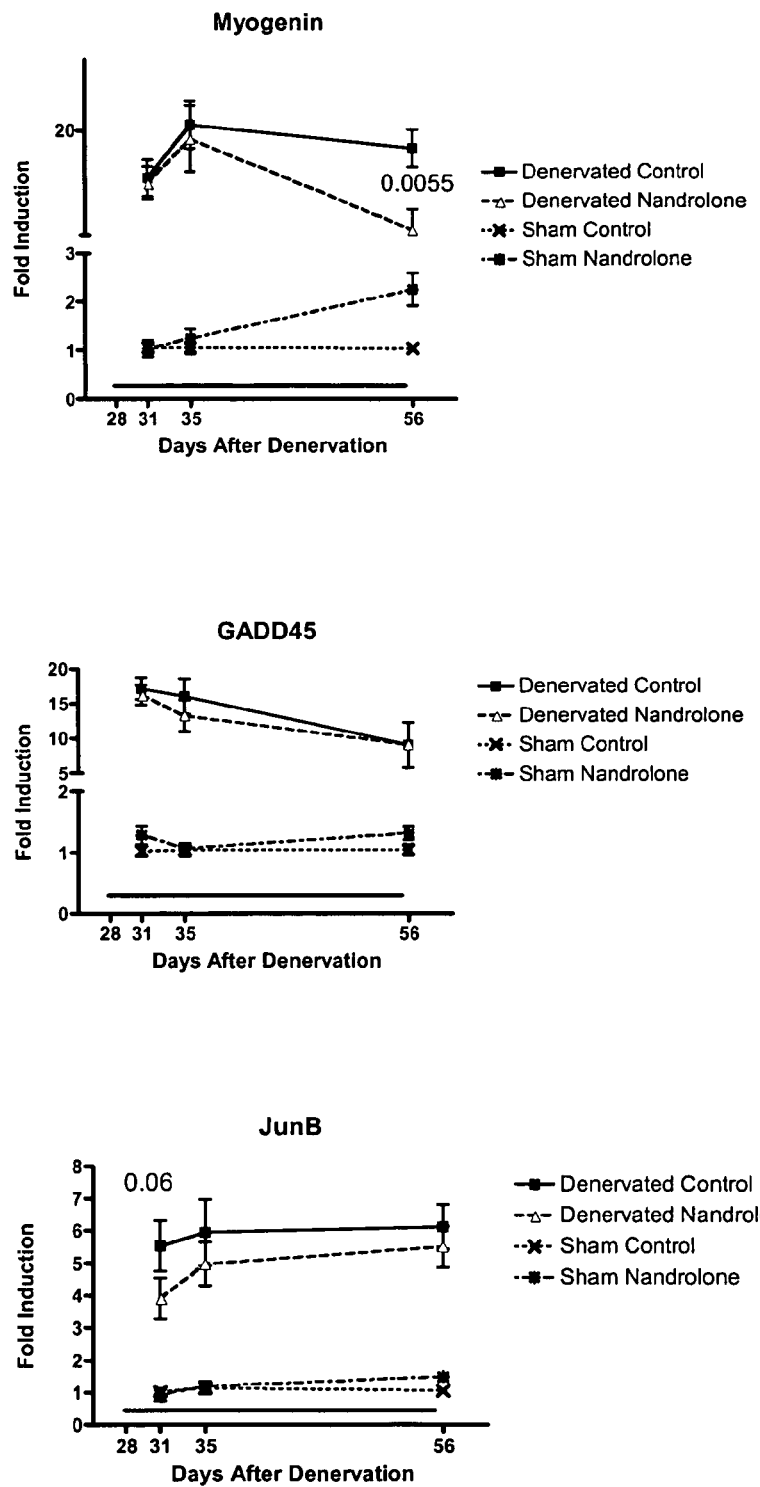

FIG. 28 is a set of line graphs illustrating the effects of nandrolone on selected regulators of transcription. Levels of mRNA as determined by qPCR are shown as means±SEM for at least 5 animals. Minus sign, not different from denervated vehicle. Values above points indicate p values versus denervated vehicle at the same time point (ANOVA).

DESCRIPTION OF THE SEQUENCE LISTING

SEQ ID NO:1 is the polynucleotide sequence of the core transcription regulatory sequence extending from positions −241 through −411 with respect to the translation start site of the human MAFbx genomic sequence.

SEQ ID NO:2 is the polynucleotide sequence of positions −1 through −411 with respect to the translation start site of the human MAFbx genomic sequence.

SEQ ID NO:3 is the polynucleotide sequence of positions −1 through −900 with respect to the translation start site of the human MAFbx genomic sequence.

SEQ ID NO:4 is the polynucleotide sequence of the region upstream of the rat MAFbx gene.

SEQ ID NO:5 is the polynucleotide sequence of the region upstream of the mouse MAFbx gene.

SEQ ID NO:6 is the polynucleotide sequence of the region upstream of the human MAFbx gene.

SEQ ID NOs:7-11 are primers for amplifying segments of the region upstream of the human MAFbx gene.

SEQ ID NOs:12 and 13 are primers for amplifying the full length human MAFbx cDNA.

SEQ ID NO:14 is a primer for primer extension analysis.

SEQ ID NOs:15-16 are the forward and reverse primers for TAQMAN® On Demand.

SEQ ID NO:17 is the labeled probe for TAQMAN® On Demand Assay.

SEQ ID NOs:18-22 are the polynucleotide sequences of androgen response elements (AREs).

SEQ ID NOs:23-25 are oligonucleotide probes for detecting ARE2, ARE1 and SRE by electrophoretic mobility shift assay, respectively.

SEQ ID NOs:26-28 are forward and reverse primers and probe, respectively, for real time PCR of myostatin.

SEQ ID NOs:29-31 are forward and reverse primers and probe, respectively, for real time PCR of MuRF1.

SEQ ID NOs:32-34 are forward and reverse primers and probe, respectively, for real time PCR of 18S RNA.

SEQ ID NOs:35-44 are oligonucleotide primers for amplification of the human IGF-1 upstream promoter.

DETAILED DESCRIPTION

Muscle loss is linked to increased expression of a ubiquitin ligase termed Muscle Atrophy F-box (MAFbx). In the mouse, increases in MAFbx expression are associated with the transcription factor Foxo3A acting at forkhead elements in the MAFbx promoter. To elucidate the factors that regulate the human MAFbx gene, the expression of this gene in cultured cells and structure of its upstream promoter were determined. Analysis of cultured cells revealed MAFbx expression only in cells of muscle lineage. A reporter gene controlled by 948 bases of human MAFbx upstream promoter displayed similar cell-type selectivity. MAFbx levels were greatly enhanced upon myogenic differentiation of the C2C12 myoblast line, a finding mirrored by induction of activity of reporter genes constructed with 400 bp of upstream promoter (SEQ ID NO:2) from the MAFbx gene. Truncation analysis indicated that the core promoter (SEQ ID NO:1) spanned approximately 170 bases beginning at −235 bp upstream of the first codon.

The core promoter was highly conserved among mouse, rat and human MAFbx genes. The major transcription start site for the human MAFbx gene was 341 bases upstream of the ATG and was localized the highly conserved region of 140 bp. The findings indicate an important role for the immediate upstream promoter of the human MAFbx gene in mediating its developmental expression and tissue specificity.

The present disclosure provides nucleic acids, and useful compositions and methods based on the favorable properties of the human MAFbx transcription regulatory sequences. In one embodiment, the disclosure provides a recombinant nucleic acid including a polynucleotide sequence encoding a reporter operably linked to a transcription regulatory sequence derived from the human MAFbx gene. The transcription regulatory region typically includes a polynucleotide sequence at least 95% identical to the human MAFbx core promoter, and optionally also contains additional expression control sequences. For example, the nucleic acid can include a MAFbx core transcription regulatory sequence with the polynucleotide sequence represented by SEQ ID NO:1. Alternatively, the nucleic acid can include a transcription regulatory sequence including additional expression control elements, such as that represented by SEQ ID NO:2 or SEQ ID NO:3.

The reporter can be any directly or indirectly detectable molecule. Typically, the reporter can be detected optically as a visible, e.g., fluorescent product or by its ability to generate a visible or otherwise detectable product. Suitable reporters include green fluorescent protein and its variants ("GFP"), beta-galactosidase, beta-glucuronidase and luciferase, as well as selectable markers, such as antibiotic resistance.

Typically, the nucleic acid is a vector such as a plasmid. The nucleic acid, for example the vector, can be introduced into cells where it can be expressed. Such host cells can also include a second recombinant nucleic acid such as a nucleic acid that includes a polynucleotide sequence encoding a reporter operably linked to an Insulin-like Growth Factor I ("IGF-1") transcription regulatory region.

The reporter constructs disclosed herein are particularly useful in screening assays for identifying novel anabolic agents that increase muscle mass and/or tone, and decrease muscle loss. For example, it is disclosed herein that the reporter constructs including the human MAFbx core promoter sequence can be used to distinguish between classes of anabolic agents that have differential effects on muscle growth and loss. Expression of the human MAFbx reporters described herein are suppressed by agents, like testosterone, that suppress expression of muscle loss genes. In contrast, anabolic agents, such as oxandrolone that do not prevent muscle loss do not suppress expression of the human MAFbx reporters. Thus, the reporters described herein are uniquely suitable for detecting agents that specifically inhibit muscle loss. Optionally, the human MAFbx-reporters are utilized in combination with IGF-1-reporters to identify agents that increase muscle growth as well as decrease muscle loss.

In another embodiment, the disclosure provides a recombinant nucleic acid including a polynucleotide sequence operably linked to a human MAFbx transcription regulatory sequence, wherein the human MAFbx transcription regulatory sequence regulates muscle selective expression of the operably linked polynucleotide. Such a polynucleotide can include an open reading frame ("ORF") encoding a polypeptide. In some cases it may be desirable to express the polypeptide selectively during myogenesis or in muscle cells to achieve a beneficial effect, such as increased muscle mass, or a reduced rate of muscle wasting.

Typically, the MAFbx transcription regulatory sequence includes a polynucleotide sequence that is at least 95% identical to the human MAFbx core transcription regulatory sequence. For example, the MAFbx core transcription regulatory sequence is represented by SEQ ID NO:1. Alternatively, the transcription regulatory sequence can include additional expression control elements, such as found in SEQ ID NO:2 and SEQ ID NO:3.

Also disclosed are kits including the nucleic acids, cells and reporters described herein. For example, the kit can include at least one of: a nucleic acid including a polynucleotide encoding a reporter operably linked to a transcription regulatory sequence with a polynucleotide sequence at least 95% identical to the human MAFbx core transcription regulatory sequence; and a cell including such a nucleic acid. Optionally, the kit also includes a recombinant nucleic acid including a polynucleotide encoding a reporter operably linked to an IGF-1 transcription regulatory sequence and/or a cell including such a recombinant nucleic acid. The kit can also include one or more steroids, such as testosterone, a synthetic anabolic steroid (such as a non-virulizing anabolic steroid) and a corticosteroid (e.g., a glucocorticoid, such as dexamethasone).

Also disclosed are methods for identifying an agent that promotes at least one of increased muscle mass and/or muscle tone and decreased muscle loss. Such methods involve using cells containing human MAFbx-reporters to detect differences in reporter expression resulting from contacting the cell with a test agent. Optionally, cells including an IGF-1-reporter are also contacted with the test agent. The disclosed methods possess the favorable attribute that they can preferentially identify agents that, like testosterone, inhibit muscle loss, in contrast to agents that, like oxandrolone, do not inhibit muscle loss. When methods are employed using both the human MAFbx-reporter and the IGF-1-reporter, agents can be identified that inhibit muscle loss and increase muscle growth. These agents can be distinguished from agents that promote muscle mass (e.g., without inducing expression of IGF-1), in the absence of preventing muscle loss. Agents that both promote muscle mass and inhibit muscle loss are likely be particularly beneficial for treating subjects with muscle wasting due to such conditions as aging, disuse, starvation, disease and injury.

For example, the methods for identifying agents that decrease muscle loss and/or increase muscle mass or tone involve contacting cells (that is, a plurality of cells) with at least one test agent. The cells contain a recombinant nucleic acid including a polynucleotide sequence encoding a reporter operably linked to a human MAFbx transcription regulatory sequence. Optionally, the cells can include an additional recombinant nucleic acid comprising a polynucleotide sequence encoding a reporter operably linked to an IGF-1 transcription regulatory sequence. Following contacting the cells with the agent, a decrease in expression of the reporter linked to the human MAFbx transcription regulatory sequence is detected indicating that the agent decreases muscle loss. Where the cells also include a reporter linked to the IGF-1 transcription regulatory sequence, an increase in this reporter can be detected identifying a composition that promotes increased muscle mass and/or muscle tone. In some cases both a decrease in the first reporter and an increase in the second reporter can be detected, thus identifying an agent that decreases muscle loss and increases muscle growth.

Typically, the MAFbx transcription regulatory sequence includes a polynucleotide sequence at least 95% identical to the human MAFbx core transcription regulatory sequence. For example, the transcription regulatory sequence can include the sequence represented by SEQ ID NO:1, by SEQ ID NO:2 or by SEQ ID NO:3.

The reporters can be selected from the group consisting of luciferase, GFP, beta-galactosidase, beta-glucuronidase, or another detectable marker, including a selectable marker. A first cell can include the reporter linked to the human MAFbx transcription regulatory sequence, while a second cell includes the reporter linked to the IGF-1 transcription regulatory sequence. Alternatively, the same cell can include both reporters. The reporters can be the same or different. Typically, the reporters are different reporters if they are expressed in the same cell, to facilitate detection.

In another method, agents that inhibit expression of a muscle loss gene are detected by contacting a test agent with at least one cell that includes a recombinant nucleic acid in which a polynucleotide sequence encodes a reporter operably linked to a transcription regulatory sequence. The polynucleotide sequence is at least 95% identical to the human MAFbx core transcription regulatory sequence, as described above. Following exposure to the agent, a decrease in expression of the reporter is detected, thereby identifying an agent that inhibits expression of a muscle loss gene.

Additional details concerning the aforementioned embodiments are provided below and proceed with reference to the accompanying figures. To facilitate understanding of this disclosure the following non-limiting explanations of terms are provided.

Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular*

*Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as a growth factor, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "nucleic acid" refers to a polymer of nucleotides of any length. The term includes single- and double-stranded forms of DNA (deoxyribonucleic acid) and RNA (ribonucleic acid), as well as DNA-RNA hybrids. Generally, the term "nucleic acid" is synonymous with "polynucleotide" or "polynucleotide sequence," unless clearly indicated to the contrary. The repeating units in DNA (RNA) polymers are four different nucleotides, each of which comprises one of the four bases, adenine, guanine, cytosine and thymine (uracyl) bound to a deoxyribose (ribose) sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed. Double-stranded DNA and RNA (dsDNA and dsRNA) have two strands, which can be defined with respect to the products that they encode: a 5'→3' strand, referred to as the plus or "sense" strand, and a 3'→5' strand (the reverse compliment), referred to as the minus or "antisense" strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T). Except where single strandedness is required by context, DNA molecules, although written to depict only a single strand, encompass both strands of a double-stranded DNA molecule. Accordingly, unless otherwise specified, any reference to a DNA molecule is intended to include the reverse complement of that DNA molecule.

For convenience, short polynucleotides, typically of less than about 100 nucleotides in length are often referred to as "oligonucleotides." Similarly, very short polymers of two, three, four, five, or up to about 10 nucleotides in length, can conveniently be referred to as dinucleotides, trinucleotides, tetranucleotides, pentanucleotides, etc. The nucleotides can be ribonucleotides, deoxyribonucleotides, or modified forms of either nucleotide.

A "cDNA" or "complementary DNA" is a piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

A "recombinant" polynucleotide includes a polynucleotide that is not immediately contiguous with one or both of the polynucleotide sequences with which it is immediately contiguous (one on the 5' end and one on the 3' end) in the naturally occurring genome of the organism from which it is derived. Thus, a recombinant nucleic acid can include polynucleotide sequences that are "heterologous" with respect to each other. A "heterologous" polynucleotide is a polynucleotide that is not normally (e.g., in the wild-type genomic sequence) found adjacent to a second polynucleotide sequence, or that is not normally found within a particular cell, as the reference indicates. A heterologous nucleic acid or a heterologous polynucleotide can be, but is not necessarily, transcribable and translatable. In some embodiments, a heterologous nucleic acid is a cDNA or a synthetic DNA. In other embodiments, the heterologous polynucleotide sequence is a genomic sequence that encodes an RNA transcript, such as a functional RNA molecule (e.g., an siRNA molecule or a ribozyme). In other embodiments, a heterologous polynucleotide encodes a reporter. Similarly, a recombinant protein is a protein encoded by a recombinant nucleic acid molecule. A recombinant protein can be obtained by introducing a recombinant nucleic acid molecule into a host cell (such as a eukaryotic cell or cell line, such as a mammalian cell or yeast, or a prokaryotic cell, such as bacteria) and causing the host cell to produce the gene product. Methods of causing a host cell to express a recombinant protein are well known in the art (see, e.g., Sambrook and Russell, *Molecular Cloning: A Laboratory Manual*, 3$^{rd}$ edition, New York: Cold Spring Harbor Laboratory Press, 2001).

An "isolated" biological component (such as a nucleic acid or protein) has been substantially separated or purified away from other biological components in the cell of the organism in which the component naturally occurs, such as, other chromosomal and extrachromosomal DNA and RNA, and proteins. Isolated nucleic acids and proteins include nucleic acids and proteins purified by standard purification methods. The term also embraces nucleic acids and proteins prepared by recombinant expression in a host cell as well as chemically synthesized nucleic acids.

The term "purified" refers to the removal of one or more extraneous components from a sample. The term "purified" does not require absolute purity; rather, it is intended as a relative term. For example, where recombinant polypeptides are expressed in host cells, the polypeptides are purified by, for example, the removal of host cell proteins thereby increasing the percent of recombinant polypeptides in the sample. Similarly, where a recombinant polynucleotide is present in host cells, the polynucleotide is purified by, for example, the removal of host cell polynucleotides thereby increasing the percent of recombinant polynucleotide in the sample. Isolated polypeptides or nucleic acid molecules, typically, comprise at least 50%, at least 60%, at least 70%, at least 80%, at least 90%, at least 95% or even over 99% (w/w or w/v) of a sample. Polypeptides and nucleic acid molecules are isolated by methods commonly known in the art and as described herein. Purity of polypeptides or nucleic acid molecules can be determined by a number of well-known methods, such as polyacrylamide gel electrophoresis for polypeptides, or agarose gel electrophoresis for nucleic acid molecules.

A first polynucleotide sequence is "operably linked" to a second polynucleotide sequence when the first polynucleotide is in a functional relationship with the second polynucleotide. For instance, a coding sequence is operably linked to a transcription control sequence if the transcription control sequence affects (e.g., regulates or controls) the transcription or expression of the coding sequence. When recombinantly produced, operably linked polynucleotides are usually contiguous and, where necessary to join two protein-coding regions, are in the same reading frame. However, polynucleotides need not be contiguous to be operably linked.

A nucleic acid that regulates the expression of a heterologous polynucleotide sequence to which it is operably linked is referred to as a "transcription regulatory sequence" or an "expression control sequence." A transcription regulatory sequence is operably linked to a nucleic acid sequence when the regulatory sequence controls and regulates the transcription and, as appropriate, translation of the nucleic acid sequence. Thus, transcription regulatory sequences can include appropriate promoters, enhancers, transcription terminators, a start codon (typically, ATG) in front of a protein-encoding gene, splicing signal for introns, maintenance of the correct reading frame of that gene to permit proper translation of mRNA, and stop codons.

A "promoter" is a polynucleotide sequence sufficient to direct transcription of a nucleic acid. Typically, a promoter is situated adjacent (although not necessarily contiguous) to the start site of transcription. A promoter includes, at a minimum, a polynucleotide sequence to which an RNA polymerase can bind and initiate transcription of an operably linked polynucleotide ("minimal promoter"). A polynucleotide including a promoter can also include elements that restrict promoter-dependent expression to selected cells or tissues, or that render expression inducible by external signals or agents; such elements can be located in the 5' or 3' regions of the gene. Both constitutive and inducible promoters have been described (see e.g., Bitter et al., *Meth. Enzymol.*, 153:516-544, 1987). Specific, non-limiting examples of promoters include promoters derived from the genome of mammalian cells (e.g., metallothionein promoter) and from mammalian viruses (e.g., cytomegalovirus (CMV) immediate early gene; Rous Sarcoma virus (RSV) long terminal repeat; the adenovirus late promoter; the vaccinia virus 7.5K promoter), as well as from bacteriophage, plants and plant viruses. Promoters can also be produced by recombinant DNA or synthetic techniques.

In the context of the present disclosure, the term "core promoter" refers to the minimum sequence elements required for transcription. The core promoter includes a binding site for an RNA polymerase, and may also include binding sites for additional transcription factors or accessory molecules. In addition to the core promoter, the transcription regulatory region upstream of the coding sequence may also include one or more polynucleotide sequences that enhance transcription (an "enhancer" or "enhancer element") above the level observed with the core promoter alone, or that render promoter-dependent gene expression controllable for cell-type specific, tissue-specific, or inducible by external signals or agents.

"Expression" refers to transcription of a polynucleotide, and when used in reference to a polypeptide, to translation. Expression is the process by which the information encoded by polynucleotide sequence is converted into an operational, non-operational or structural component of a cell. The level or amount of expression is influenced by cis-acting elements and trans-acting binding factors, which are often subject to the influence of intra- and/or extra-cellular stimuli and signals. The response of a biological system, such as a cell, to a stimulus can include modulation of the expression of one or more polynucleotide sequences. Such modulation can include increased or decreased expression as compared to pre-stimulus levels. Expression can be regulated or modulated anywhere in the pathway from DNA to RNA to protein (and can include post-translations modifications, e.g., that increase or decrease stability of a protein).

The term "gene" refers to a functional nucleic acid (e.g., DNA or RNA) sequence. A gene can include coding sequences necessary for the production of a functional RNA or polypeptide (e.g., a protein of interest). The polypeptide can be encoded by a full length coding sequence or by any portion of the coding sequence so long as the desired activity or functional properties (e.g., enzymatic activity, ligand binding, signal transduction) of the full-length polypeptide, or fragment, are retained. The term also encompasses sequences associated with (e.g., contiguous with or adjacent to) a coding region that are involved in regulation of expression of the coding sequence, such as 5' untranslated sequences including for example, a promoter, enhancers and other sequences which serve as the recognition sites for protein factors involved in expression of the polynucleotide sequence. The term gene encompasses both cDNA (complementary DNA) and genomic forms of a gene.

A "transgene" is a heterologous nucleic acid, e.g., a heterologous "gene" introduced into a recipient cell or organism. Such a recipient cell, into which a heterologous nucleic acid has been introduced is referred to as a "host" cell.

A polynucleotide sequence is said to "encode" a polynucleotide or polypeptide if the information contained in the nucleotide sequence can be converted structurally or functionally into another form. For example, a DNA molecule is said to encode an RNA molecule, such as a messenger RNA (mRNA) or a functional RNA (such as an inhibitory RNA (iRNA), small inhibitory RNA (siRNA), double stranded RNA (dsRNA), small modulatory RNA (smRNA), antisense RNA (asRNA) or ribozyme, if the RNA molecule is transcribed from the DNA molecule, and contains at least a portion of the information content inherent in the DNA molecule. A DNA or RNA molecule is said to encode a polypeptide, e.g., a protein, if the protein is translated on the basis of a sequence of trinucleotide codons included within the DNA or RNA molecule. Where the coding molecule is a DNA, the polypeptide is typically translated from an RNA intermediary corresponding in sequence to the DNA molecule.

The term "polypeptide" refers to any chain of amino acids, regardless of length or post-translational modification (for example, glycosylation or phosphorylation), such as a protein or a fragment or subsequence of a protein. The term "peptide" is typically used to refer to a chain of amino acids of from about 3 to about 30 amino acids in length. For example an immunologically relevant peptide can be from about 7 to about 25 amino acids in length, e.g., from about 8 to about 10 amino acids.

A "vector" is a nucleic acid as introduced into a host cell, thereby producing a transformed host cell. Exemplary vectors include plasmids, cosmids, phage, animal and plant viruses, artificial chromosomes, and the like. Vectors also include naked nucleic acids, liposomes, and various nucleic acid conjugates. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as, promoters) and are capable of directing the transcription of an expressible nucleic acid sequence that has been introduced into the vector. Such vectors are referred to as "expression vectors." A vector can also include one or more selectable marker genes and/or genetic elements known in the art.

A "reporter" is a molecule that serves as an indicator of a biological activity. In the context of the present disclosure, a reporter serves as an indicator of transcriptional activity unless otherwise indicated. Typically, a reporter is selected for ease of detection, e.g., by optical means. Common reporters include fluorescent proteins, such as green fluorescent protein (GFP) and numerous variants thereof. Other reporters include proteins with enzymatic activities that convert a fluorogenic or chromogenic substrate into a fluorescent or visible product, or that convert an isotopically labeled substrate into a radioactive product. Examples of such enzymatic reporters include firefly luciferase, chloramphenicol acetyltransferase (CAT), β-glucuronidase and β-galactosidase. A polynucleotide encoding a reporter can be operably linked to a transcription control sequence and introduced into cells. If the transcription control sequence is active in the cell, the reporter will be expressed, and its activity can be detected (qualitatively or quantitatively) using techniques known in the art. Reporters also include selectable markers, the activity of which can be measured as relative resistance or sensitivity to a selection agent, such as an antibiotic.

A "transformed" cell, or a "host" cell, is a cell into which a nucleic acid molecule (e.g., a transgene) has been introduced by molecular biology techniques. A transformed cell or a host cell can be a bacterial cell or a eukaryotic cell.

The terms "transduction," "transfection" and "transformation" refer to the introduction of heterologous DNA/RNA into cells. These terms are used interchangeably to refer to the introduction of nucleic acids into host cells regardless of the methodology used. Common methods for introducing nucleic acids into cells include calcium phosphate-DNA co-precipitation, DEAE-dextran-mediated transfection, polybrene-mediated transfection, electroporation, microinjection, liposome fusion, lipofection, protoplast fusion, transfection with viral vectors, such as retroviral or adenoviral infection, and biolistics.

A "population" of cells includes any number of cells. Thus, a population of cells can include as few as one cell or can include many cells, for example hundreds, thousands, hundreds of thousands or millions of cells.

The term "mammal" includes both human and non-human mammals. Similarly, the term "subject" or "patient" includes both human and veterinary subjects or patients.

A "test compound" refers to any chemical entity (element, compound, molecule, complex), to be evaluated for its potential effect (genetic, physiologic and/or phenotypic) on a cell or organism. In some cases test compounds are pharmaceutical compositions, e.g., drugs, and the like that can be used to treat, mitigate, alleviate or prevent a disease, illness, sickness, or disorder of bodily function, or otherwise alter the physiological or cellular status of an organism. In methods disclosed herein, test compounds are evaluated for their ability to reduce (or inhibit or attenuate) muscle wasting and/or increase muscle growth (for example, muscle tone and/or muscle mass). Test compound also includes those chemical entities, pharmaceuticals, drugs, which act to enhance or improve an otherwise normal or nominal physiological or cellular function or status. Test compounds comprise both known and potential therapeutic compounds. A test compound can be determined to be therapeutic by using the present disclosure in the screening methods to identify molecules that affect an activity of a specific cell type, such as a muscle cell.

In the context of the present disclosure, a "library," for example a composition library, a compound library or a library of agents or potential agents, is a collection of compositions, compounds, agents, etc. A library can be restricted to a single class of compounds or can include a variety of differently classified compounds or compositions. A library can be organized and stored as a single collection or dispersed in multiple locations. A "member of a library" or "library member" is a component of such a collection. Libraries can include, without limitation, inorganic compounds, organic compounds (e.g., produced by combinatorial synthesis), natural products, chemical compositions, biochemical compositions (such as nucleic acids, e.g., DNA, RNA, DNA-RNA hybrids, antisense RNAs, dsRNAs, iRNAs, siRNAs, smRNAs and ribozymes, and peptides, polypeptides, fusion polypeptides, proteins, e.g., antibodies, and the like), metabolites, etc.

As used herein, the term "response," when used in reference to an assay, refers to the generation of a detectable signal (e.g., accumulation of reporter protein, or accumulation of a detectable product). Accordingly, methods of identification disclosed herein may involve detection of a response by a reporter construct (or cell in which a reporter construct is introduced), such as increased or decreased expression relative to a control cell.

"siRNAs" are small interfering RNAs. siRNAs can comprise a duplex, or double-stranded region, of about 18-25 nucleotides long; or siRNAs can contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs can also contain additional sequences; non-limiting examples of such sequences include linking sequences, or loops, as well as a stem loop and other folded structures. siRNAs appear to function as key intermediaries in triggering RNA interference in invertebrates and in vertebrates, and in triggering sequence-specific RNA degradation during post-transcriptional gene silencing in plants. "RNA interference" or "RNAi" refers to the silencing or decreasing of gene expression by siRNAs. In particular, RNA interference is sequence-specific, post-transcriptional gene silencing in animals and plants, initiated by siRNA which is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA.

Nucleic Acids Comprising a Human MAFbx Transcription Regulatory Sequence

The human MAFbx gene is selectively expressed in differentiated muscle cells. Tissue-specific expression of the human MAFbx gene is dependent upon activity of the upstream promoter of this gene, with elements of the immediate upstream promoter conferring muscle-specific expression. Activity of a 400 bp region beginning just upstream of the ATG is strongly enhanced after differentiation of C2C12 myoblasts into myotubes, which is indicative of muscle specific expression. The 5' end of this promoter region corresponds to the 5' end of the core promoter as determined by truncation analysis. The insert is extended 228 bases beyond the 3' border of the core promoter, and removal of this additional sequence substantially reduces activity. In contrast to some muscle genes, tissue specific expression is not further enhanced by elements up to 3.1 kb upstream of the core promoter. Specifically, myogenesis increased activity of reporters having 3.1 kb of upstream promoter to a similar degree as the 400 bp sequence, and normalized activities of the promoters were also similar.

Truncation analysis indicates that the core promoter is localized between −241 and −411 bases upstream of the ATG. A striking feature of the core promoter of the human MAFbx gene is its high homology to sequences of the corresponding rat and mouse genes. The presence of such a highly conserved sequence within the upstream promoter indicate an important function for these sequences in regulation of expression of the MAFbx gene. One inference suggested by this findings is that a common initiation site is used in all three species, corresponding to approximately 389 bases in the mouse and rat 5' UTR as compared to 340 bases for human MAFbx mRNA.

The core promoter includes two conserved forkhead bindings sites, indicateing that in human, as in the mouse, expression of human MAFbx is regulated by forkhead factors such as Foxo3A acting at the corresponding elements within the conserved sequences of the core promoter. The core promoter also includes a conserved E-Box located within this sequence between the two forkhead binding sites. This finding provides additional indirect support for interactions of basic helix-loop-helix factors such as myogenin and MyoD with sequences within the first exon of MAFbx. This is consistent with the observation that promoter activity is almost completely lost after deletion of either −240 or −311 bases upstream of the ATG, because such deletions sequentially remove the first forkhead binding sites and E-Box followed by the second forkhead site.

Sequences upstream of the core promoter exhibit low homology as compared to those within the core promoter. Whereas the core promoter includes two forkhead binding sites in all species, only one additional forkhead site is found within 3.5 kb upstream of the ATG of the human MAFbx gene. In contrast, prior analysis of the mouse MAFbx gene has found many potential forkhead regulatory elements in these upstream sequences, and has provided evidence that these upstream elements enhance effects of Foxo3A on MAFbx expression.

These differences in promoter structure indicate that there are differences in regulation of human and mouse MAFbx expression, at least with respect to the relative magnitude of changes in expression resulting from the action of specific transcription factors such as Foxo3A. In addition, these differences indicate that regulatory mechanisms beyond activation of Foxo3A are important modulators of the expression of human MAFbx. For example, upstream regions of the MAFbx promoter contain binding sites for many other transcription factors that may play important roles in modulating MAFbx expression. Levels of MyoD rise markedly after denervation, and loss of PKC-dependent phosphorylation of myogenin is an important component driving upregulation of this gene in denervation. Modulation of the phosphorylation state of myogenin or other muscle differentiation factors is therefore likely to contribute to regulation of the expression of MAFbx and other genes involved in muscle loss. For example, modulation of muscle loss by IGF-1 may involve transcription factors other than Foxo3A. Human MAFbx upstream promoter regions contain multiple binding sites for STAT3, which is a target of IGF-1 action through activation of junk-activated kinases.

The present disclosure concerns nucleic acids that are involved in the regulation of muscle specific genes and their products, and to useful compositions and methods that take advantage of the favorable properties of these polynucleotides. The present disclosure provides a human MAFbx (atrogin-1) transcription regulatory sequence (for example, a MAFbx promoter) and other expression control sequences. Certain examples disclose nucleic acids that include the human MAFbx promoter, such as the core promoter element of SEQ ID NO:1, as well as polynucleotides that include transcription regulatory sequences with additional elements that contribute to expression of an operably linked polynucleotide, such as a polynucleotide encoding a reporter or other heterologous polypeptide or RNA. Exemplary polynucleotides that include additional expression elements are represented by SEQ ID NO:2 and SEQ ID NO:3.

For example, SEQ ID NO:1 represents the polynucleotide sequence of the human MAFbx core promoter region. In the context of an intact MAFbx genomic sequence, the core promoter occupies the region between −240 and −411 with respect to the ATG that initiates translation of the MAFbx polypeptide. This polynucleotide sequence includes the minimum sequences required to confer tissue specific and steroid regulatable expression of an operably linked nucleic acid. SEQ ID NO:2 includes, in addition to the core MAFbx promoter, regulatory sequences localized between the core promoter and the translational start site, and extends between −1 and −411 of the MAFbx genomic sequence. SEQ ID NO:3 represents an exemplary polynucleotide sequence that includes genomic regulatory elements upstream (5') and downstream (3') of the MAFbx core promoter. This exemplary sequence corresponds to nucleotide −1 through −900 with respect to the translational start site.

Nucleic acids comprising the transcription regulatory region of the human MAFbx gene optionally also include additional regulatory sequences, such as additional enhancers, for example, additional regulatory elements selected from the upstream region extending beyond position −900 of the MAFbx genomic sequence.

The nucleic acid can encode one or more polypeptides to be expressed in a cell, such as a muscle lineage cell (for example, C2C12 cells or primary muscle lineage cells, including muscle cells in vivo). Thus, the MAFbx transcription regulatory sequence disclosed herein can be used to selectively express a transgene in a muscle cell. In general, any nucleic acid that directly or indirectly results in a beneficial effect is considered to be within the scope of the present disclosure. Numerous examples of transgenes suitable for expression in muscle lineage cells are known to those of ordinary skill in the art, and include, for example growth factors, hormones, cytokines, transcription factors, enzymes, metal (e.g., calcium, magnesium) binding proteins, and structural proteins, e.g., IGFs, laminins, and dystrophin. Likewise, polypeptides that interact with or bind to such cellular polypeptides can be encoded by the heterologous polynucleotide sequence. These molecules include those that encode therapeutic proteins, as well as proteins that can serve as reporters, markers (e.g., diagnostic markers) and proteins that can be used for selection of cells (e.g., antibiotic resistance genes).

In certain embodiments, the transgene is a polynucleotide sequence that encodes a reporter. Reporters include a variety of molecules that can easily be detected by optical or other means. For example, common reporters include luciferase, such as the luciferase of *Photinus pyralis*, described by de Wet et al. (*Mol Cell Biol* 7:725-737) as well as numerous homologues and variants (see, for example, U.S. Pat. Nos. 4,968,613, 5,219,737, 5,229,285, 5,330,906, 5,583,024, 5,618,722, 5,674,713 and 5,700,673, 5,843,746, 6,132,983, 6,436,682, 6,451,549, and 6,552,179. Alternative reporters include the green-fluorescent protein (GFP) of *Aequoria Victoria, Renilla reniformis*, and *Renilla mullerei* and numerous variants thereof with enhanced or altered excitation and/or emission characteristics. Exemplary GFPs suitable as reporters in the context of this disclosure include without limitation GFPs and variants described by Chalfie et al. *Science* 263: 802-805, 1994; Heim et al. *Proc Natl Acad Sci USA* 91:12501-4, 1994; Heim et al. *Nature* 373:663-4, 1995; Peelle et al *J. Protein Chem* 20:507-19, 2001; Labas et al. *Proc Natl Acad Sci USA* 99:4256-4261, 2002, and in U.S. Pat. Nos. 6,818,443; 6,800,733; 6,780,975; 6,780,974; 6,723,537; 6,265,548; 6,232,107; 5,976,796; and 5,804,387. Red fluorescent proteins are described in, e.g., U.S. Pat. No. 6,723, 537. U.S. Pat. No. 5,976,796 describes a luciferase-GFP reporter. Such fluorescent proteins can be optically detected using, for example, flow cytometry. Flow cytometry for GFP is described in, e.g., Ropp et al. *Cytometry* 21:309-317, 1995, and in U.S. Pat. No. 5,938,738. Other suitable detection methods include a variety of multiwell plate fluorescence detection devices, e.g., the CYTOFLUOR 4000® multiwell plate reader from Applied Biosciences. Additional examples of reporters with enzymatic activity include, e.g., chloramphenicol acetyltransferase (CAT), β-glucuronidase, β galactosidase and alkaline phosphatase.

The DNA molecule to be introduced and expressed in a cell under the transcriptional regulation of MAFbx transcription regulatory sequences can also encode an RNA that is not translated into a protein. Examples of such functional RNA molecules include "antisense oligonucleotide", siRNA and mRNA that can inhibit the translation or stability of a cellular mRNA, or a stable RNA such as a tRNA, a rRNA, a UsnRNA (involved in mRNA splicing), or 7SL RNA which is part of the signal recognition particle (SRP) for protein translocation into the endoplasmic reticulum. Antisense RNAs, siRNAs and mRNAs are very popular for their potential to alter cellular mRNA levels for desired genes. Another example is "ribozymes," catalytic RNAs that repair mutant mRNAs or cleave mRNAs (Sullenger & Gilboa, *Nature* 418:252, 2002; Suzuki, GeneTher 7:241, 2000; Scanlon, *J Nat Cancer Inst* 90:558, 1998.

The nucleic acid can be a vector, such as an autonomously replicating nucleic acid, e.g., plasmid vector, viral vector or it can be a linear DNA molecule. Such nucleic acids can contain other elements, in addition to the MAFbx polynucleotide sequence, to direct expression and the gene (nucleic acid) of interest or RNA molecule to be delivered. For example, it can be desirable to include a bacterial origin of replication (such as oriC) for replication of the plasmid in *Escherichia coli*, or other suitable origin of replication depending on the particular bacterial expression host. The nucleic acid, (for example, a plasmid) can also include a selection marker for selecting bacterial colonies which contain the subject nucleic acid. Such selection or biological markers are well known in the art. In bacteria, these are commonly drug-resistance genes. Drug or antibiotic resistance is used to select bacteria that have taken up cloned DNA from the much larger population of bacteria that have not.

A selection marker can also be included in the plasmid to identify mammalian cells which have taken up the plasmid DNA or to enrich for these cells. For example, the herpes simplex virus thymidine kinase (HSV tk) gene can be used as a selectable genetic marker in mammalian cells in much the same way that drug-resistance genes work in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including: zeocin, an antibiotic of the bleomycin family causing cell death by intercalating into DNA and cleaving it, the Sh Ble gene confers resistance by binding to the antibiotic and preventing its binding to DNA, and blasticidin, a potent translational inhibitor or prokaryotic and eukaryotic cells. Resistance is conferred by two Blasticidin S deaminase genes: BSD or bsr which convert Blasticidin S to a non-toxic deaminohydroxy derivative. Numerous other non-limiting examples are disclosed in Dean et al, U.S. Pat. No. 6,130,207, incorporated herein by reference.

The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

Vector systems suitable for the expression of polynucleotides under the regulatory control of a MAFbx transcription regulatory sequence include, in addition to the specific vectors described in the examples, the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986).

The nucleic acid comprising a human MAFbx transcription regulatory sequence can be transferred from its existing context to other cloning vehicles, such as other plasmids, bacteriophages, cosmids, animal viruses and yeast artificial chromosomes (YACs) (Burke et al., *Science* 236:806-812, 1987).

Substantially Similar Nucleic Acids and Polypeptides

In addition to the specific sequences disclosed above (such as SEQ ID NOs:1, 2 and 3 comprising MAFbx transcription regulatory sequences) substantially similar nucleic acids that retain the functional properties of one or more of these sequences are equivalents of the exemplary nucleic acids and can be used in the methods disclosed herein.

The similarity between and polynucleotide (and amino acid) sequences is expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid sequences, the more similar are the higher order structures resulting from folding and assembly.

Methods of determining sequence identity are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

For example, the nucleic acids disclosed herein include polynucleotide sequences with substantial sequence identity to SEQ ID NOs:1, 2 and 3. Typically, the nucleic acids have at least 95% sequence identity. Alternatively, the nucleic acids have 97%, 98% or 99% sequence identity to SEQ ID NOs:1, 2 and 3, or subsequences thereof. For example, a nucleic acid can have one, two, three, four or five nucleotide substitutions so long as the functional properties of the polynucleotide, as described herein, are maintained.

For example, where a polynucleotide encodes a polypeptide, certain substantially similar polynucleotides are identical to the reference polynucleotide, except that they vary by one or more degenerate codons. A degenerate codon is a codon is a codon that encode the same amino acid as a reference codon, but that differs in nucleotide sequence.

More importantly, with respect to the encoded protein, even where an amino acid substitution is introduced, the mutation can be "conservative" and have no material impact on the essential functions of a protein. See Stryer, *Biochemistry* 3rd Ed., 1988. Conservative amino acid substitutions are those substitutions that do not substantially affect or decrease an activity of a protein or polypeptide. Specific, non-limiting examples of a conservative substitution include the following examples shown in Table 1

TABLE 1

Exemplary Conservative Amino Acid Substitutions

| Amino Acid | Conservative Substitutions |
|---|---|
| G | A, S, N |
| P | E |
| D | S, K, Q, H, N, E |
| E | P, D, S, R, K, Q, H. N |
| N | G, D, E, T, S, R, K, Q, H |
| H | D, E, N, M, R, Q |
| Q | D, E, N, H, M, S, R, K |
| K | D, E, N, Q, R |
| R | E, N, H, Q, K |
| S | G, D, E, N, Q, A, T |
| T | N, S, V, A |
| A | G, S, T, V |
| M | H, Q, Y, F, L, I, V |
| V | T, A, M, F, L, I |
| I | M, V, Y, F, L |
| L | M, V, I, Y, F |
| F | M, V, I, L, W, Y |
| Y | H, M, I, L, F, W |
| W | F, Y |
| C | S |

Additionally, part of a polypeptide can be deleted without impairing or eliminating al of its functions. Similarly, insertions or additions can be made in the polypeptide, for example, adding epitope tags, without impairing or eliminating its functions. Other modifications that can be made without materially impairing one or more functions of a polypeptide include, for example, in vivo or in vitro chemical and biochemical modifications that incorporate unusual amino acids. Such modifications include, for example, acetylation, carboxylation, phophorylation, glycosylation, and labeling, e.g., with radionuclides, and various enzymatic modifications.

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity or substantially alter a structure, such as a secondary or tertiary structure, of a protein or polypeptide.

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I. Theory and Nucleic Acid Preparation*, Laboratory Techniques in Biochemistry and Molecular Biology, Elsevier Science Ltd., NY, N.Y., 1993. and Ausubel et al. *Short Protocols in Molecular Biology*, 4$^{th}$ ed., John Wiley & Sons, Inc., 1999.

Thus, selective hybridization is hybridization under moderately or highly stringent conditions that exclude non-related nucleotide sequences. A specific example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

Amplification of a nucleic acid molecule (e.g., a DNA or RNA molecule) refers to use of a technique that increases the number of copies of a nucleic acid molecule in a specimen. An example of amplification is the polymerase chain reaction (PCR), in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Cells Incorporating MAFbx Nucleic Acids

The present disclosure also provides host cells including the MAFbx nucleic acids described herein. A host cell is a cell into which a polynucleotide (for example, a transgene), such as a plasmid or other polynucleotide vector can be propagated and, optionally, its DNA expressed. The cell may be prokaryotic or eukaryotic. Examples of appropriate hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as C2C12, L6, HepG2, SP2/0, COS, CHO, or BHK cells, plant cells, etc. For example, the host cell can be a muscle lineage cell line such as C2C12 cells or a cell line of another cell lineage. The host cells can also be primary isolated muscle lineage cells, such as muscle derived stem cells (for example, see, U.S. Patent Application 20050265978, which is incorporated herein in its entirety. Optionally, such cells are introduced (or returned) to a subject for therapeutic purposes. In some instances, the host cells are muscle cells transfected in vivo.

The term also includes any progeny of the subject host cell. It is understood that all progeny may not be identical to the parental cell since there may be mutations that occur during replication. However, such progeny are included when the term host cell is used. Cells incorporating transgenes are useful in a variety of contexts. For example, a transgene encoding a reporter operably linked to a MAFbx transcription regulatory sequence is useful, for example, for screening potential therapeutic compounds that inhibit or attenuate muscle loss in a subject. Transgenes encoding a recombinant polypeptide, such as a growth factor, cytokine, or transcription factor are useful for producing polypeptides that reduce muscle wasting and/or enhance muscle growth in vitro and/or in vivo. A polynucleotide encoding a polypeptide that promotes muscle growth or inhibits muscle loss can be operably linked to a MAFbx transcription regulatory sequence to provide for muscle specific expression of transgenes expressing factors. In addition, the MAFbx transcription regulatory sequence induces expression of the operably linked transgene in a muscle specific manner that is activated by muscle wasting. Exemplary transgenes include polynucleotides that encode factors that promote muscle growth or block muscle atrophy (such as IGF-1, Runx1). The MAFbx transcription regulatory sequence can also be used to provide muscle-specific expression of transgenes during or after development to permit expression of normal version of defective muscle proteins in muscular dystrophies or other conditions that result in muscle loss. Examples include expression of laminin A and C, found to be mutated in Emery-Dreifuss muscular dystrophy. The principal however, can be extended to all forms of muscular dystrophy (including for example, the expression of dystrophin in Duchenne and Becker muscular dystrophies). In some cases, not only is the protein dysfunctional in the sense that it can not perform a normal function, but also in that it performs an abnormal function that exacerbates or causes muscle pathology. Expression of small inhibitory RNAs under the regulatory control of a MAFbx transcription regulatory sequence can be used to suppress expression of such proteins. One example would be muscle proteins having excessively long repeats (as occurs in dystrophia myotonica 1 and 2). In other instances a polypeptide or functional RNA can be expressed under the regulatory control of the MAFbx regulatory sequence to block inappropriate activation or reverse repression of the activities of other proteins (such as proteins involved in activation of pathways leading to cellular growth or apoptosis) or aggregation of proteins, (inclusion body myopathies), which in many tissues leads to cellular dysfunction or death (e.g., Alzheimers disease, Kennedy's Disease).

Typically, a MAFbx nucleic acid (e.g., a transgene) is introduced (transfected, transformed, or transduced) into a host cell using molecular biology techniques. As used herein, the term introduction or transduction encompasses all techniques by which a nucleic acid molecule might be introduced into such a cell, including transfection with viral vectors, transformation with plasmid vectors, and introduction of naked DNA by electroporation, lipofection, and particle gun acceleration. Optionally, one or more additional nucleic acids can also be introduced (that is, cotransfected) into the host cell. For example, a second transgene including a reporter can be cotransfected into a cell along with a reporter operably linked to a MAFbx transcription regulatory region. In some cases, the second reporter transgene is a control reporter that provides an indication of, for example, transfection efficiency. For example, in one embodiment, a first reporter transgene including a polynucleotide sequence that encodes firefly luciferase operably linked to a MAFbx transcription control sequence is cotransfected into a host cell with a second reporter transgene that includes a polynucleotide encoding a Renilla luciferase operably linked to a constitutive promoter such as the CMV promoter. In another embodiment, the host cell includes a first reporter transgene including a polynucleotide sequence that encodes firefly luciferase (or any other reporter) operably linked to a MAFbx transcription regulatory sequence and a second reporter transgene that contains a polynucleotide that encodes the same or different reporter operably linked to an IGF-1 transcription regulatory sequence. Such cells are useful, for example, in screening assays to identify agents that decrease muscle wasting and/or enhance muscle growth. Alternatively, as will be discussed below, the screening assays can make use of two different host cells, each of which includes a different reporter.

Various methods are known in the art for introducing nucleic acid molecules into host cells (including muscle lineage host cells). For example, lipid mediated transformation can be utilized to obtain efficient introduction of nucleic acids including a MAFbx nucleic acid. Liposomal or non-liposomal lipid formulations can be combined with purified nucleic acids to form complexes which are then added to cells, where the lipid-DNA complexes fuse with the cell membrane, mediating cellular uptake of the nucleic acid. For example, one lipid reagent suitable for introducing MAFbx and other nucleic acids into cells is LIPOFECTAMINE® (Invitrogen, Carlsbad, Calif.), which is useful for transfecting a broad range of cell types with nucleic acids. Another suitable lipid reagent is the non-liposomal EFFECTENE® Reagent (Qiagen, Valencia, Calif.).

Electroporation is a commonly used transformation method that can be utilized conveniently to introduce MAFbx and other nucleic acids into cells. Electroporation is well known by those of ordinary skill in the art (see, for example: Lohr et al. Cancer Res. 61:3281-3284, 2001; Nakano et al. Hum Gene Ther. 12:1289-1297, 2001; Kim et al. Gene Ther. 10:1216-1224, 2003; Dean et al. Gene Ther. 10: 1608-1615, 2003; and Young et al. Gene Ther 10: 1465-1470, 2003). Generally, in electroporation, a high concentration of vector DNA is added to a suspension of host cell and the mixture shocked with an electrical field. Transcutaneous electroporation can be utilized in animals and humans to introduce heterologous nucleic acids into muscle lineage cells in vivo. Typically, between 10 and 500 µg of DNA is introduced into cells of muscle tissue by introducing a solution containing the DNA into the muscle tissue, for example, using a needle or trochar in conjunction with electrodes for delivering one or more electrical pulses. For example, a series of electrical pulses can be utilized to optimize transfection, e.g., between 3 and ten pulses of 100V and 50 msec. In some cases, multiple sessions or administrations are performed. Alternatively, the DNA can be injected into muscle in the absence of electrical pulses, although this frequently results in a lower efficiency of transfection.

Another well known method that can be used to introduce MAFbx and/or other nucleic acids into host cells is particle bombardment (also know as biolistic transformation). Biolistic transformation is commonly accomplished in one of several ways. One common method involves propelling inert or biologically active particles at cells. This technique is disclosed in, e.g., U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle.

Another method of introducing nucleic acids into cells is microinjection, in which DNA is injected directly into the cytoplasm of cells, typically using fine glass needles. Alternatively, DNA can be incubated with an inert carbohydrate polymer (dextran) to which a positively charged chemical group (such as diethylaminoethyl, "DEAE") has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate.

As previously indicated, the nucleic acids used in the methods described herein can be plasmids. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation (according to any of the methods mentioned above) and replicated in procaryotic and/or eucaryotic cells. The DNA sequences are cloned into the plasmid vector suing standard cloning procedures known in the art, as described by Sambrook and Russel (supra).

Linear nucleic acid (e.g., DNA) molecules are also suitable in the context of the methods described herein for introducing MAFbx and other nucleic acids into cells. Published U.S. Patent Application No. 20030157717 describes the use of expression systems in the form of double-stranded linear DNA fragments with a tissue specific promoter, a transgene, a promoter, a transgene of interest and a 3' untranslated region. The double stranded DNA including the transgene is delivered to tissue of an animal by direct injection accompanied by electroporation. The linear DNA can be obtained from plasmid vectors using restriction enzyme cleavage or by using PCR from the plasmid template using standard procedures known in the art.

The host cells (including parental cells, such as untransfected cells, and progeny cells) can be cultured in conventional nutrient media under appropriate culture conditions, (e.g., temperature, pH, humidity, O2 concentration, CO2 concentration) selected based on the host cell. Optionally, agents for amplifying the heterologous nucleic acid, activating promoters, and/or for selecting transformants can be added to the medium. Appropriate culture media and conditions can be selected by those skilled in the art, and are described, for example, in references such as Freshney, *Culture of Animal Cells, a Manual of Basic Technique*, third edition, John Wiley and Sons, New York, 1994 (ISBN 0-47-155830-X) and the references cited therein.

Methods of Identifying Agents that Inhibit Muscle Loss

The disclosure also included systems (such as cell culture systems) that are useful for screening libraries of compounds to identify new agents that block muscle loss in, e.g., aging and disease. Such systems make possible rapid and sensitive measurements of changes in expression of genes involved in muscle homeostasis, such as MAFbx that are important in preventing or reversing muscle loss.

One system tests the ability of candidate compositions to turn off genes that encode factors involved in breaking down existing muscle proteins. In an exemplary embodiment, the system is based on a reporter operably linked to the transcription regulatory sequence of the human MAFbx gene. Alternatively, regulatory sequences derived from other genes that are induced during conditions of muscle loss (such as MuRF1) can be used to regulate expression of a reporter. A polynucleotide encoding a reporter, such as luciferase is operably linked to a human MAFbx transcription regulatory region, which controls expression of the reporter. Alternative reporters include green fluorescent protein ("GFP"; including variants), beta-galactosidase, and beta-glucuronidase. When introduced into a host cell, this reporter is sensitive to exposure of the cell to agents that influence muscle breakdown.

In other embodiments, the system involves a reporter under the control of transcriptional regulatory sequences obtained from a gene that is involved in promoting muscle growth (that is, at least one of muscle mass or muscle tone). For example, a polynucleotide sequence encoding a reporter can be placed under the regulatory control of transcription regulatory sequences from the Insulin-like Growth Factor I ("IGF-1") gene. IGF-1 is an important factor for stimulating muscle growth. A similar reporter gene construct to that described above can be used, except that the transcription regulatory sequences are derived from the IGF-1 gene. Expression of this reporter correlates with expression of IGF-1 under conditions that stimulate muscle growth. Accordingly, systems utilizing such a reporter can be used to identify agents that promote increased muscle mass, increased muscle tone or both, that is, agents that promote muscle growth.

These reporter systems are useful for the identification of agents that inhibit muscle breakdown and/or promote muscle growth. Such agents are candidates for novel anabolic therapies to reduce muscle loss associated with a variety of medical conditions, including conditions such as paralysis that result in immobilization, as well as numerous other conditions that result in muscle loss, including burns, chronic illness (such as HIV, heart disease, and cancer), injury, and aging.

Methods for identifying agents that inhibit muscle loss involve evaluating the ability of a test compound or agent to modify the expression of genes (such as MAFbx) that are involved in muscle loss and/or to modify the expression of genes (such as IGF-1) that are involved in muscle growth. For example, cells which have been engineered to include a recombinant nucleic acid that encodes a reporter under the control of MAFbx transcription regulatory sequences are contacted with or exposed to a test agent, and the expression of the reporter is assessed. In certain embodiments, the reporter is under the control of the human MAFbx sequences of SEQ ID NO:1, 2 or 3 or a polynucleotide sequence with at least 95% sequence similarity thereto. Any of the reporters disclosed herein is suitable in this context.

A decrease in expression of the reporter indicates that the test agent inhibits expression of MAFbx and is likely to prevent muscle breakdown when administered to a subject. Typically, a decrease in expression of the reporter gene following exposure to a test agent is compared to expression of control, such as expression of the reporter in a cell that is not exposed to the agent (e.g., in the absence of any additional compound).

Agents that increase muscle growth can be identified by exposing cells that have been engineered to incorporate a recombinant nucleic acid that encodes a reporter operably linked to an IGF-1 transcription regulatory sequence. In such methods a cell incorporating an IGF-1 reporter construct is exposed to or contacted with a test agent, and the expression of the reporter is evaluated. An increase in expression of the reporter indicates that the test agent induces expression of IGF-1 and is likely to promote muscle growth when administered to a subject. Typically, the increase is measured relative to expression of the reporter in a control cell that has not been contacted with the agent.

Thus, for example, agents that decrease muscle loss and increase muscle growth, and are therefore predicted to be particularly useful in the treatment of muscle wasting conditions, can be identified as agents that result in 1) a decrease in expression of a MAFbx regulated reporter, and 2) an increase in expression of an IGF-1 regulated reporter. In certain embodiments, the methods involve evaluating the effects of an agent on cells that include a reporter under the control of a MAFbx transcription regulatory sequence and cells that include a reporter under the control of an IGF-1 transcription regulatory sequence. In some embodiments, a single cell (or population of cells) incorporates both reporter constructs. In such embodiments, it is often convenient to provide a polynucleotide encoding a first reporter operably linked to a MAFbx transcription regulatory sequence and a polynucleotide encoding a second different reporter operably linked to an IGF-1 transcription regulatory sequence. For example, dual luciferase reporter systems such as those using a firefly luciferase reporter and a Renilla luciferase reporter that exhibit different spectra wavelength can be utilized in this context. Alternatively, luciferase and a wild-type or variant GFP as disclosed herein can be employed. Indeed, essentially any combination of reporters can be employed in a single cell so long as the reporters can be distinguished.

Alternatively, different cells (or populations of cells), that have been engineered to incorporate different reporters can both be evaluated to identify compositions that both decrease muscle loss and increase muscle growth. For example, a first cell or population of cells including a reporter under the control of a MAFbx transcription regulatory sequence can by assayed. A second cell or population of cells including a reporter under the control of an IGF-1 transcription regulatory sequence can also be assayed, and the responses of the reporters in the two cell populations can be evaluated (for example, compared). An agent that results in decreased reporter expression in the first cell and increased reporter expression in the second cell is predicted to inhibit muscle loss and promote muscle growth. In such an embodiment, the reporter can be the same or different in the two populations of cells.

The methods disclosed herein are suitable for the screening of libraries of compounds to identify agents that are drug candidates for the treatment of muscle wasting conditions. For example, the reporter systems described above can be used to evaluate compounds or compositions that are members of a library of potential therapeutic agents. Cells incorporating the reporter(s) are contacted with test agents or compounds selected from the library and the response of the reporter, that is the effect on reporter expression, is evaluated.

The test compounds of the present disclosure can be obtained from libraries of natural products or using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckemann et al., *J. Med. Chem.* 37: 2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. USA* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Chem. Int. Ed. Engl.* 33.2059, 1994; Agnew, *Chem. Int. Ed. Engl.* 33:2061, 1994; and Gallop et al., *J. Med. Chem.* 37:1233, 1994.

Libraries of compounds can be presented in solution (e.g., Houghten, *Biotechniques* 13:412-421, 1992), or on beads (Lam, *Nature* 354:82-84, 1991), chips (Fodor, *Nature* 364: 555-556, 1993), bacteria or spores (U.S. Pat. No. 5,223,409), plasmids (Cull et al., *Proc. Natl. Acad. Sci. USA* 89:1865-1869, 1992) or on phage (Scott and Smith, *Science* 249:386-390, 1990; Devlin *Science* 249:404-406, 1990; Cwirla et al., *Proc. Natl. Acad. Sci. USA* 87:6378-6382, 1990; Felici, *J. Mol. Biol.* 222:301, 1991). Alternatively, the libraries can be presented by any other method that provides access to the cell.

For example, one class of test compounds includes steroids. Steroids are a large class of molecules that exert diverse biological effects that involve modulation of transcription of responsive genes. A steroid is a lipid characterized by a carbon skeleton with four fused rings and numerous steroids are known in the art (see, for example, Briggs *Steroid Biochemistry and Pharmacology*, Academic Press, Orlando, 1970, Makin (ed.) *Biochemistry of Steroid Hormones*, $2^{nd}$ edition, Blackwell Science, Oxford, 1984. Different steroids vary in the functional groups attached to these rings. Hundreds of distinct steroids have been identified in plants and animals. Their most important role in most living systems is as hormones. In human physiology and medicine, the most important steroids are cholesterol, the steroid hormones, and their precursors and metabolites. Steroid hormones include the glucocorticoids as well as the sex hormones (for example, androgens, estrogens and progestins). In particular, glucocorticoids and androgens have important effects on muscle homeostasis.

The methods disclosed herein can be used to identify hormones, such as androgens, including natural androgens, such as testosterone, and synthetic anabolic steroids that reduce muscle loss and/or increase muscle growth (e.g., by increasing muscle mass, muscle tone, or both).

For example, when cells transduced with the MAFbx reporter construct are exposed to testosterone reporter expression is decreased consistent with the ability of testosterone to decrease muscle loss. In contrast, oxandrolone, which is known not to slow the rate of muscle breakdown, does not decrease expression of the reporter. Thus, the reporter systems and methods disclosed herein provide an means of distinguishing the biological effects of test compounds, such as steroids, that exert differential effects on muscle loss and muscle growth.

The reporter constructs and cells, and methods disclosed herein can also be used to evaluate the expression and effects of a nucleic acid (that is, a transgene) of interest. For example, a transgene (such as a transgene encoding a recombinant polypeptide or a transgene encoding a functional RNA, such as an siRNA or a ribozyme) can be introduced into a cell with one of the reporters discussed above, and the expression of the reporter can be evaluated. A decrease in expression of a reporter operably linked to a MAFbx transcription regulatory sequence indicates that the transgene is involved in inhibiting muscle loss, and is a candidate for therapeutic administration (e.g., gene therapy) to inhibit muscle wasting. Similarly, an increase in expression of a reporter operably linked to an IGF-1 transcription regulatory sequence indicates that the transgene is involved in promoting muscle growth, and is therefore a candidate for therapeutic administration to increase muscle mass or increase muscle tone or both.

Kits

The nucleic acids and cells (including reporter systems) disclosed herein can be provided as a kit. Accordingly, such a kit can include a recombinant nucleic acid including a polynucleotide that encodes a reporter operably linked to a human MAFbx transcription regulatory sequence. In an embodiment, the nucleic acid includes the MAFbx core transcription regulatory sequence of SEQ ID NO:1, or an extended MAFbx transcription regulatory sequence, such as SEQ ID NO:2 or SEQ ID NO:3. In other embodiments, the kit includes a nucleic acid with a transcription regulatory sequence that is at least 95% (or 97%, or 98%, or 99%) identical to the human MAFbx transcription regulatory sequence.

In some embodiments, the kits include one or more cells (or populations of cells) that have been engineered to incorporate a recombinant nucleic acid as described above. The kits can also include one or more additional nucleic acids or cells incorporating recombinant nucleic acids, such as additional reporter nucleic acids or cells. For example, a kit can include a second recombinant nucleic acid that encodes a reporter operably linked to an IGF-1 transcription regulatory sequence, or a cell incorporating such a nucleic acid.

Optionally, the kits can also include one or more reagents for performing a reporter assay. Such reagents vary depending on the specific reporter selected, and will be readily apparent to those of skill in the art. For example, if the reporter is a luciferase, the kit can include a detection reagent, such as luciferin, along with appropriate buffers for detecting (and optionally, quantitating) expression of the reporter. The kit can also include one or more control agents, such as agents with known effects on muscle homeostasis. For example, a kit can include a steroid. The steroid can be a glucocorticoid, such as the synthetic glucocorticoid dexamethasone, which is known to increase muscle loss. The steroid can be testosterone, which is known to prevent muscle loss (for example, in response to dexamethasone). Such steroids can be used respectively as negative and positive controls for agents that decrease muscle loss. Alternatively, the steroid can be an anabolic steroid, such as a non-virulizing anabolic steroid or a synthetic anabolic steroid (e.g., oxandrolone, nandrolone).

Generally, the kits described herein are optionally packaged to include reagents for preparing nucleic acids or proteins, amplifying nucleic acids, and/or detecting nucleic acids or other biomolecules. For example, the kits optionally include assay components, such as buffers, reagents, enzymes, serum proteins (such as antibodies), receptors, etc., for detecting expression of a reporter. In the case of prepackaged reagents, the kits optionally include pre-measured or pre-dosed reagents that are ready to incorporate into the assay methods without measurement, e.g., pre-measured fluid aliquots, or pre-weighed or pre-measured solid reagents that can be easily reconstituted by the end-user of the kit. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (such as, enzymatic inhibitors, microcides/bacteriostats, anticoagulants), the physical stabilization of the material, e.g., through immobilization on a solid support, entrapment in a matrix (such as, a bead, a gel, etc.), lyophilization, or the like. Such kits also typically include appropriate instructions for using the nucleic acids, cells and other and reagents, and optionally for preparing samples and the like. The various elements of the kits are typically packaged together in a single package or set of related packages.

EXAMPLES

Example 1

Elucidation of the Human MAFbx Promoter Structure

The promoter sequence of the human MAFbx was cloned and analyzed to identify important regulatory elements involved into tissue specificity and hormone responsiveness.

Plasmids. pMAF3.1: a 3.1 kb upstream region of the human MAFbx was cloned using sequence information from GENBANK® to design the following PCR primers: upper strand—5'-CCGACAACATAGCAAGACCCCATCTCTC-3' (SEQ ID NO:7); lower strand—5'-GAGAGGATCT-CAAGCGTTGCAGGCTCCG-3' (SEQ ID NO:8). The product was amplified by PCR using Pfx polymerase (Invitrogen) with human kidney genomic DNA as a template then cloned into TOPO-TA pCR2.1 (Invitrogen). The insert was excised with SacI and XhoI and subcloned into the same sites in pGL2-Basic (Promega). pMAF2.4: a 2.4 kb fragment from the MAFbx gene was cloned by PCR using 5'-TAACA-CATCTGTGAGGTCAACGGGAGTG-3' (SEQ ID NO:9) as a primer for the upper strand, with the above primer for the lower strand. Cloning and subcloning of the PCR product were as above. pMAF948: a 948 bp fragment of the upstream region was amplified by PCR using: 5'-TCTTAGAGGGT-TCGGGTAGGATA-3' (SEQ ID NO:10) (upper strand); and, 5'-GACTAGACGGATGGGGAGAC-3' (SEQ ID NO:11) (lower strand).

Figure 3:
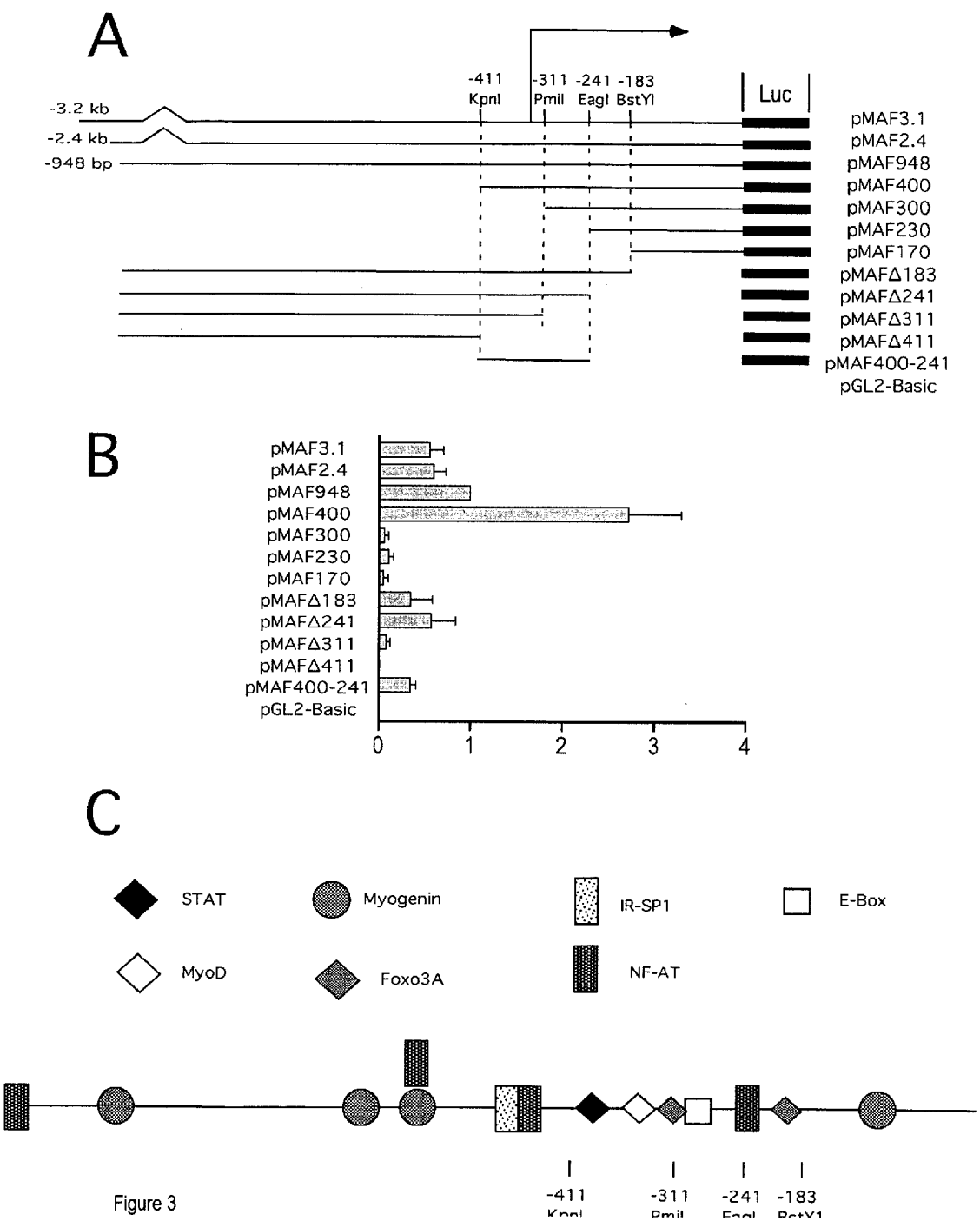
FIG. 3A is a map of reporter constructs used together with the location of restriction sites employed to generate the 5' and 3' truncations of pMAF948.
FIG. 3B is a graph of luciferase expression. C2C12 cells at 80% confluence were transfected for 3 h with the indicated reporter constructs and pCMV-Renilla then maintained in medium supplemented with 10% FBS. Twenty-four hours later, luciferase expression was quantified. Data were normalized relative to the values for the pMAF948 construct, and are mean values±SEM for three separate determinations, each performed in triplicate.
FIG. 3C is a schematic drawing illustrating selected, putative transcription factor bindings sites within the MAFbx 948 bp upstream region. The transcriptional start site (see FIG. 4) is shown as an arrow. Locations of Foxo3A sites are predicted from those in mouse MAFbx (Sandri et al., Cell 117: 399-412, 2004), while that of the E-Box was from manual inspection of the sequence. Additional searches for potential transcription factor binding sites were conducted with Match (on the world wide web at www.gene-regulation.com/cgi-bin/pub/programs/match/bin/match.cgi).

The fragment was cloned into TOPO-pTRC-His, excised with BamHI and HindIII, then ligated into the BglII and HindIII sites of pGL2-Basic. pMAF948-Luc was the starting point for several 5' deletions and 3' deletions that were prepared by excision of fragments by restriction enzyme digestion using enzymes as indicated in FIG. 3, followed by filling in of overhangs and re-ligation.

To prepare a full length cDNA clone of the MAFbx mRNA coding region, a cDNA library was prepared by reverse transcription (Omniscript, Invitrogen) using total human muscle RNA as a template (BD Biosciences; Palo Alto, Calif.) by PCR amplification using Pfx polymerase with: 5'-CACCAT-GCCATTCCTCGGGCAGGACT-3' (SEQ ID NO:12); and, 5'-GAACTTGAACAAGTTGATAAAGTC-3' (SEQ ID NO:13) as primers for upper and lower strands, respectively. This product was ligated into pcDNA3.1D/V5-His-TOPO (Invitrogen) to make pcDNA3.1-hMAFbx.

Primer Extension Analysis: Ten pmol of primer: 5'-GAC-TAGACGGATGGGGAGAC-3' (SEQ ID NO:14) was annealed to 2 µg of total RNA from human skeletal muscle (BD Biosciences, Palo Alto, Calif.). A radiolabeled reverse transcript was then prepared using the superscript first-strand synthesis system (Invitrogen, Carlsbad, Calif.) at 42° C. for 50 min after adding 1 µl of [$\alpha$-$^{32}$P]-dATP (3000 Ci/mmol). Sequence ladders were generated using an M13 mp18 DNA template and M13 sequencing primer (Sequenase DNA sequencing kit, v2.0, USB Cleveland, Ohio). The reactions were then analyzed by electrophoresis on 6% polyacrylamide gels, and the dried gels were visualized using a phosphorimager.

Cell Culture and Luciferase Assays: C2C12, L6, CHO, Hela, PC12, HepG2, CV-1 and COS7 cells (American Tissue Type Collection) were maintained in DMEM supplemented with 10% fetal bovine serum. For determination of MAFbx promoter activity in the above cell lines, cells at 80-95% confluence were co-transfected with reporter genes as indicated in the figures together with pCMV-Renilla which served as a transfection control. Cells were transfected with a total of 0.2 µg DNA per well using Lipofectamine Plus. Three hours later, cells were covered with an additional 0.8 ml of growth media. Twenty-four hours thereafter, activity of Firefly and Renilla luciferase was quantified in cell lysates using commercially prepared luciferase substrates (Promega). Luminescence was quantified with a LB 960 Microplate Lumonomiter (Berthod Technologies, Bad Wildbad-Germany).

Northern Blotting: Cells were seeded into 100 mm plates and incubated until confluent. Northern blot analysis was performed using 20 µg total RNA (RNeasy Mini kit, Qiagen, Valencia, Calif.) after resolution by electrophoresis on agarose gels and transferred onto GeneScreen membranes (PE Biosciences, Boston, Mass.). The DNA probe was generated by random priming with [$\alpha$-$^{32}$P]dCTP (MP Biomedicals, Inc. Irvine, Calif.) using full length human MAFbx cDNA as a template. Blots were hybridized at 68° C. for 1 hour in QuikHyb solution (Stratagene, La Jolla, Calif., USA) then washed. Northern blots were visualized by phosphorimaging. The scanned images were edited using Adobe Photoshop 7.0. Intensities of bands on Northern blots were quantified with ImageJ version 1.31V.

In an early report of the cloning of MAFbx it was found that the gene was expressed selectively in skeletal muscle and heart (Bodine et al., Science 294: 1704-1708, 2001), To determine whether tissue selectivity extended to cultured cell lines, total RNA was isolated from cell lines having muscle and non-muscle lineage and was used for the determination of MAFbx mRNA levels by Northern blot (FIG. 1A). Expression was highest in muscle-derived cell lines (L6 and C2C12 cells) while being low or undetectable in cells of epithelial origin (HeLa, CV1, COS7), or in cells derived from liver (HepG2) or ovary (CHO).

Muscle-specific expression arises through the concerted action of regulatory mechanisms that include expression of tissue specific transcription factors that interact with regulatory elements in the promoter regions of muscle genes (Rawls and Olson, Cell 89: 5-8, 1997). To begin to localize the upstream promoter of the human MAFbx gene and to determine whether this region conferred tissue-specific expression, a 948 bp segment of the 5' flanking sequence of the human MAFbx gene that began 14 bases upstream from the ATG was cloned by PCR using kidney genomic DNA as a template. Sequencing of the PCR product revealed two differences from the corresponding GeneBank sequence: deletion of G and C/T change at −681 and −339 bases upstream of the ATG respectively. These differences were present in three separate PCR clones from kidney DNA and were absent from that were absent from sequences for genomic DNA from lung, spleen and skeletal muscle. These sequence variations appear to represent polymorphisms in the human MAFbx promoter region. Accordingly, human MAFbx transcription regulatory sequences with including either or both of these polymorphisms is suitable for use in the compositions and methods disclosed herein.

The PCR product obtained from amplification of kidney genomic DNA was ligated into pGL2-Basic, a promoterless reporter plasmid expressing firefly luciferase. Activity of the resulting reporter gene (pMAF948) was determined after transfection into cells of muscle and non-muscle lineage (FIG. 1B). Activity was greatest in the two muscle-derived cell lines (C2C12 and L6). As compared to activity in muscle cell lines, that in cells of epithelial lineage was approximately 5-fold lower, and that in other cell types 3-fold lower. Thus, there was a good overall agreement between reporter gene activity and MAFbx levels observed in these same cell types (FIGS. 1A and 1B) indicating that promoter sequences within the first 948 bp upstream of the ATG contribute to cell-type selective expression of MAFbx.

Tissue-specific expression of genes is an important part of the program of differentiation by which embryonic cells develop into their mature, fully functional counterparts. For example, the muscle-differentiation factors myogenin and MyoD become expressed early in the program of muscle differentiation, and in turn, induce expression of other muscle-specific genes (Rawls and Olson, *Cell* 89: 5-8, 1997). To determine whether expression of MAFbx was induced during differentiation, expression of the gene was examined during differentiation of C2C12 myoblasts into myotubes that was induced by incubation in media containing 2% horse serum. Differentiation begins within hours and is nearly complete within 24 to 36 hours (Bains et al., *Mol Cell Biol* 4: 1449-1453, 1984). When levels of MAFbx mRNA in differentiating cells were assessed by Northern blotting, increased MAFbx expression was readily apparent within 24 hours and had reached a maximum by 72 hours (FIG. 2A). Intensities of the bands present on the Northern blots were quantified by densitometry scanning and normalized relative to intensities of the bands for GAPDH. Levels of MAFbx had increased 4-fold within 24 hours and reached levels 9-fold higher than undifferentiated cells by 72-hours of differentiation. By contrast, levels of MAFbx mRNA did not change appreciably over this period in undifferentiated myoblasts (FIG. 2A).

To determine whether MAFbx upstream promoter activity increased upon differentiation, C2C12 cells were transfected with reporter genes either without differentiation, or after differentiation for 48 hours. Expression of a reporter was first tested under the control of 3.1 kb of upstream promoter prepared by PCR amplification followed by ligation of the product into pGL2-Basic (pMAF3.1). This reporter was active in both undifferentiated and differentiated cells (FIG. 2B). Differentiation led to an approximately 6-fold increase in activity. In additional experiments, cells were transfected with a reporter gene constructed by 5' truncation of pMAF948. This construct contained 400 bp of upstream sequence, beginning 14 bases upstream of the first codon (pMAF400). It was also expressed in undifferentiated cells, and displayed over a 10-fold increase in activity upon differentiation. The findings indicate that MAFbx promoter activity is increased by the differentiation program and indicate that signals that are responsible for this increase act in large part through sequences located within 400 bases upstream of the ATG.

This 400 bp region includes most of the sequence coding for the 5 UTR of the human MAFbx gene, demonstrating that the 400 bp fragment is includes the minimal promoter for this gene. The boundaries the minimal promoter were further defined by the construction of additional truncations of pMAF948 and the determination of their activity after transfection into C2C12 cells. Constructs used for this analysis are shown in FIG. 3A. Removal of 100 bp from pMAF400 (pMAF300) dramatically reduced activity, indicating that key elements for basal expression are contained within the 100 bp that were removed. Several 3' truncations of pMAFbx948 were also constructed. Deletion from pMAF948 of 170 or 230 bp (pMAFΔ183 and pMAFΔ241, respectively) reduced expression modestly (less than 50%, FIG. 3B). However, a marked decrease of activity was found when an additional 70 bp were removed from the 3' end (pMAΔF311), and activity was lost completely when 400 bp were removed from the 3' end (pMAFΔ400). The above findings indicated that a region consisting of approximately 180 bp between approximately −230 and approximately −410 relative to the ATG was essential for MAFbx expression. To confirm this interpretation, an additional construct was prepared containing only this region (pMAFbx400-241). When this reporter was introduced into C2C12 cells, luciferase expression was similar to that for pMAFbxΔ241 (FIG. 3B).

Additional experiments tested how promoter sequences further upstream influenced activity. The experiments compared activity of constructs having approximately 1 kb up sequence upstream of the ATG (pMAF948) with that of reporters having 2.4 and 3.1 kb of upstream promoter (pMAF2.4 and pMAF3.1). Importantly, the inclusion of additional upstream sequences (pMAF2.4 and pMAF3.1; FIG. 3B) did not appear to enhance activity, indicating the absence of additional enhancing elements within 3 kb upstream of the first codon.

To better understand how activity of the core promoter and its flanking sequences were regulated, the first 962 bases upstream of the first codon were searched for possible transcription factor binding sites (summarized in FIG. 3C). Several sites were predicted for the basal transcription factors NF-1 and SP-1. Some SP-1 sites were organized into a motif previously linked to insulin responsiveness (SP-IR in FIG. C) (Araki et al., *J Biol Chem* 266: 3944-3948, 1991). Sites were also predicted for binding of NF-AT, linked to muscle hypertrophy (Crabtree, *Cell* 96: 611-614, 1999), and STAT3, which is activated by the muscle-trophic hormone IGF-1 (Zong et al., *J Biol Chem* 275: 15099-15105, 2000). Several sites were predicted for the muscle differentiation factor myogenin, together with one site binding another such factor, MyoD. Of considerable interest, potential binding sites for myogenin, myoD, and NF-AT, were found within the core promoter region (FIG. 3B). In addition to a single forkhead factor located upstream of the core promoter at position −1604, two binding sites for forkhead factors such as Foxo3A were identified were located within the core promoter. Their location was similar to that of sites that were previously found to be important in regulation of the mouse MAFbx (Sandri et al., *Cell* 117: 399-412, 2004), as discussed in more detail below. One E-box was identified in this region as well, representing an additional potential binding site for muscle differentiation factors such as myogenin and MyoD (Krempler and Brenig, *Mol Gen Genet* 261: 209-215, 1999).

The localization of the core promoter raised questions regarding the location of the transcriptional start site and the relationship of this site to the core promoter region. To address these questions, a primer extension analysis was performed using human muscle mRNA as a template (FIG. 4), and employing a primer beginning 14 bases upstream of the ATG. This analysis revealed a single major product of 327 bases based upon comparison of its mobility to that of sequencing standards, from which the major transcriptional start site can be inferred to be 341 bases upstream of the ATG. This determination adds 147 bases to the length of the 5' UTR obtained from the original cDNA clone (Bodine et al., *Science* 294: 1704-1708, 2001). Inspection of the sequences immediately upstream of the transcription start site revealed no TATA or CAAT box.

Comparison of the nucleotide composition of mouse and rat MAFbx upstream promoter regions revealed a high GC content (66% and 62.8%, respectively). However, the human MAFbx upstream promoter region had an even higher GC content (73.8%), largely because of a particularly GC-rich region in the 5' UTR. Alignment of the sequences for the first 1 kb of the upstream promoter for mouse, rat and human MAFbx genes revealed that, overall, the sequences of the three species were 62.6% identical. The three genes contained a highly conserved region spanning approximately 140 bp and containing the transcriptional start site for the human MAFbx promoter. Sequences within this region were approximately 78% identical, while those beyond it were 52% identical. Sequences flanking the transcriptional start site of human MAFbx were absolutely conserved.

Of interest, the conserved region involved largely sequences downstream of the transcriptional start site, and contained two elements for forkhead transcription factors shown to be important for upregulation of the mouse MAFbx gene by starvation or glucocorticoids (Sandri et al., *Cell* 117: 399-412, 2004). These forkhead transcription factor consensus sites (double underlined, FIG. 5) were present in essentially identical locations in the three genes, which fell within the core promoter of the human MAFbx upstream promoter. Both sites were situated downstream of the transcriptional start site for the human MAFbx gene. The sequences of these sites match exactly those for two corresponding sites in mouse and rat MAFbx upstream promoter regions. Sequences flanking these sites were also highly conserved.

Mechanisms by which promoters mediate muscle-specific gene expression are varied, with several different mechanisms employed. Upstream elements containing an E-box and several CArG boxes enhance expression of mouse myosin light-Chain 1A in a tissue-specific manner, while E-Boxes within the first exon enhance both levels of expression and muscle selectivity of the myotonic dystrophy protein kinase gene (Catala et al., *Mol Cell Biol* 15: 4585-4596, 1995; Storbeck et al., *J Biol Chem* 273:9139-9147, 1998). In some cases, the core promoter itself also confers tissue-specificity, as is the case for the myotonic dystrophy protein kinase genes (Storbeck et al., *J Biol Chem* 273:9139-9147, 1998, Smith et al. *Am. J. Physiol* 274:C1188-1195, discussion C1187, 1998). Intronic transcriptional elements also have been implicated in tissue-specific expression of muscle genes (Angus et al., *J Biol Chem* 276:17603-17609, 2001).

Tissue-specific expression of the human MAFbx gene is dependent upon activity of the upstream promoter of this gene. This conclusion is based on the cell-type expression of reporter gene under the control of a 948 bp portion of upstream promoter beginning just 5' to the first codon. Several lines of evidence indicate that elements of the immediate upstream promoter, and possibly within the first exon, confer such muscle-specific expression. Activity of a 400 bp region beginning just upstream of the ATG was strongly enhanced after differentiation of C2C12 myoblasts into myotubes. Such enhancement can serve as a test for muscle-specific expression (Catala et al., *Mol Cell Biol* 15: 4585-4596, 1995). The 5' end of this promoter region corresponds to the 5' end of the core promoter determined by truncation analysis. The insert is extended 228 bases beyond the 3' boarder of the core promoter, and removal of this additional sequence substantially reduces activity, possibly through removal of a myogenin binding site. In contrast to some muscle genes, tissue specific expression was not enhanced by elements up to 3.1 kb upstream of the core promoter. Specifically, myogenesis increased activity of reporters having 3.1 kb of upstream promoter to a similar degree as the 400 bp sequence, and normalized activities of the promoters were also similar. Insight into the identity of potential transcription factors that influence activity of the MAFbx promoter is available from the analysis of sequences for potential transcription factor binding sites. This analysis indicated potential binding sites for several myogenic factors including myogenin and MyoD, as well as for factors known to regulate muscle hypertrophy (NF-AT) or the action of extrinsic factors promoting such hypertrophy such as IGF-1 acting via STAT3.

Figure 4:
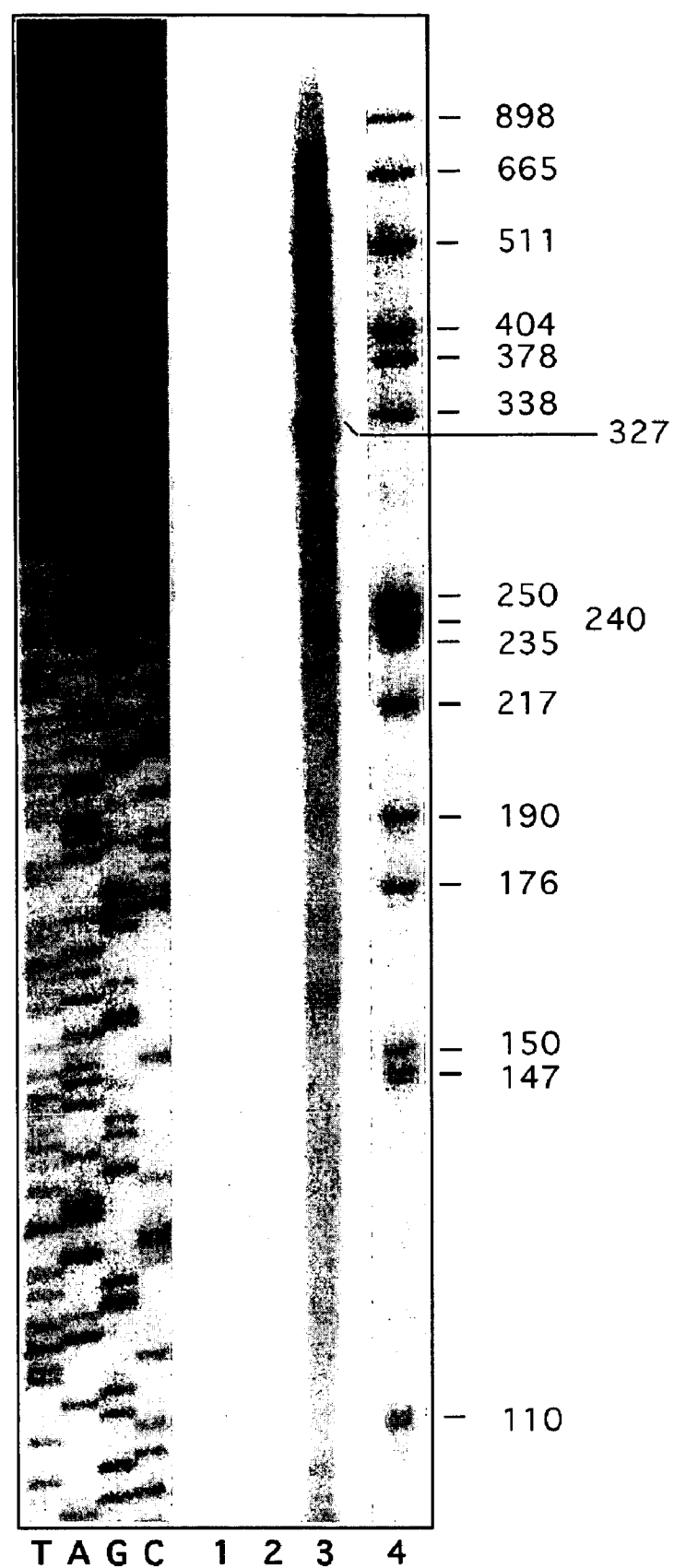
FIG. 4 is an image showing a primer extension analysis of the 5' UTR of human MAFbx mRNA. Radiolabeled products generated by reverse transcription of human muscle total RNA ATG were resolved by PAGE (Lane 3). The primer used began 14 bases upstream of the ATG. Identical reactions without RNA (Lane 1) or containing yeast mRNA (Lane 2) were used as controls. T, A, G, and C indicate lanes for the corresponding sequencing standards (see Materials and Methods). Lane 4: αP[32]-dATP-labeled size standards generated by digestion of pGL2-basic with Hpa II.

Truncation analysis indicated that the core promoter was localized between −235 and −411 bases upstream of the ATG. This region is highly conserved between the corresponding regions of the rat and mouse genes. This similarity indicates that a common initiation site is used in all three species, and that the 5' UTR of mouse and rat MAFbx mRNA is approximately 389 bases as compared to 341 bases for human MAFbx mRNA as shown by primer extension analysis (FIG. 4). These analyses indicate that the major transcriptional start site is further upstream than previously predicted (Gomes et al., *Proc Natl Acad Sci USA* 98:14440-14445, 2001; Bodine et al., *Science* 294:1704-1708, 2001).

The conserved region of the core promoter contains two absolutely conserved forkhead bindings sites. Studies of the mouse MAFbx upstream promoter have provided evidence that in mice, each of these forkhead sites contributes to upregulation of MAFbx in disease states, and that upregulation is attributable to binding of Foxo3A at these elements (Sandri et al., *Cell* 117: 399-412, 2004). These findings argue that expression of human MAFbx is regulated by forkhead factors such as Foxo3A acting at the corresponding elements within the conserved sequences of the core promoter.

A conserved E-Box is located within this sequence between the two forkhead binding sites. This finding provides additional indirect support for interactions of basic helix-loop-helix factors such as myogenin and MyoD with sequences within the first exon of MAFbx. When considering this possibility, it is of interest that promoter activity is almost completely lost after deletion of either −240 or −311 bases upstream of the ATG, because such deletions sequentially remove the first forkhead binding sites and E-Box followed by the second forkhead site (FIG. 3). This interpretation is consistent with findings from studies of the regulation of the mouse MAFbx gene, which indicated through mutational analysis that both of the forkhead sites located in the noncoding region of the first exon contributed to upregulation of this gene in muscle loss states (Sandri et al., *Cell* 117: 399-412, 2004).

The 5' UTR of the MAFbx genes from three mammalian species also revealed a relatively high-GC content with the frequent occurrence of CpG islands This was particularly true for the human MAFbx gene.

Sequences upstream of the core promoter showed low homology as compared to those within the core promoter. Differences in promoter structure indicate that there may be differences in regulation of human and mouse MAFbx expression, at least with respect to the relative magnitude of changes in expression resulting from the action of specific transcription factors such as Foxo3A. In addition, these differences indicate that regulatory mechanisms beyond activation of Foxo3A are important modulators of the expression of human MAFbx. For example, upstream regions of the MAFbx promoter contain binding sites for many other transcription factors that may play important roles in modulating MAFbx expression. In addition, modulation of muscle loss by IGF-1 may involve transcription factors other than Foxo3A. Human MAFbx upstream promoter regions contain multiple binding sites for STAT3, which is a target of IGF-1 action through activation of junk-activated kinases (Zong et al., *J Biol Chem* 275: 15099-15105, 2000).

Example 2

Muscle-Loss Genes as a Target for Pharmacotherapy

The accelerated breakdown of muscle proteins is the primary mechanism of muscle loss. This increased degradation of muscle proteins involves the increased expression of several genes. One such gene is MAFbx (Muscle Atrophy F-Box), which encodes a ubiquitin ligase involved. To demonstrate that androgens prevent muscle protein breakdown by blocking expression of MAFbx a series of experiments was undertaken to determine the steroid responsiveness of the MAFbx promoter.

Anabolic steroids are androgen analogs with reduced virulizing activity. They appear to preserve or increase muscle mass in many catabolic states. Their primary mechanism of action involves binding to and activation of the androgen receptor (AR), a ligand-activated transcription factor. The AR then modulates gene expression. In many states of muscle loss, glucocorticoids are required. These presumably act via the glucocorticoid receptor (GR).

The following experiments provide a characterization of the androgen and glucocorticoid responsiveness of the MAFbx promoter utilizing a luciferase reporter system.

Plasmids

The reporter genes pMAF3.1, pMAF2.4, pMAF948, pMAF400, and pMAF400-241 express firefly luciferase under the control of promoter regions of the human MAFbx gene and are described in Example 1. The rARC562G vector, encoding rat AR with a C562->G mutation in the first zinc binding module that disrupts binding of AR to DNA was described by Palvimo et al. (*Mol Endocrinol* 7: 1399-1407, 1993) pAR.4RKM (expressing AR with 4 R/K->M mutations in the nuclear localization sequence that is unable to enter the nucleus) and pAR.ABC (lacking the ligand binding domain) were described by Zhou et al. (*J Biol Chem* 269: 13115-13123, 1994). The pBabe.puro retroviral backbone described by Morgenstern and Land (*Nucleic Acids Res* 18: 3587-3596, 1990) was modified by introduction of a NotI site. The ARE reporter gene expressing firefly luciferase under control of the MMTV hormone response element, and pSP72hAR-1, containing an insert of the full-length cDNA clone of the human AR, were provided by Dr. Diane Robins (University of Michigan). pRL-CMV expressing Renilla luciferase was from Promega (Madison, Wis.).

Cell Culture and Transfection

C2C12 cells (American Type Culture Collection, Manassas, Va.) were maintained in Dulbeco's modified Eagle's Medium (DMEM) containing 10% fetal bovine serum (FBS) and penicillin (100 U/ml)/streptomycin (100 µg/ml) (growth medium). Cells were incubated at 37° C. in humidified air containing 10% $CO_2$. 293T cells (American Type Culture Collection) were maintained in growth medium as above. Transfection was achieved using Lipofectamine-Plus (Invitrogen, Carlsbad, Calif.) using 200 ng total DNA per well.

Retrovirally Transformed C2C12 Cells Stablely Expressing Human AR

The retroviral backbone for expressing human androgen receptor (pBabe hAR) was constructed by ligating the BglII-XbaI fragment of pSP72hAR-1, including the complete coding region for the human AR, into the BamHI and HindIII sites of the pBabe puro vector (pBabe.puro.hAR). This construct was co-transfected together with vectors expressing gag-pol and VSV-G into 293T cells. The supernatants were harvested and the cell debris was removed by centrifugation at 500 g. The supernatant was used to infect the wild type C2C12 cells after addition of polybrene (4 µg/ml). After 24 hours, puromycin (1,600 ng/ml) was added to the culture medium. After drug selection for 4 weeks, cells were subjected to dilutional cloning yielding six lines. Properties of these cells are described in Results.

Luciferase Assays

Cells were seeded into wells of 24-well plates ($5 \times 10^5$ cells/well) then maintained overnight in DMEM with 10% CDS-FBS. Cells were co-transfected with the various reporter genes and pRL-CMV. Cells were incubated in the transfection mixture overnight, then covered with DMEM supplemented with 10% charcoal-dextran-stripped FBS (CDS-FBS) and either ethanol (EtOH) or hormones dissolved in EtOH. Cells were maintained for an additional 24 hours, at which time both firefly and renilla luciferase activity were determined using the Dual Luciferase Assay (Promega, Madison, Wis.) and a Berthold 96-well plate luminometer. Firefly luciferase activities were normalized relative to renilla luciferase. Ethanol concentrations were less than 0.1%. Solutions containing testosterone were prepared freshly on the day of the experiment, as loss of activity was observed with storage of testosterone in ethanol solutions.

Northern Blotting

Cells were seeded into 100 mm plates and grown until confluent. Northern blot analysis was performed using 20 µg total RNA (RNAeasy Mini kit, Qiagen, Valencia, Calif.) after resolution by electrophoresis on agarose gels and transfer onto GeneScreen membranes (PE Biosciences, Boston, Mass.). The DNA probe was generated by random priming with $[\alpha$-$^{32}P]dCTP$ (MP Biomedicals, Inc. Irvine, Calif.) using the BglII-XbaI fragment of pSP72hAR-1 as a template. Blots were hybridized at 68° C. for 1 hour in QuikHyb solution (Stratagene, La Jolla, Calif., USA) then washed. Northern blots were visualized by phosphorimaging. The scanned images were edited using Adobe Photoshop 7.0.

Real Time PCR (qPCR)

Incubations of Cells and Extraction of RNA

Cells were seeded into wells of 6-well plates at $3 \times 10^6$ per well in DMEM supplemented with 10% CDS-FBS. For determination of basal expression of mouse AR and hAR, RNA was harvested the following day. For assessements of drug effects on mRNA levels, cells were incubated overnight in this medium. Where indicated, cells were then incubated for 48 hours in DMEM containing 2% horse serum to induce differentiation. Steroid hormones or ethanol were added and cells were incubated overnight. For Determination of mRNA half life, medium was supplemented with actinomycin (5 µg/ml). Cells were lysed with guanidine thiocyanate either immediately, or at various times thereafter, for determination of AR mRNA levels. Total RNA was extracted from cultured cells using RNAeasy columns (Qiagen) after disruption of cells with Qiashredder columns (Qiagen), freed of residual DNA by digestion on the column with RNAse-free DNAse (Qiagen), and eluted with water.

Extraction of RNA from Skeletal Muscle

Muscle was flash frozen on dry ice after excision. Total RNA was isolated by phenol:chloroform extraction (Chomczynski and Sacchi, *Anal Biochem* 162: 156-159, 1987) and further enriched using RNAeasy minicolumns (Qiagen) with digestion on the column with RNAse-free DNAse (Qiagen).

Real-Time PCR

RNA was quantified by absorbance at 260 nm. One microgram of total RNA was used to prepare cDNA libraries using the High Capacity cDNA Archive Kit (Applied Biosystems, Foster City, Calif.). Libraries were diluted 25-fold with water. Real time PCR was performed using Taqman 2×PCR buffer (Applied Biosystems) and an Applied Biosystems 7500 thermocycler. Data were normalized relative to that for 18S RNA. Relative changes in expression were determined using the $2^{-\Delta\Delta Ct}$ method. Taqman Assay on Demand probes (Applied Biosystems) were used for all assays except rat 18S RNA, which was quantified using the following Assay on Demand Probes: Forward: CGCAGCTAGGAATAATGGAATAGGA (SEQ ID NO:15); Reverse: GGCCTCAGTTCCGAAAAC-CAA (SEQ ID NO:16); Probe: FAM-CCGCGGTTC-TATTTTG (SEQ ID NO:17; Labeled with FAM and non-fluoresent quencher, NFQ, at 5' and 3' ends, repsectively).

Animals

Male Wistar rats weighing 250 gm were anesthetized with ketamine/xylazine followed by implantation Alzet miniosmotic pumps administering vehicle (propylene glycocol), dexamethasone (0.7 mg/kg/day), or dexamethasone plus testosterone (28 mg/kg/day). The testosterone dose used was approximately 10 times greater than a typical replacement dose in rats (Wright et al., *Endocrinology* 140: 4509-4515, 1999), while the dexamethasone dose was similar to higher doses used in humans. Seven days later, animals were euthanized, and muscles of the hind limb were excised after careful dissection.

Statistics

Statistical analysis was performed using Prism 4.0c software (Graph Pad Software, San Diego, Calif.). Comparisons between two means were performed using a Students t-test. Comparisons among multiple means were performed using one-way ANOVA with a Newman-Keuhls test to determine significance of differences between specific means. A $p<0.05$ was considered significant.

Figure 6:
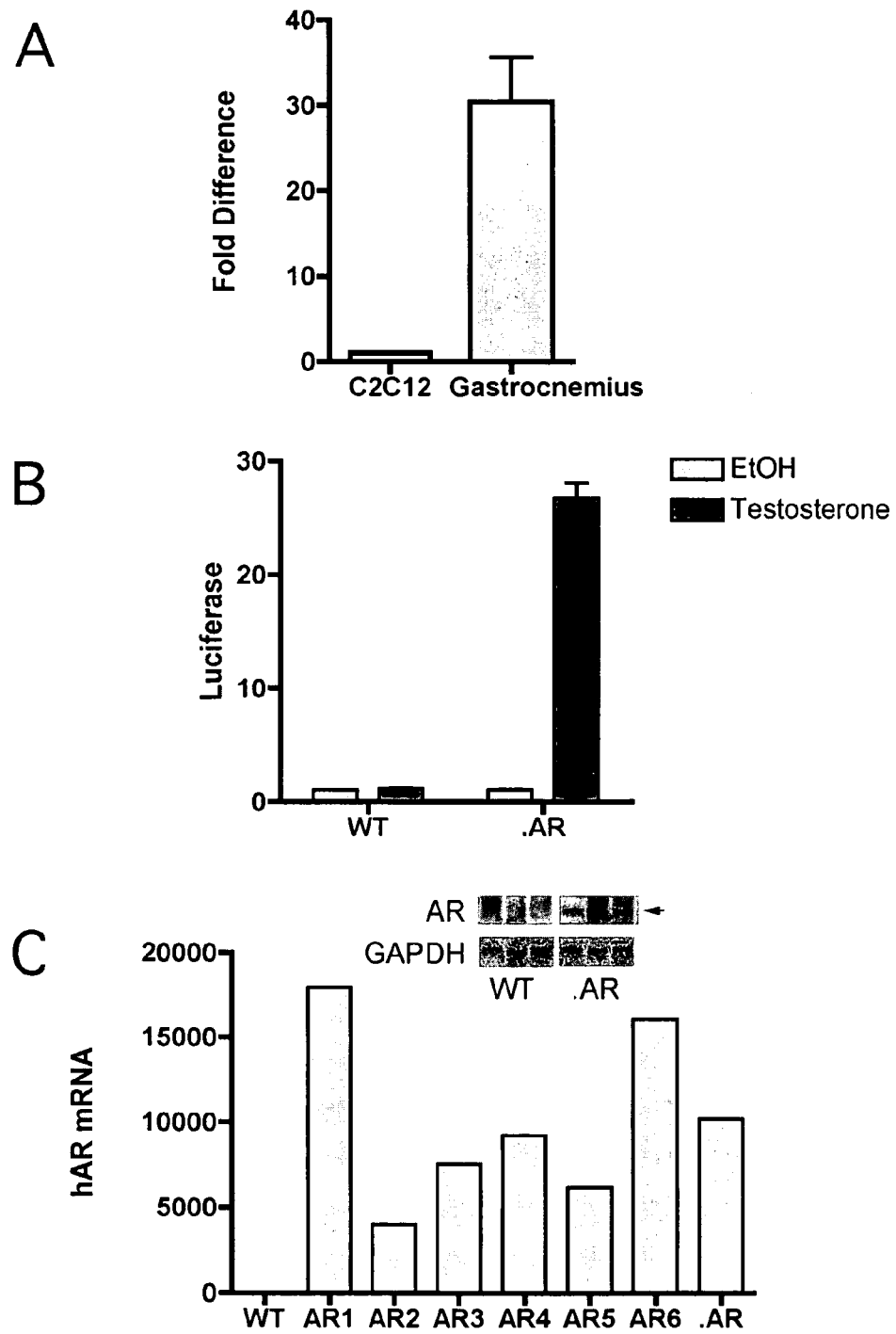
FIGS. 6A-C are bar graphs illustrating the properties of C2C12.AR cells. (A) Expression of mouse AR in C2C12 cells maintained in DMEM plus 10% FBS as compared to that in the gastrocnemius muscle of male mice. Data are mean values for three determinations each performed in triplicate, and are expressed as fold difference in expression relative to C2C12 cells. (B) Effects of testosterone on luciferase expression in wild-type C2C12 or C2C12.AR cells transfected with the ARE reporter gene. Results of a representative experiment performed with six replicates are shown. Results were reproducible in two consecutive experiments. (C) Expression of human AR in wild-type C2C12 cells and clonal lines derived from C2C12.AR cells. Data are mean values of a representative experiment with assays run in triplicate. Inset, northern blot for AR. WT, wild-type C2C12 cells; C2C12.AR, pool of drug-selected C2C12 cells expressing hAR; AR1-AR6, clonal lines derived from C2C12.AR.

To determine whether C2C12 cells expressed AR, total RNA from these cells was extracted and analyzed by real-time PCR and compared to levels of AR mRNA in gastrocnemius muscle from male mice. Expression was approximately 30-fold lower in C2C12 cells as compared to skeletal muscle (FIG. 6A), indicating that levels may be below those needed to modulate effects of testosterone. To test this possibility, the ability of testosterone to induce luciferase expression in C2C12 cells transfected with a reporter gene containing the MMTV hormone response element was tested. Testosterone induced only minimal (about 2-fold) increases in luciferase expression over baseline (FIG. 6B), confirming that AR levels were below the minimum needed for significant effects on gene expression. Therefore, C2C12 lines expressing human AR were generated by infection of wild-type C2C12 cells with a retroviral vector containing the full length cDNA for human AR, followed by drug selection. The ability of testosterone to induce luciferase expression by the ARE-Luc reporter gene was then tested in this pool of drug-selected cells (C2C12.AR cells). Testosterone caused a marked increase in luciferase expression in these cells (FIG. 6B). To confirm expression of the hAR mRNA in C2C12.AR cells, total RNA from these cells was subjected to Northern blotting, which revealed the presence of a band that was absent from wild-type C2C12 cells (FIG. 6C, insert). Analysis by real-time PCR (qPCR) of hAR expression in clonal lines derived from C2C12.AR cells revealed high-level expression of hAR message in all clones (FIG. 6C). For the remainder of the disclosure, the pool of hAR-expressing cells are referred to as C2C12.AR cells, while individual clones are referred to by clone number (for example, AR6).

To test the effects of testosterone on MAFbx expression, the ability of testosterone to inhibit activity of pMAF3.1 was examined. Experiments with wild-type C2C12 cells revealed no effect of testosterone on activity of this reporter gene over a range of concentrations from 5 to 500 nM (FIG. 7A). When the experiments were repeated using C2C12.AR cells, significant repression was observed at 5 nM testosterone (about 40%) which increased to greater than 50% repression as the concentration was raised to 500 nM (FIG. 7A). These findings indicate that testosterone repressed MAFbx promoter activity in a manner that required the AR and was dose-dependent.

To localize the elements mediating such repression, the experiments were repeated using reporter genes having progressive 5' deletions of the MAFbx promoter region. Repression of pMAF3.1 by 500 nM testosterone was apparent for each of the three 5' truncations (FIG. 7B), including pMAF400, in which virtually all sequences upstream of the transcriptional start site have been eliminated. A 3' deletion of 208 bases encoding the 5' untranslated region abolished suppression by testosterone. These findings indicated that repression of basal MAFbx expression by AR required regulatory sequences within the region coding the 5' UTR.

To further evaluate the mechanism underlying this effect, experiments were repeated in wild-type C2C12 cells co-transfected with the pMAF3.1 reporter and vectors expressing wild-type AR, or mutant ARs deficient in specific AR functions (FIG. 8). Testosterone significantly depressed reporter gene activity in cells transfected with wild-type AR. No repression was observed in cells transfected with an AR defective in nuclear entry (4RKM) that remained trapped in the cytoplasm. Repression was also absent in cells expressing AR lacking the ligand binding domain but able to enter the nucleus and bind chromatin (ABC). However, repression was observed when cells were transfected with an AR containing a mutation in the DNA binding domain and unable to bind chromatin (C562G), although the magnitude of repression was reduced by this mutation. These data indicate that while the ligand binding domain and nuclear entry are required for repression, DNA binding is not.

Figure 9:
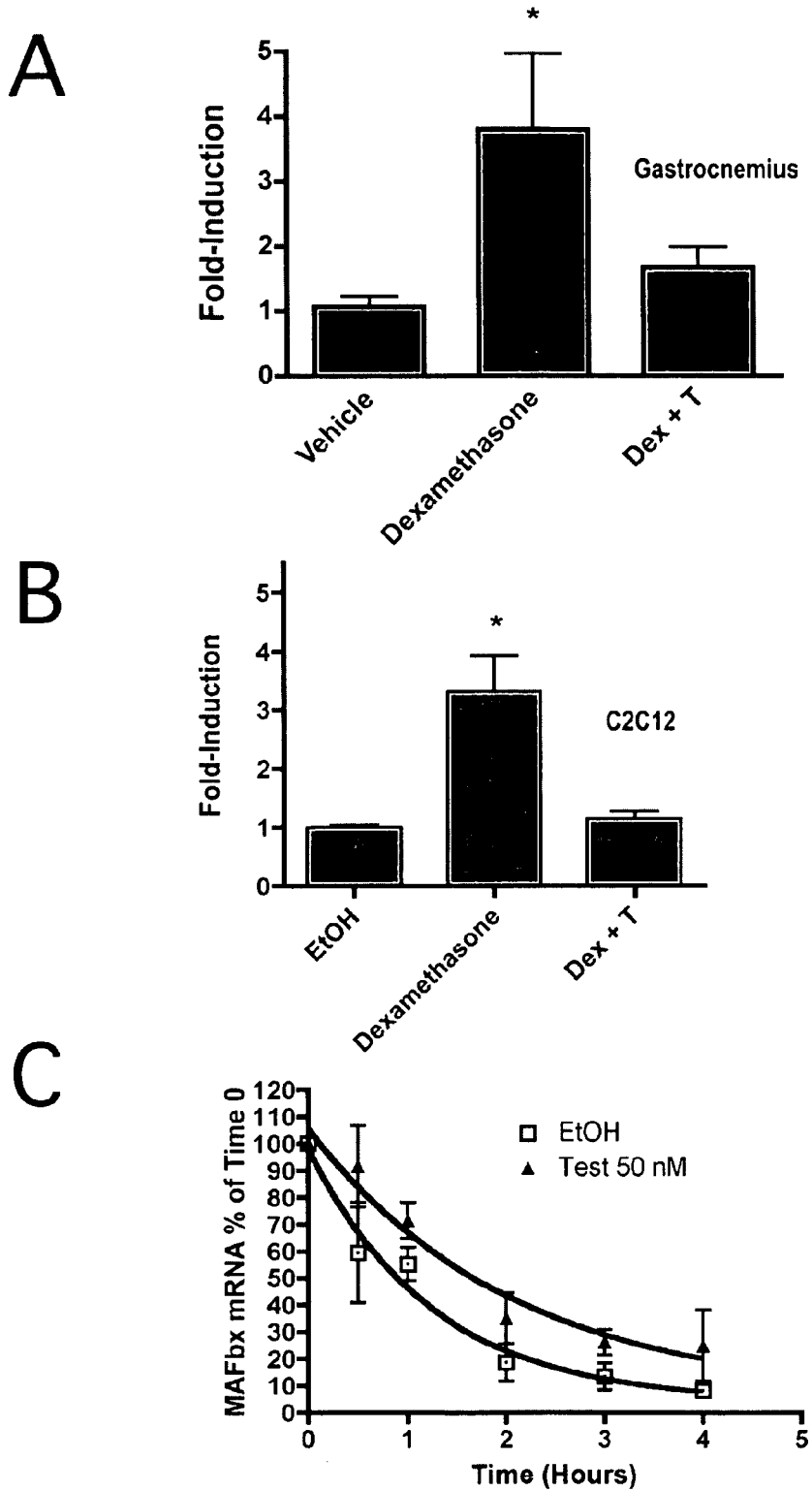
FIGS. 9A and B are bar graphs and FIG. 9C is a line graph illustrating that testosterone does not alter MAFbx RNA stability. (A) Rats were administered test agents as indicated in the figure for 7-days, at which time animals were sacrificed and MAFbx expression was determined in gastrocnemius muscles by qPCR. Data are mean values±SEM for at least 8 animals. * $p<0.05$ vs vehicle, t-test. (B) AR6 cells were seeded into 6-well plates and incubated overnight in growth medium. Medium was replaced with DMEM containing 2% horse serum followed by incubation for an additional 48 hours. Hormones or vehicle (EtOH) were added to the medium and cells were incubated overnight, at which time MAFbx mRNA levels were determined by qPCR and expressed as fold-induction versus levels in cells incubated with EtOH. Data are mean values±SEM for three determinations each performed in triplicate. * p<0.05 vs. EtOH (ANOVA). (C) Effect of testosterone on MAFbx mRNA half-life. C2C12.AR cells were incubated overnight in growth medium supplemented with testosterone or vehicle (EtOH). Actinomycin was added to media and cells were harvested at indicated times thereafter for determination of MAFbx mRNA levels by qPCR. Levels of MAFbx mRNA are expressed as a percentage of those at time zero. Data are mean values±SEM for three separate experiments. Each determination was performed in triplicate. Half-lives for EtOH and testosterone were not significantly different (ANOVA).

To determine whether these effects of testosterone extended to states where expression of MAFbx was induced by disease, the ability of testosterone to block dexamethasone-induced upregulation of the MAFbx gene was tested in rats (FIG. 9A). Infusion of dexamethasone for 7 days resulted in a significant (almost 4-fold) increase in expression of MAFbx in gastrocnemius muscle. Levels of MAFbx mRNA in animals administered a concurrent infusion of dexamethasone with testosterone were not significantly different from levels in animals administered vehicle, indicating that testosterone completely blocked effects of dexamethasone on MAFbx expression. In these studies, testosterone was administered at a pharmacologic dose that was approximately 10-fold greater than a replacement dose.

These experiments were extended by testing whether testosterone reduced MAFbx mRNA expression in AR6 cells exposed to dexamethasone. Measurement of levels of MAFbx mRNA in C2C12.AR cells revealed that dexamethasone significantly increased expression of this gene (approximately 3)-fold (FIG. 9B). Expression was reduced by concurrent administration of testosterone to levels that were not significantly different from those for cells exposed to ethanol only, indicating that testosterone prevented dexamethasone effects on MAFbx expression in these cells. To test whether some of these effects of testosterone could reflect changes in the stability of MAFbx mRNA in the presence of this hormone, additional experiments determining the effect of testosterone on half-life of MAFbx mRNA were performed (FIG. 9C). The half-life of mRNA was just more than one hour in C2C12.AR cells in the absence of testosterone. The half-life was not significantly different in cells incubated with testosterone (ANOVA).

The above findings indicated that the ability of testosterone to block dexamethasone-induced increases in levels of MAFbx mRNA involved repression of dexamethasone-induced activation of MAFbx transcription. This was confirmed by characterizing the effects of testosterone on dexamethasone-induced activation the pMAF3.1 reporter in C2C12.AR cells. Dexamethasone increased luciferase expression in these cells by more than 1.5 fold (FIG. 10A) consistent with our prior findings. At a testosterone concentration of 5 nM, dexamethasone induced luciferase expression was partially inhibited, with full suppression achieved at a concentration of 50 nM. Luciferase expression appeared to be suppressed below that of untreated cells at a testosterone concentration of 500 nM.

To determine whether the suppression of dexamethsone-induced activation of MAFbx by testosterone was due to repression of the activity of forkhead transcription factors, or to interactions with transcription factors acting downstream of the core promoter the effects of dexamethasone on expression of a reporter incorporating (pMAF400) or lacking (pMAF400-241) such sequences in C2C12 cells were compared. Dexamethasone induced almost two-fold activation of the pMAF400 reporter, consistent with prior studies (FIG. 10B). Activation was abolished when the last 200 bases of the 5'UTR were removed.

Elevated expression of MAFbx is a universal feature of muscle loss states. In many conditions associated with muscle loss, high circulating levels of glucocorticoids are essential for progression of such loss (e.g. burns, sepsis, diabetes, and starvation. Testosterone has been found to oppose the catabolic effects of exogenous glucocorticoids on muscle in elderly men (Crawford et al., *J Clin Endocrinol Metab* 88: 3167-3176, 2003; Reid et al., *Arch Intern Med* 156: 1173-1177, 1996), and to block muscle catabolism in burn victims (Ferrando et al., *Crit Care Med* 29: 1936-1942, 2001), in whom cortisol levels are greatly elevated (Jeffries and Vance, *J Burn Care Rehabil* 13: 391-395, 1992).

It is likely that testosterone preserves muscle in these conditions, at least in part, through its ability to oppose the action of glucocorticoids on MAFbx expression. Such reversal of glucocorticoid action by testosterone involved repression by testosterone of the transcriptional activation of the MAFbx gene induced by dexamethasone, as reflected by the ability of testosterone to block increases in MAFbx reporter gene activity induced by dexamethasone. This blockage reflects transcriptional activity and is not related to mRNA stability. Although testosterone has been reported to act as an antagonist of the GR, it seems unlikely that antagonism is responsible for the repression by testosterone of dexamethasone effects on MAFbx expression for two reasons: (1) at higher concentrations, testosterone reduced MAFbx promoter activity in dexamethasone-treated cells below baseline; (2) testosterone was effective in reducing dexamethasone-induced MAFbx expression achieved at by high dexamethasone concentrations at low nanomolar concentrations of testosterone, whereas the $K_D$ of testosterone for the GR has been reported to be much higher (approximately 200 nM; (Danhaive and Rousseau, *J Steroid Biochem* 24: 481-487, 1986). The observed repression of both basal and glucocorticoid-induced MAFbx expression occurs at physiological concentrations of testosterone (10-40 nM).

Full effects of dexamethasone to cause transcriptional activation of the human MAFbx gene by glucocorticoids require only the core promoter and sequence encoding the 5'UTR. Findings that deletion of the 5'UTR sequences prevented activation of the MAFbx promoter by dexamethasone indicated that these sequences are involved in activation of the human MAFbx gene by glucocorticoids. These same sequences are necessary for repression of basal MAFbx expression by testosterone. Thus, activation of MAFbx expression by glucocorticoids, and suppression of MAFbx expression by testosterone, each involve sequences from the 5'UTR.

It is likely that downstream sequences also play a role in expression of the MAFbx gene, because sequences within the 5'UTR were found to strongly activate basal expression of the human MAFbx gene. Together, these findings indicate that interactions occur between transcription factors bound to these downstream sequences, and several transcription factors binding at the core promoter.

Without being bound by theory, these finding indicate a model for the molecular mechanisms by which testosterone reduces basal MAFbx expression and suppresses activation of this gene by dexamethasone. In this model, the AR interacts with factors bound to sequences encoding the 5'UTR and interferes with the normal, activating effect of these factors on the core promoter. This inhibitory effect of the AR also extends to the heightened activity of the core promoter achieved by glucocorcorticoid-induced recruitment of FOXO3A to the core promoter. This model does not assume direct interactions of AR with FOXO3A, although interactions of AR with members of the forkhead family of transcription factors have been reported (Li et al., *Mol Cell Biol* 23: 104-118, 2003). Instead, AR may disrupt interactions between factors bound downstream and basal transcription factors bound to the core promoter, or between such factors and the co-activators they normally recruit.

Example 3

Differential Regulation of Muscle-Loss Genes by Testosterone and Oxandrolone

Studies with cultured muscle cells have shown that testosterone in physiological doses reduces levels of expression of MAFbx. This hormone was also found to suppress expression of the human MAFbx gene. Suppression requires the AR and is mediated by elements within or downstream of the core promoter. This suppression is also apparent with the anabolic steroid oxandrolone, though oxandrolone appears to be less effective in this regard. Testosterone reduced muscle breakdown in starved, cultured muscle cells, demonstrating a correlation between effects on MAFbx expression and ability to preserve muscle mass.

Testosterone is more effective in suppression MAFbx expression than oxandrolone. Similarly, in clinical studies, testosterone is more effective than the anabolic steroid nandrolone at restoring muscle mass, and appears to be more effective in suppressing muscle breakdown than oxandrolone. The relative abilities of testosterone and oxandrolone to suppress expression of a reporter gene under the control of 3.1 of the MAFbx upstream promoter has been evaluated. Testosterone (40% suppression at 500 nM) was more effective than oxandrolone (15% suppression at 5 µM) at reducing expression of this reporter after transfection into C2C12 muscle cells, demonstrating a differential response to these hormones by the MAFbx promoter (FIG. 11).

Example 4

Androgen Responsiveness of the IGF-1 Upstream Promoter

Recent pilot studies suggest that the anabolic steroid oxandrolone may improve respiratory function and speed wound healing in Spinal cord injury. Anabolic steroids of choice are typically androgen analogs with reduced virilizing activity.

They appear to preserve or increase muscle mass in many catabolic states. Their primary mechanism of action involves binding to and activation of the androgen receptor (AR), a ligand-activated transcription factor. The AR then modulates gene expression. Effects of androgens may be enhanced by release of second messengers. One such messenger is insulin-like growth factor-1 (IGF-1), which blocks breakdown of muscle proteins and promotes muscle hypertrophy. Some androgens (e.g., testosterone) stimulate release by skeletal muscle of IGF-1. The following studies identify two androgen response elements (AREs) that act synergistically to confer androgen, and to a lesser extent, glucocorticoid responsiveness of the IGF-1 promoter.

Plasmids:

pREP4.hAR, expressing full length human AR, and pCMV.Sport.β-Gal, expressing β-galactosidase under a CMV promoter, were as described (Zhao et al., *Steroids* 69: 357-366, 2004). pcDNA5.rGR, expressing rat glucocorticoid receptor, was provided by Dr. Diane Robins (University of Michigan). The rARC562G vector expressing rat AR with a C562G mutation in the DBD, which results in a loss of DNA binding.

ered with DMEM supplemented with 10% CDS-FBS and either hormone dissolved in ethanol, or ethanol, as indicated in the figures. Solutions of testosterone were prepared freshly on the day of the exeriment as preliminary studies indicated that this hormone began to loose activity in ethanol within 24 to 48 hours. After overnight incubation, activities of firefly and Renilla luciferase were determined using the Dual Luciferase Assay system (Promega).

Construction of Reporter Genes

Reporter plasmids expressing firefly luciferase under the control of upstream regions of the IGF-1 promoter were constructed by PCR amplification of segments of interest using primers shown in Table 2, using pOLuc-1630 as a template. The location of each amplified fragment is relative to the transcriptional start site. PCR amplification was conduced using a high fidelity Taq polymerase (Pfx, Invitrogen). PCR products were cloned into pCR2.1-TOPO TA (Invitrogen) and the sequences of the inserts were verified. Inserts were excised with Kpn I and Xho I, and were subcloned into pGL3-Promoter (Promega) at these same sites. PGL3-Promoter expresses firefly luciferase under the control of a minimal promoter.

TABLE 2

Amplification Primers for regions of the human IGF-1 upstream promoter.

| Construct | Forward Primer | Location | Reverse Primer |
|---|---|---|---|
| PGL3-230 | 5' ggtaccccaaagcctctcatgacac 3'<br>SEQ ID NO:35 | −1630 to −1402 | 5' gaaagaggaataagatatggtcaagtc 3'<br>SEQ ID NO:36 |
| PGL3-22 | 5' cacatgcccatcatatgactgtgaag 3'<br>SEQ ID NO:37 | −1508 to −1402 | 5' gaaagaggaataagatatggtcaagtc 3'<br>SEQ ID NO:38 |
| pGL3-32 | 5' gggcacatagtagagctcacaaaatg 3'<br>SEQ ID NO:39 | −1429 to −1250 | 5' tgagtcttctgtgtggttaatacattg 3'<br>SEQ ID NO:40 |
| pGL3-13a | 5' catagtgcaccattgacacaacat 3'<br>SEQ ID NO:41 | −1370 to −1250 | 5' tgagtcttctgtgtggttaatacattg 3'<br>SEQ ID NO:42 |
| pGL3-25a | 5' catagtgcaccattgacacaacat 3'<br>SEQ ID NO:43 | −1350 to −1250 | 5' tgagtcttctgtgtggttaatacattg 3'<br>SEQ ID NO:44 |

The IGF-1 reporter genes pOLuc.1630, pOLuc1300, pOLuc926, pOLuc 320 were provided by Dr. Peter Rotwein (Oregon Health & Science University). These reporters expressed firefly luciferase under the control of 320 to 1630 bases upstream of the transcriptional start site of the human IGF-1 promoter as described in (Kim et al., *Mol Endocrinol* 5: 1964-1972, 1991). pEGX 4T-1 hAR2, expressing GST fused to the N-terminus of AR DNA-binding domain, was provided by Robert J. Matusik, Ph.D. (Vanderbuilt University Medical Center). pRL-CMV expressing Renilla luciferase was from Promega (Madison, Wis.).

Cell Culture, Transfection, and Luciferase Assays

HepG2 cells (ATCC, Bethesda, Md.) were maintained in Dulbecco's modified Eagle's medium (DMEM), supplemented with 10% fetal bovine serum (FBS) and antibiotics (penicillin 100 U/ml, streptomycin 100 µg/ml). Cells were seeded at $5 \times 10^4$ cells/per well into wells of 24-well plates containing DMEM supplemented with 10% charcoal-dextran stripped FBS (CDS-FBS). The next day, cells were transfected with a total of 300 ng DNA per well using Lipofectamine Plus (Invitrogen) with plasmids as indicated in the figure legends. Three hours after transfection, cells were cov- GST-hAR DBD Expression and purification BL21:Des were transformed with pGEX 4T-1 hAR2, which encodes a GST-AR DNA-binding domain fusion protein under control of a Lac operon. A single colony was picked and grown at 37° C. overnight in LB broth (5 ml), then diluted 1:10 into 50 ml of this broth and grown 1 hour at 37° C. Isopropyl-β-D-thiogalactopyranoside was added at a final concentration of 1 mM. Cells were incubated for 2 hours at 20° C., collected by centrifugation (5000×g, 10 min, 4° C.) and frozen. Pellets were suspended in 0.5 ml of ice-cold phosphate-buffer saline to which was added 5 ml of lysozyme (10 mg/ml in water) followed by incubation on ice for 15 minutes. Ten µl of 1 M DTT and 70 µl 1% sarkosyl in phosphate buffered saline were added, and bacteria were disrupted by sonication. After centrifugation (16,000 RPM, 20 min, 4° C.), the supernatant was incubated (20° C., 30 min) with 1 ml of 50% (w/v) glutathione-agarose beads with gentle mixing. The beads were washed three times with 10 ml of ice-cold phosphate-buffer saline. The fusion proteins were eluted suspending the beads in 0.5 ml of 50 mM Tris-HCl (pH 8.0)

containing 15 mM reduced glutathione followed by incubation at 20° C. for 4 min) followed by centrifugation. Protein was stored at 4° C. until use.

Electrophoretic Mobility Shift Assays

The forward sequence of the oligonucleotide probe for ARE2 was 5'-TTGTAGTTGGGCACATAGTAGAGCTCA-3' (SEQ ID NO:23), that for the probe for ARE1 was 5'-GACTTGACCATATCTTATTCCTCTTTG-3' (SEQ ID NO:24), and that for SRE was 5'-ATGCATTGGGTACATCT-TGTTCACATA-3' (SEQ ID NO:25). Synthetic sense and antisense strands (lacking YZ bases from the 3' terminus) were annealed then end-labeled with 32p dCTP by filling in the ends using the Klenow fragment of E. coli DNA polymerase in the presence of dNTPs at 37 C. for 30 minutes. Probes were purified using ProbeQuant G-50 Micro Columns (Amersham) and eluted from the columns water.

The analysis was initiated by determining whether the IGF-1 upstream promoter contained androgen responsive elements. HepG2 cells were transfected with a reporter gene expressing firefly luciferase under the control of 1.6 kb of the upstream promoter of the human IGF-1 gene. While HepG2 cells are reported to express AR, the level of expression is below that needed to achieve testosterone-induced induction of reporters with known AREs such as MMTV-Luc. Accordingly, cells were co-transfected with either a vector expressing the human AR or one expressing β-galactosidase, then incubated overnight with testosterone or vehicle, and assayed for luciferase expression. Testosterone had no effect on luciferase expression in cells co-transfected with β-galactosidase, but caused a significant increase in expression in cells expressing AR (FIG. 12). These data indicate the presence of androgen-responsive elements within the first 1.6 kb of the IGF-1 upstream promoter.

To localize the androgen responsive elements, this analysis was repeated with a series of reporter genes with 5' truncations that removed between 300 and 1200 bases from the 5' end of the original 1.6 kb insert. Androgen responsiveness was lost completely with removal of 300 bases from the 5' terminus of the insert, and was not restored by additional 5' truncations (FIG. 13). The findings indicate that the androgen responsive elements are localized to between −1300 and −1600 bases upstream of the first codon of the IGF-1 gene.

Inspection of the sequence of this region of the IGF-1 gene revealed two regions resembling those of the half-sites of the AREs of the Pem homeobox gene (Barbulescu et al., Mol Edocrinol 15: 1803-1816, 2001). However, precise alignment of Pem AREs with similar sequences of the human IGF-1 gene was not possible, primarily because for each potential half-site, no second site was found at an appropriate spacing from the first. Instead, the androgen-responsive region of the IGF-1 promoter consisted of two clusters of overlapping half-sites similar to the consensus TGTTTGT sequence, each paired with a half-site with low identity to the consensus steroid hormone receptor binding sequence. The clusters were located at approximately −1420 (ARE1) and −1380 (ARE2) bases upstream of the first codon. The first cluster (ARE1) contained two overlapping half-sites, ACTTGA and TGACCA, each with downstream sequences that bore only a weak resemblance to known AR binding sites. A third sequence within this region, ATATCTtatTCCTCT (SEQ ID NO:18), contained one half site downstream of an incomplete half-site, and bore some resemblance to the first element from the Slp gene (GTAATTatcTGTTCT; SEQ ID NO:19) (Adler et al., Mol Endocrinol 5: 1587-1596, 1991), and the JRE element ATTACAccaAGTACC (SEQ ID NO:20; Clay et al., J Biol Chem 268: 13556-13564, 1993). Sequences of this ARE overlapped those of the other two in the ARE1 cluster.

The second likely ARE also contained two overlapping half-sites. The first, ACATAGtagAGCTCA (SEQ ID NO:21), included on its right side a half-site very closely resembling the right-hand half-site of the Pem2 ARE, TGCTCA. The second, GCACATagtAGAGCT (SEQ ID NO:22), was less related to known AREs. Its right half-site resembled the consensus SRE, whereas its left-half site was again quite divergent.

To explore the possibility that these sequences represent authentic AREs, additional reporter genes were constructed such that they were under the control of sequences containing ARE1, ARE2, or both. Cells were then transfected with these reporter genes together with AR, and effects of incubation with testosterone on reporter gene activity was determined as shown in FIG. 14. In cells transfected with reporter genes with inserts that included ARE1 (pGL3-230, pGL3-22), testosterone led to more than 5-fold increases in expression of luciferase. When cells were transfected with a construct containing ARE2 (pGL3-13A), testosterone increased expression by more than 20-fold. The greatest induction was observed when cells were transfected with a reporter gene with an insert containing both ARE1 and ARE2 (pGL3-32). Little androgen responsiveness was observed when cells were transfected with a reporter under control of 100 bases beginning just downstream of ARE2 (pGL3-25a). These data indicate the presence of strong androgen-responsive elements located between −1420 and −1320 upstream of the first codon of the IGF-1 gene.

The greater testosterone responsiveness of constructs containing both ARES as opposed to either one alone indicated the possibility of synergistic interactions between the two elements. To test for synergism more explicitly, cells were transfected with reporter genes under the control of ARE1, ARE2, or both then incubated with increasing doses of testosterone (FIG. 15). These data revealed large differences in the maximal luciferase expression induced by testosterone as well as in sensitivity of the different constructs to activation by testosterone. The construct containing ARE1 (pGL3-230) reached the lowest plateau, at approximately 8-fold induction, and was the least sensitive to testosterone, with induction of luciferase expression occurring at relatively high doses beginning at 0.25 nM. By contrast, the construct containing both AREs (pGL3-32) reached the highest plateau (25-fold) and was quite sensitive to testosterone, with nearly 10-fold induction at the lowest concentration tested (0.05 nM). The construct containing ARE2 (pGL3-13A) was intermediate in its maximal induction and sensitivity. The data indicate the existence of synergistic interactions between the two AREs.

To determine whether these effects of androgens depended upon binding of the AR to specific DNA sequences within these two elements, the ability of testosterone to induce expression of reporter genes containing them was tested in cells transfected with a mutant AR with impaired DNA binding due to a C->G mutation in fourth cysteine of the first zinc finger within the DNA binding domain (AR-C562G) (Aamisalo et al., Endocrinology 140: 3097-3105, 1999). Cells were co-transfected with a vector expressing the mutant AR, and reporter genes containing ARE1 (pGL3-22), ARE2 (pGL3-13A) or both (pGL3-32). As a control, additional experiments were conducted in which cells were co-transfected with these reporters and a vector expressing wild-type AR. For each of the three vectors tested, induction of luciferase expression was virtually abolished when wild-type AR was replaced with the DBD mutant (FIG. 16), consistent with a requirement for binding of AR to DNA sequences within ARE1 and ARE2 for transactivating activity.

In order to more directly test whether the AR bound to sequences with ARE1 and ARE2, binding of a GST-tagged version of recombinant AR DNA-binding domain to radiolabeled probes was examined using electrophoretic mobility shift assays. Incubation of the AR-DBD with probes having the steroid response element consensus sequence (SRE) yielded a strong band that was greatly diminished by the addition of excess unlabeled probe (FIG. 16B). Incubation with a probe including the sequence of the putative IGF-1 ARE1 yielded a band with a similar mobility though of lesser intensity (FIG. 16B) which was absent when the AR was omitted. Intensity of this band was diminished when excess cold SRE DNA was added. Incubation of the AR-DBD with a probe including the sequence of the IGF-1 ARE2 also yielded a band with mobility similar to that for complexes formed between AR and SRE (FIG. 16B). The intensity of this band was consistently weaker than that for complexes with SRE. While the intensity of the band for ARE2 was less than that for ARE1 in the experiment shown, this pattern may not reflect any specific feature of complex formation as the relative intensities of these two bands varied among several experiments. Addition of excess, unlabeled SRE greatly diminished the intensity of the band observed with labeled ARE2 (FIG. 16B). These findings indicate specific binding of the IGF-1 ARE1 and ARE2 to the AR-DBD, consistent with the interpretation that these DNA sequences represent cis-acting elements bound by the AR.

Additional experiments determined whether the GR mediated transcriptional activation via the AREs within the IGF-1 promoter. Experiments determined the ability of dexamethasone to activate reporter genes in HepG2 cells co-transfected with a vector expressing the GR, and compared expression to that induced by testosterone in cells co-transfected with a vector expressing AR. Dexamethasone induced only weak induction of luciferase expression (less than 2-fold) in cells transfected with reporter genes incorporating ARE1 (p3-230 and p3-22 in FIG. 17) as compared to more than 5-fold increases observed in cells treated with testosterone. Stronger activation (5-fold) was observed for the reporters incorporating ARE2, or both AREs (p3-13a and p3-32, respectively), although activation remained more than 5-fold less than that observed for cells transfected with the same reporter genes and treated with testosterone (approximately 20- and 30-fold, respectively).

In contrast to testosterone, anabolic steroids such as oxandrolone that do not induce muscle release of IGF-1 in clinical studies appear not to induce IGF-1 in the reporter model system. This model system also shows that the human IGF-1 gene is upregulated by androgens through the binding of AR to its cognate binding sites in the upstream promoter region of this gene. Oxandrolone does not induce IGF-1 at comparable concentrations as shown in FIG. 18.

These findings indicate that modulation of IGF-1 expression by androgens is attributable to the two AREs identified by these analysis and are consistent with the modulation by androgens of IGF-1 expression in muscle reported in several clinical studies. In elderly men with low testosterone levels, testosterone replacement therapy increased skeletal muscle levels of IGF-1 mRNA and protein (Ferrando et al., *Am J Physiol Endocrinol Metab* 282: E601-E607, 2002; Urban et al., *Am J Physiol* 269: E820-E826, 1995), while in young men, ablation of testosterone production significantly reduced levels of IGF-1 mRNA in skeletal muscle (Mauras et al., *J Clin Endocrinol Metab* 83: 1886-1892, 1998). Moreover, treatment of animals with the testosterone analog nandrolone increased IGF-1 expression (Lewis et al., *Am J Physiol Endocrinol Metab* 282: E483-E490, 2002; Gayan-Ramirez et al., *J Appl Physiol* 88: 26-34, 2000) in diaphragm muscle. Changes in IGF-1 expression in these clinical studies are on the order of 2-fold, similar to that observed with the pOLuc. 1630 reporter, containing 1600 bases of the IGF-1 promoter upstream of the first codon, and much smaller change than the more than 10-fold increase in luciferase activity of reporter genes incorporating sequences for the two AREs and their flanking sequences, but lacking most downstream sequences of the IGF-1 promoter. These findings indicate that down stream sequences are capable of attenuating the androgen responsiveness of the IGF-1 AREs.

The weak activity of GR at the AREs of the IGF-1 gene are consistent with the net physiological effect of glucocorticoids on IGF-1 levels and expression. Glucocorticoids diminish IGF-1 expression and reduce blood and, presumably, tissue levels of this hormone. Glucocorticoids have been reported to suppress IGF-1 expression due to transcriptional repression via CAAT/enhancer binding proteins bound to the sequences located at +132 to +158 downstream of the first transcription site (Delany et al., *Mol Endocrinol* 15: 1781-1789, 2001; Delany et al., *Endocrinology* 136: 4776-4781, 1995). It therefore appears that the repressive effects mediated by CAAT/enhancer binding proteins is much greater than any activation that occurs as a result of binding of GR to the AREs identified above. Indirect evidence suggests that this is not the case when these elements are bound by AR. For example, the anabolic steroid nandrolone, which is a derivative of testosterone, increases IGF-1 mRNA levels in the diaphragm of glucocorticoid-treated animals. Moreover, testosterone administration largely reverses repression of IGF-1 mRNA levels induced in skeletal muscle by glucocorticoids.

Example 5

Androgens Attenuate Increased Expression of MAFbx in Acutely Denervated Muscle Without Preventing Atrophy Denervation induces rapid muscle atropyhy due to accelerated catabolism of muscle proteins that has been linked to increased expression of MAFbx as well as the Muscle Ring Finger protein MuRF1. Anabolic steroids reduce muscle atrophy due to disuse from immobilization, microgravity, or spinal cord injury (SCI). To determine whether anabolic steroids block muscle loss due to denervation and to assess the molecular effects of anabolic steroids, MAFbx and other genes involved in muscle homeostasis were examined following acute denervation with or without administration of the anabolic steroid nandrolone.

Animals:

Male Wistar rats weighing 250 gm (Taconic Farms, Germantown, N.Y.) were provided food and water ad libitum and were housed in a temperature and humidity controlled environment providing a 12:12 hour day-night cycle. For surgical procedures, animals were anesthetized with ketamine/xylazine. The left sciatic nerve was exposed by blunt dissection, and a 1 to 2 mm piece of this nerve was excised just below the level of the femoral head. A sham surgery was performed on the right hind limb in which the sciatic nerve was exposed but was not transected. Model 2002 Alzet pumps were implanted subcutaneously on the back. Pumps administered a continuous infusion of either vehicle (50% DMSO in propylene glycol, 200 µl over 14 days) or nandrolone (1.5 mg/kg/wk, Sigma Chemical Co., St. Louis, Mo.). A pellet containing 15 mg of testosterone (Innovative Research of America, Sarasota, Fla.) administered as a continuous infusion (5 mg/wk), or a pellet containing placebo, was inserted into a subcutaneous pouch. This administration of exogenous testosterone was performed to control for known effects of nandrolone and other anabolic steroids to depress endogenous testosterone levels (Clark et al., *Horm Behav* 31: 35-46, 1997; Daniell et al., *J Pain* 3: 377-384, 2002; Grokett et al., *Acta Endocrinol (Copenh)* 126: 173-178, 1992). Because testosterone is known to have anabolic actions (Ferrando et al., *Am J Physiol Endocrinol Metab* 282: E601-E607, 2002; Mauras et al., *J Clin Endocrinol Metab* 83: 1886-1892, 1998; Urban et al., *Am J Physiol* 269: E820-E826, 1995), reductions in levels of this hormone could affect muscle mass and confound interpretation of the results. Animals were euthanized 14 days later by inhalation of carbon dioxide. Following removal of blood from the left ventricle for determination of serum testosterone concentration by radioimmunoassay (MP Biomedicals, Costa Mesa, Calif.), soleus, extensor digitorum longus (EDL), gastrocnemius and plantaris muscles were excised and weighed, then were flash frozen on dry ice and stored at −80° C.

Real Time PCR.

Total RNA was extracted from skeletal muscle (20 mg) by homogenization in guanidine thiocyanate using a Polytron followed by extraction using phenol-chloroform (Chomczynski and Sacchi, *Anal Biochem* 162: 156-159, 1987). Total RNA was further enriched using RNAeasy minicolumns (Qiagen, Valencia, Calif.) and treated with RNAse-free DNAse (Qiagen). Total RNA was then eluted and quantified by absorbance at 260 nm. One µg of total RNA was used to prepare a cDNA library by reverse transcription (iScirpt, Biorad, Hercules, Calif.). Libraries were diluted 1:25 with water prior to real time PCR. Real time PCR was conducted using an ABI 7500 real time PCR thermal cycler, ABI 2×PCR reagent, and ABI Taqman real time PCR probes for genes of interest. Levels of gene expression in the denervated muscle were expressed as fold induction relative to muscle from the sham-denervated leg of animals administered vehicle. This approach was taken to eliminate confounding effects of nandrolone on gene expression in normal muscle (see results). Fold-induction was determined using the $2^{-\Delta\Delta Ct}$ method, using expression of 18S RNA as the normalization control. Primers and probes used for 18S RNA, MuRF1 and myostatin were obtained through the assays by Design service of Applied Biosystems and had the sequences are shown in Table 2; probes were 5' labeled with FAM and 3' modified with a non-fluorescent quencher. All other primer-probe combinations used were those contained in ABI Assay on Demand kits.

Statistics:

Data are expressed as mean values±SEM. Statistical analysis was performed using one-way ANOVA with a Newman-Keuls multiple comparisons test post-hoc. Values for p of <0.05 were considered significant.

To test the possibility that anabolic steroids could reduce muscle loss due to denervation, nandrolone or vehicle was administered to rats for 14 days after the sciatic nerve transection, at which time animals were euthanized. Nandrolone was administered at a dose of 1.5 mg/kg/wk (corresponding to a high dose for humans following FDA-approved usage). Animals receiving nandrolone also were administered testosterone replacement therapy to control for effects of reductions in testosterone levels often observed with anabolic steroid treatment (Clark et al., *Horm Behav* 31: 35-46, 1997; Daniell et al., *J Pain* 3: 377-384, 2002; Grokett et al., *Acta Endocrinol (Copenh)* 126: 173-178, 1992). Weights of muscles from sham-transected limbs tended to be increased by nandrolone (FIG. 19), although this difference was not statistically significant. This trend was particularly apparent for plantaris and gastrocnemius. Changes in weights of denervated muscles were expressed as a percentage of weights for corresponding muscles from the sham-denervated limb of animals administered placebo to eliminate confounding effects of such nandrolone effects on normal muscle. The weights of muscles from the denervated limb of animals administered nandrolone were not significantly different from those for animals administered vehicle (FIG. 19), indicating no effect of nandrolone on overall muscle atrophy secondary to denervation during the period immediately (0-14 days) following surgical transection. To test whether higher doses of nandrolone might be more effective, additional animals were administered nandrolone at doses of 7.5 or 37.5 mg/kg/week following the same protocol. No effect of nandrolone treatment on atrophy was observed at either dose.

Levels of MAFbx mRNA were significantly elevated in denervated muscle (FIG. 20A). Relative increases in expression caused by denervation were approximately 3-fold greater for soleus as compared to EDL. Nandrolone significantly reduced MAFbx expression in denervated soleus, though levels remained significantly greater than those in the sham-transected limb of placebo animals. Nandrolone appeared to reduce expression of MAFbx in denervated EDL though reductions were not statistically significant, and levels remained significantly greater than those in sham-denervated muscle of placebo animals. Nandrolone did not significantly alter expression of MAFbx in sham-denervated EDL or soleus in the two weeks following denervation.

Denervation significantly elevated MuRF1 expression in EDL and soleus (FIG. 20B). Similar increases were observed in EDL and soleus. Nandrolone significantly reduced MuRF1 expression in EDL. It appeared that nandrolone did not completely normalize levels of MuRF1 mRNA in denervated EDL, though this trend did not reach statistical significance. Nandrolone significantly decreased MuRF1 expression in denervated soleus, though levels remained significantly greater than those in sham-denervated placebo animals. Nandrolone did not significantly affect MuRF1 expression in sham-denervated soleus or EDL.

Expression of IGF-1 was not altered in denervated EDL (FIG. 21A). Levels of IGF-1 expression appeared increased in denervated soleus, but this trend was not significant. Administration of nandrolone significantly reduced expression of IGF-1 in denervated EDL, as well as in sham-denervated EDL. Nandrolone did not significantly affect expression of IGF-1 in denervated or sham-denervated soleus.

Denervation significantly increased IGF-1 receptor (IGF-1R) mRNA levels in denervated EDL and soleus (FIG. 21B). This elevation is similar to that reported in SCI rats (Haddad et al., *J Appl Physiol* 95: 791-802, 2003). While nandrolone tended to increase IGF-1R expression in sham-denervated soleus and EDL, these changes were not significant. No appreciable effects of nandrolone on expression of the IGF-1R were observed in denervated soleus or EDL.

Denervation led to significant reductions in expression of myostatin in EDL (approximately 50%), and a trend toward reduced expression in soleus (FIG. 22A). This finding is consistent with a prior report of reduced myostatin protein levels in denervated muscle (Sakuma et al., *Biochem Biophys Acta* 1497: 77-88, 2000). Nandrolone appeared to reduce myostatin expression in denervated EDL, and significantly reduced expression of this gene in sham-denervated EDL.

Nandrolone did not appreciably alter expression of myostatin in soleus (FIG. 22A). Denervation did not significantly alter AR expression. Nandrolone did not alter AR expression in denervated or sham-denervated soleus or EDL (FIG. 22B).

Levels of junB mRNA were markedly elevated in denervated soleus and EDL (FIG. 23A). This increase is similar to that reported previously for denervated muscle (Abu-Shakra et al., Brain Res Mol Brain Res 18: 216-220, 1993). The increase in expression was nearly twice as large for EDL as compared to soleus. Nandrolone significantly reduced junB expression in denervated EDL. Levels of junB expression in denervated EDL from nandrolone animals appeared to remain elevated as compared to sham-denervated EDL from placebo animals, though this trend did not reach significance. Nandrolone tended to reduce junB expression in denervated soleus muscle, though levels remained significantly greater than those in sham-denervated muscle from placebo animals. Nandrolone tended to increase junB expression by approximately 2-fold in soleus and EDL from sham-denervated limbs of placebo animals.

Expression of myogenin was greatly increased by denervation (FIG. 23B). Levels were similar in denervated soleus and EDL. Nandrolone reduced myogenin expression in denervated soleus to 70% of that in denervated muscle from placebo animals, a level remaining significantly greater than expression in sham-denervated muscle from placebo animals. Nandrolone reduced myogenin expression in sham-denervated soleus by 50%, though this trend did not reach significance. Nandrolone tended to reduce expression in denervated EDL, and appeared to diminish expression in sham-denervated EDL by 50%, though neither difference reach statistical significance.

Similarly, GADD45 expression was strikingly increased in denervated EDL and soleus (FIG. 23C). This marked upregulation of GADD45 has been described in other studies of denervation atrophy (Machida & Booth, Acta Physiol Scand 183: 171-179, 2005). Nandrolone caused a modest (21%) though significant reduction in GADD45 expression in denervated EDL and a larger (40%), and significant, decrease in denervated soleus. Nandrolone tended to reduce myogenin expression in sham-denervated soleus and EDL (48 and 27%, respectively) though these trends did not reach significance.

The findings indicate that treatment with nandrolone for two weeks following surgical transection did not reduce atrophy due to denervation. Muscle atrophy during the first two weeks after denervation is primarily due to accelerated degradation of muscle proteins (Furuno et al., J Biol Chem 265: 8550-8557, 1990; Medina et al., Biomed Biochem Acta 50: 347-356, 1991). Thus, the inability of nandrolone to block atrophy during this period of rapid catabolism indicates that nandrolone was unable to diminish protein breakdown.

Quite different findings were observed when other forms of disuse atrophy were treated with testosterone or anabolic steroids. In rats, both testosterone and nandrolone have been shown to greatly reduce atrophy due to hindlimb suspension for 12 days (Wimalawansa et al., J ppl Physiol 86: 1841-1846, 1999). Similarly, testosterone significantly reduced atrophy during the initial two weeks after SCI in rats (Gregory et al., Spinal Cord 41: 23-28, 2003). A more complex effect of nandrolone has been reported for atrophy due to immobilization in rabbits, where atrophy was not affected during the initial two weeks of nandrolone administration, but was reversed after 8 weeks of administration (Taylor et al., Am J Sports Med 27: 718-727, 1999).

The lack of effect of nandrolone on denervation atrophy despite significant effects of nandrolone on reducing expression of MAFbx and MuRF1 indicating that the magnitude of such reductions is not sufficient to slow acute denervation atrophy. Alternatively, the relationship between levels of these factors and rates of atrophy may not be tightly coupled, although further reductions below some threshold level may have a benefit. Based on the expression profiles of other genes implicated in muscle hypertrophy, the findings described above demonstrate that the failure of nandrolone to inhibit muscle atrophy was not due to a deficit in signaling by AR. However, the inability of nandrolone to stimulate expression IGF-1 or its receptor may have contributed to its lack of efficacy in acute denervation. Administration of exogenous IGF-1 has been found to block denervation atrophy (Stitt et al., Mol Cell 14: 395-403, 2004). IGF-1 has been found to be expressed at increased levels in diaphragm muscle after nandrolone administration (Gayan-Ramirez et al., J Appl Physiol 88: 26-34, 2000; Lewis et al., Am J Physiol Endocrinol Metab 282: E483-E490, 2002).

Example 6

Androgens Suppress Increased Expression of MAFbx and Attenuate Muscle Loss Following Chronic Denervation To further elucidate the effects of anabolic steroids during chronic denervation, the expression of MAFbx and other genes involved in muscle homeostasis was evalusted in chronically denervated muscles.

Animals:

Male Wistar rats weighing 200-250 gm (Taconic Farms, Germantown, N.Y.) were provided food and water ad libitum and were housed in a temperature and humidity controlled environment providing a 12:12 hour day-night cycle. For surgical procedures, animals were anesthetized with ketamine/xylazine. The left sciatic nerve was exposed by blunt dissection, and a 1 to 2 mm piece of this nerve was excised just below the level of the femoral head. A sham surgery was performed on the right hind limb in which the sciatic nerve was exposed but was not transected. Twenty eight days later, animals were anesthetized, and Alzet pumps were implanted subcutaneously on the back. Pumps administered a continuous infusion of either vehicle (propylene glycol) or nandrolone (0.75 mg/kg/wk, Sigma Chemical Co., St. Louis, Mo.) plus testosterone (0.7 mg/day, Sigma) until the time of sacrifice. Administration of exogenous testosterone was performed to control for known effects of nandrolone and other anabolic steroids to depress endogenous testosterone levels. Testosterone levels after replacement were approximately 15 nM, a high-normal range for rats of this age. Animals were sacrificed 3, 7 or 28 days after implantation of the miniosmotic pumps by inhalation of carbon dioxide. Gastrocnemius muscles were excised and weighed, then flash frozen on dry ice and stored at −80° C.

Real Time PCR.

Total RNA was extracted from skeletal muscle (20 mg) by homogenization in guanidine thiocyanate using a Polytron followed by extraction of total RNA with phenol-chloroform as described by (Chomczynski and Sacchi, Anal Biochem 162: 156-159, 1987). Total RNA was further enriched using RNAeasy minicolumns (Qiagen, Valencia, Calif.). This procedure included digestion of contaminating DNA on the column with RNAse-free DNAse (Qiagen). Total RNA was eluted and quantified by absorbance at 260 nm. One µg of total RNA was used to prepare a cDNA library by reverse transcription (High Capacity cDNA Archive Kit, Applied Biosystems). Libraries were diluted 25-fold with water. Real time PCR was performed Taqman 2×PCR buffer (Applied Biosystems) using an Applied Biosystems 7500 thermocycler. Levels of gene expression in the denervated muscle were expressed as fold induction relative to muscle from the sham-denervated leg of animals administered vehicle. This approach was taken to eliminate confounding effects of nandrolone on gene expression in normal muscle (J. Zhao et al, submitted). Fold-induction was determined using the $2^{-\Delta\Delta Ct}$ method, using expression of 18S RNA as the normalization control. Primers and probes used for 18S RNA, MuRF1 and myostatin were obtained through the assays by Design service of Applied Biosystems and had the sequences are shown in Table 3; probes were 5' labeled with FAM and 3' modified with a non-fluorescent quencher. All other primer-probe combinations used were those contained in ABI Assay on Demand kits.

TABLE 3

Sequences of primers and probes for real-time PCR.

| Gene | Sequences | |
|---|---|---|
| Myostatin | Forward: | |
| | GAGAGAGAGGCGAATGTGGAAAA | (SEQ ID NO:26) |
| | Reverse: | |
| | GCTTCTATTCTGGAGTACCTTGTGT | (SEQ ID NO:27) |
| | Probe: | |
| | ACGCACACGCATTACA | (SEQ ID NO:28) |
| MuRF1 | Forward: | |
| | CGACCGAGTTCAGACTATCATCTC | (SEQ ID NO:29) |
| | Reverse: | |
| | GTGGCTCAGTTCCTCCTTCAC | (SEQ ID NO:30) |
| | Probe: | |
| | CTGTTTTCCTTGGTCACTCG | (SEQ ID NO:31) |
| 18S RNA | Forward: | |
| | CGCAGCTAGGAATAATGGAATAGGA | (SEQ ID NO:32) |
| | Reverse: | |
| | GGCCTCAGTTCCGAAAACCAA | (SEQ ID NO:33) |
| | Probe: | |
| | CCGCGGTTCTATTTTG | (SEQ ID NO:34) |

Statistics

Data are expressed as mean values±SEM. Values for p of <0.05 were considered significant.

Muscle Weights

Weights of the gastrocnemius muscles are shown in FIG. 24. During this period, muscles of the intact limb grew in size by 23%, consistent with usual growth of rats of this age. Administration of nandrolone tended to increase the mass of muscles in the normal limb by 2-5%, although this difference did not reach significance (at 56 days, p<0.40, t-test). Denervation resulted in severe atrophy. As compared to muscle from the normal limb, that from the denervated limb was reduced in mass by 76% after 31 days, 80% after 35 days, and 88% after 56 days, indicating that loss progressed over the second month after denervation. Weights of muscles of animals administered nandrolone were similar after 3-days of nandrolone administration (31 days after nandrolone). By 7 days however, weights for denervated muscles from animals administered nandrolone were greater by than weights for animals administered vehicle (116%), and this effect increased with more prolonged administration of nandrolone to reach 130% after 28 days administration of this drug (56 days after denervation). Analysis of these data by two way ANOVA indicated significant effects of both drug and time. Thus, nandrolone significantly reduced muscle loss during chronic denervation atrophy.

Catabolic Factors

To gain insights into how nandrolone achieved this beneficial effect, additional studies were performed that assessed effects of nandrolone on expression of genes known to be linked to muscle catabolism or muscle hypertrophy. Effects of nandrolone on expression of genes for the ubiquitin ligases MAFbx and MuRF1, and of myostatin, are shown in FIG. 25. Expression of MAFbx was elevated by at least 50% in denervated muscle at all time points. Nandrolone did not alter expression of this gene in sham-denervated muscle. MAFbx expression remained 2-fold elevated in denervated muscle over the period between 35 and 56 days after denervation, and did not appear to diminish over this time. Expression of MAFbx tended to be reduced after 7-days infusion of nandrolone (35-days after denervation) and was significantly reduced after administration of this drug for 28 days, at which time MAFbx expression was reduced by 35%. It was noteable that the time-course of nandrolone-induced changes in MAFbx expression paralleled the effect of nandrolone to preserve muscle in the denervated limb.

Expression of MuRF1 was increased by 2-fold in denervated muscle between 31 and 56-days after denervation, and did not appear to diminish in expression over this period. Nandrolone significantly reduced expression of MuRF1 after 7-days administration, and this effect persisted through 28-days. Expression of MuRF1 was reduced by 31 and 37% at these time points, respectively. Infusion of nandrolone had no effect on expression of MuRF1 in muscle of sham-denervated hindlimbs. The time-course of these effects of nandrolone on MuRF1 expression paralleled the effects of nandrolone on the weights of the denervated muscle.

Myostatin expression was markedly reduced in denervated muscle, being reduced to one third of baseline at 31 days after denervation, with a further reduction to approximately 20% of baseline at 56 days after denervation. Nandrolone administration caused a further modest, though significant reduction in expression of this gene after 7 and 28 days administration. Of interest, expression of myostatin also tended to be decreased in sham-denervated muscle from nandrolone-treated animals, though the differences did not reach significance.

IGF-1 System

Nandrolone did not alter IGF-1 expresion in sham-denervated muscle (FIG. 26). Expression of IGF-1 was elevated by approximately 2-fold over the period from 31 to 56 days after denervation. Nandrolone administration did not alter expression of this gene. Expression of the IGF receptor was also increased over the period between 31 and 56 days, in this case by 2.5 fold. Nandrolone infusion did not alter expression of IGF-receptor at early time points, but a trend toward increased expression of the receptor was observed after 28 days (p<0.10). Expression of the IGF-1 receptor in sham-denervated muscle was not altered by nandrolone.

Additional studies assessed effects of nandrolone on IGF-binding proteins. Because these IGFBPs might be expressed at different levels in muscle, and because expression levels would be predicted to provide information about the importance of any changes observed, the initial analysis determined the relative levels of expression of mRNAs, for IGFBP2, 3, 4 and 5 in comparison to that for 18S RNA (FIG. 27, top panel). In sham-denervated muscle, expression IGFBP-5 was greatest, while that of IGFBP-4 was also high, though approximately 7-fold lower than that of IGFBP-5. Expression of IGFBP-3 was approximately 30-fold lower than that of IGFBP-5, whereas that of IGFBP-2 was quite low, being 1000-fold lower than that for IGFBP-5. Thirty-one days after denervation, expression of each of these binding proteins was significantly elevated.

After denervation, mRNA for IGFBP-5 remained the most abundant, with levels for IGFBP-3 and -4 being 12- and 6-fold lower levels, respectively. The largest increase in expression of IGFBPs was for IGFBP-2, which increased in expression by 22-fold at 31 days (FIG. 27), although even after this large increase in expression, expression of this gene continued to be lower than that of the other binding proteins tested, and was expressed at levels approximately 300-fold lower than for IGFBP-5. Expression of IGFBP-3 increased by somewhat more than 2-fold, while that of IGFBP-4 and -5 increased by 3-4 fold, and 5-fold, respectively. Expression of IGFBP-2 and 5 in denervated muscle tended to decrease over time, (FIG. 27), while that of IGFBP-3 and -4 appeared to be persist at the same, elevated level of expression over the entire period from 31 to 56 days.

Nandrolone did not appreciably alter expression of any of the IGFBPs in sham-denervated muscle. It also did not significantly alter expression of IGFBP 2, 4 or 5 at any time tested. Nandrolone significantly reduced expression of IGF-BP-3 at 56-days, and tended to reduce expression of IGFBP-5 at this time point. Unexpectedly, expression of IGFBP-2 and 4 appeared somewhat increased by nandrolone in denervated muscle, although these changes did not reach significance.

Transcriptional Regulators

Effects of chronic denervation and nandrolone on expression of transcriptional regulators is shown in FIG. 28. Expression of myogenin was elevated more than 10-fold at all time points, and remained 20-fold elevated even at 35 and 56 days after denervation. Nandrolone did not alter expression of this gene within the first 7-days after starting its administration, but significantly elevated (approximately 2-fold) myogenin expression by day 28 of the infusion. By contrast, nandrolone significantly reduced myogenin expression in denervated muscle after 28-days infusion of this drug. Expression fell by 32% but remained more than 12-fold greater than that in sham-denervated muscle. No effects of nandrolone on myogenin expression were observed after 3 or 7-days administration of this drug.

Expression of GADD45 was increased by 17-fold in denervated muscle 31-days after denervation, and, 56-days after denervation, declined with time to levels 9-fold greater than those in sham-denervated muscle. Nandrolone had no appreciable effect on expression of GADD45 in sham-denervated muscle. Infusion of nandrolone tended to reduce expression of this gene after 3 and 7-days, though these effect did not reach significance, and was lost after 28-days nandrolone infusion.

Expression of junB was increased 6-fold in denervated muscle at 31-days after transection, and remained elevated to a similar degree up to 28-days later. Nandrolone had no effect on expression of this gene in sham-denervated muscle. This drug tended to reduce expression of junB in denervated muscle at all times from 3 to 28 days after starting infusion, although these differences Nandrolone significantly reduced muscle atrophy in the context of chronic denervation. Although nandrolone preserved skeletal muscle during denervation atrophy, protection against continued atrophy afforded by nandrolone was only partial, and some continued atrophy appeared to occur. This is consistent with findings that even with testosterone administration to rats with SCI, animals lost approximately 50% of their muscle mass over the 11 week period of evaluation. Similarly, administration of nandrolone resulted in significant preservation of muscle in rats subjected to microgravity (Wimalawansa et al., *J Appl Physiol* 86: 1841-1846, 1999), or rabbits immobilized with casts (Taylor et al., *Am J Sports Med* 27: 718-727, 1999). Collectively, the findings indicate a general ability of anabolic steroids to preserve skeletal muscle mass during disuse.

The protection afforded by nandrolone against chronic denervation atrophy is quite different from effects of this agent during acute denervation as described above. This difference in effects depending on the temporal stage following denervation suggest that there is a change in muscle receptiveness to anabolic steroids as atrophy proceeds from acute to subacute or chronic. The change in responsive does not appear to be due to changes in expression of the gene for the androgen receptor (AR), the receptor activated by nandrolone, because expression levels for this gene remain unaltered in muscle after acute or chronic denervation. Differences between the acute and chronic denervation include the degree of atrophy present, and presumably, the rates of catabolism of muscle proteins acutely. Between 40 and 60% of muscle mass is lost within the first two weeks after denervation, whereas 80% of muscle mass is lost by 28 days. Muscle loss during the acute phase of atrophy is primarily due to accelerated catabolism of muscle proteins, and, by inference, the greatest rates of catabolism occurs within the first several weeks. During this period, rates of muscle protein catabolism are increased up to 4-fold. Other evidence of differences in muscle responses to nandrolone over time after denervation are evident upon comparison of the results of nandrolone administration during the acute and chronic phases following denervation. For example, nandrolone had no effect on expression of GADD45 at any time point in chronic denervation, whereas it caused significant reductions in expression of this gene in acute denervation.

Elevation of expression of MAFbx and MuRF1 was persistent despite the fact that by 2 months, more than 90% of gastrocnemius muscle had been catabolized. This finding, and the persistant elevation of myogenin and GADD45, are in agreement with findings from previous microarray analysis of denervated EDL muscle studied from 1 to 3 months after denervation (Magnusson et al., *Eur J Neurosci* 21: 577-580, 2005; Batt et al., *Faseb J* 2005; Kostrominova et al., *Physiol Genomics* 22: 227-243, 2005). In addition, several other persistent changes were observed that were not detected by microarray analysis. These included persistent elevations in expression of IGF-1, IGF-receptor, and IGFBP3, 4 and 5, as well as more transient elevations in expression of IGFBP2. The persistent elevation of GADD45, which diminishes apoptosis due to denervation, is likely to be protective. The concept of increased expression of specific genes encoding proteins with protective actions has also been advanced based upon findings that the increased expression of Runx in denervated muscle prevents myofibrillar disorganization and autophagy (Wang et al., *Genes Dev* 19: 1715-1722, 2005).

In conclusion, Nandrolone reduced denervation atrophy, but only after the initial phase of rapid catabolism is complete. These findings suggest that muscle may be receptive to the effects of anabolic steroids at some times, but not others, and that such changes in receptiveness relate to underlying biology of muscle atrophy.

We claim:

1. A recombinant nucleic acid comprising a heterologous polynucleotide sequence operably linked to a transcription regulatory sequence for the expression of said heterologous polynucleotide sequence, wherein the transcription regulatory sequence comprises the polynucleotide sequence of SEQ ID NO:1, and wherein the heterologous polynucleotide sequence encodes a polypeptide.

2. The recombinant nucleic acid of claim 1, wherein the transcription regulatory sequence comprises SEQ ID NO:2.

3. The recombinant nucleic acid of claim 1, wherein the transcription regulatory sequence comprises SEQ ID NO:3.

4. The recombinant nucleic acid of claim 1, wherein the heterologous polynucleotide sequence encodes a reporter, and wherein the reporter is selected from the group consisting of luciferase, green-fluorescent protein, beta galactosidase, and beta glucuronidase.

5. A plasmid comprising the recombinant nucleic acid of claim 1.

6. An isolated cell comprising the recombinant nucleic acid of claim 1.

7. The isolated cell of claim 6, further comprising a recombinant nucleic acid comprising a polynucleotide sequence encoding a reporter operably linked to an Insulin-like growth factor I (IGF-1) transcription regulatory sequence.

8. A kit comprising at least one of:
    (a) the recombinant nucleic acid of claim 1; and
    (b) an isolated cell comprising the recombinant nucleic acid of (a).

9. The kit of claim 8, further comprising at least one of:
    (c) a recombinant nucleic acid comprising a polynucleotide sequence encoding a reporter operably linked to an Insulin-like growth factor I (IGF-1) transcription regulatory sequence; and
(d) an isolated cell comprising the recombinant nucleic acid of (c).

10. The kit of claim 8, further comprising at least one steroid selected from the group consisting of testosterone, a synthetic anabolic steroid, a non-virulizing anabolic steroid, and a corticosteroid.

11. The kit of claim 10, comprising testosterone and dexamethasone.

* * * * *